(12) United States Patent
Benedini et al.

(10) Patent No.: US 7,718,656 B2
(45) Date of Patent: *May 18, 2010

(54) PROSTAGLANDIN DERIVATIVES

(75) Inventors: Francesca Benedini, Milan (IT); Valerio Chiroli, Milan (IT); Wesley Kwan Mung Chong, Encinitas, CA (US); Achim Hans-Peter Krauss, San Marcos, CA (US); Michael Ross Niesman, San Diego, CA (US); Ennio Ongini, Milan (IT)

(73) Assignee: Nicox S.A., Sophia Antipolis - Valbounne (FR)

( * ) Notice: Subject to any disclaimer, the term of this patent is extended or adjusted under 35 U.S.C. 154(b) by 891 days.

This patent is subject to a terminal disclaimer.

(21) Appl. No.: 11/478,129

(22) Filed: Jun. 28, 2006

(65) Prior Publication Data
US 2009/0062296 A1    Mar. 5, 2009

Related U.S. Application Data

(60) Provisional application No. 60/696,383, filed on Jun. 29, 2005.

(51) Int. Cl.
| | |
|---|---|
| A61K 31/495 | (2006.01) |
| A61K 31/445 | (2006.01) |
| A61K 31/215 | (2006.01) |
| C07D 241/04 | (2006.01) |
| C07D 211/06 | (2006.01) |
| C07C 69/76  | (2006.01) |

(52) U.S. Cl. .................. 514/252.12; 514/317; 514/506; 544/358; 546/184; 560/8; 560/55; 560/61; 560/62

(58) Field of Classification Search ............ 514/252.12, 514/317, 506; 544/358; 546/184; 560/8, 560/55, 61, 62
See application file for complete search history.

(56) References Cited

U.S. PATENT DOCUMENTS

| | | | |
|---|---|---|---|
| 3,922,293 | A | 11/1975 | Morozowich |
| 4,952,581 | A | 8/1990 | Bito et al. |
| 5,625,083 | A | 4/1997 | Bezuglov et al. |
| 5,811,443 | A | 9/1998 | DeSantis, Jr. et al. |
| 6,211,233 | B1 | 4/2001 | Del Soldato |
| 6,242,432 | B1 | 6/2001 | Del Soldato |
| 6,417,228 | B1 | 7/2002 | Klimko |
| 7,273,946 | B2 * | 9/2007 | Ongini et al. .................. 560/8 |

FOREIGN PATENT DOCUMENTS

| | | |
|---|---|---|
| WO | WO 90/02553 | 3/1990 |
| WO | WO 2005/049558 | 6/2005 |

* cited by examiner

*Primary Examiner*—Kamal A Saeed
*Assistant Examiner*—Samantha L Shterengarts
(74) *Attorney, Agent, or Firm*—Arent Fox LLP

(57) ABSTRACT

Nitroderivatives of prostaglandin amides having improved pharmacological activity and enhanced tolerability are described. They can be employed for the treatment of glaucoma and ocular hypertension.

17 Claims, No Drawings

PROSTAGLANDIN DERIVATIVES

CROSS-REFERENCE TO RELATED APPLICATION

This application claims priority to U.S. Patent Provisional Application Ser. No. 60/696,383, filed on Jun. 29, 2005, the disclosure of which is hereby incorporated in its entirety by reference.

The present invention relates to new prostaglandin derivatives. More particularly, the present invention relates to nitrooxyderivatives of prostaglandin amides, pharmaceutical compositions containing them and their use as drugs for treating glaucoma and ocular hypertension.

Glaucoma is optic nerve damage, often associated with increased intraocular pressure (IOP) that leads to progressive, irreversible loss of vision.

Almost 3 million people in the United States and 14 million people worldwide have glaucoma; this is the third leading cause of blindness worldwide.

Glaucoma occurs when an imbalance in production and drainage of fluid in the eye (aqueous humor) increases eye pressure to unhealthy levels.

It is known that elevated IOP can be at least partially controlled by administering drugs which either reduce the production of aqueous humor within the eye or increase the fluid drainage, such as beta-blockers, α-agonists, cholinergic agents, carbonic anhydrase inhibitors, or prostaglandin analogs.

Several side effects are associated with the drugs conventionally used to treat glaucoma.

Topical beta-blockers show serious pulmonary side effects, depression, fatigue, confusion, impotence, hair loss, heart failure and bradycardia.

Topical α-agonists have a fairly high incidence of allergic or toxic reactions; topical cholinergic agents (miotics) can cause visual side effects.

The side effects associated with oral carbonic anhydrase inhibitors include fatigue, anorexia, depression, paresthesias and serum electrolyte abnormalities (The Merck Manual of Diagnosis and Therapy, Seventeenth Edition, M. H. Beers and R. Berkow Editors, Sec. 8, Ch. 100).

Finally, the topical prostaglandin analogs (bimatoprost, latanoprost, travoprost and unoprostone) used in the treatment of glaucoma can produce ocular side effects, such as increased pigmentation of the iris, ocular irritation, conjunctival hyperaemia, iritis, uveitis and macular oedema (Martindale, Thirty-third edition, p. 1445)

U.S. Pat. No. 3,922,293 describes monocarboxyacylates of prostaglandins F-type and their 15β isomers, at the C-9 position, and processes for preparing them; U.S. Pat. No. 6,417,228 discloses 13-aza prostaglandins having functional $PGF_{2\alpha}$ receptor agonist activity and their use in treating glaucoma and ocular hypertension.

WO 90/02553 discloses the use of prostaglandins derivatives of PGA, PGB, PGE and PGF, in which the omega chain contains a ring structure, for the treatment of glaucoma or ocular hypertension.

WO 00/51978 describes novel nitrosated and/or nitrosylated prostaglandins, in particular novel derivatives of $PGE_1$, novel compositions and their use for treating sexual dysfunctions.

U.S. Pat. No. 5,625,083 discloses dinitroglycerol esters of prostaglandins which may be used as vasodilators, antihypertensive cardiovascular agents or bronchodilators.

U.S. Pat. No. 6,211,233 discloses compounds of the general formula $A-X_1-NO_2$, wherein A contains a prostaglandin residue, in particular $PGE_1$, and $X_1$ is a bivalent connecting bridge, and their use for treating impotence.

WO 2005/049558 discloses compositions comprising an amide related to a prostaglandin and an amine selected from the group consisting of epinephrine, dopamine, diacetyl dopamine and serotonin, and their use for treating glaucoma.

It is an object of the present invention to provide new derivatives of prostaglandins able not only to eliminate or at least reduce the side effects associated with these compounds, but also to possess an improved pharmacological activity. It has been surprisingly found that nitroderivatives of prostaglandin amides have a significantly improved overall profile as compared to native prostaglandins both in terms of wider pharmacological activity, enhanced tolerability and long-acting hypotensive activity. In particular, it has been recognized that the prostaglandin nitroderivatives of the present invention can be employed for treating glaucoma and ocular hypertension. The compounds of the present invention are indicated for the reduction of intraocular pressure in patients with open-angle glaucoma or with chronic angle-closure glaucoma who underwent peripheral iridotomy or laser iridoplasty.

An object of the present invention is, therefore, nitroderivatives of prostaglandin amides of general formula (I) and pharmaceutically acceptable salts or stereoisomers thereof $$R-X-(B)_m-Y-ONO_2 \quad (I)$$

wherein R is the prostaglandin residue of formula (II):

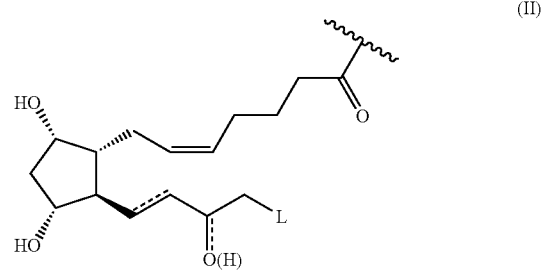

wherein the symbol  represents a single bond or a double bond;

L is selected from the following groups:

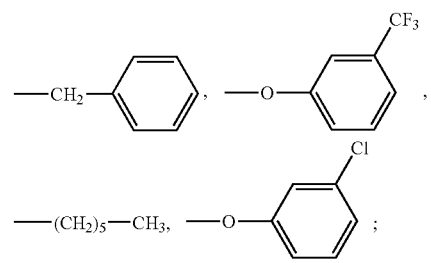

X is $-NR^1-$, wherein $R^1=H$ or $C_1-C_6$ alkyl;

m is an integer equal to 0 or 1;

B is a radical of the formula $-CH(R^1)COO-$, wherein $R^1$ is as above defined;

Y is a bivalent radical having the following meaning:

a)
straight or branched $C_1$-$C_{20}$ alkylene, being optionally substituted with one or more of the substituents selected from the group consisting of: halogen atoms, hydroxy, —$ONO_2$ or T, wherein T is —OC(O)($C_1$-$C_{10}$ alkyl)-$ONO_2$ or —O($C_1$-$C_{10}$ alkyl)-$ONO_2$;
cycloalkylene with 5 to 7 carbon atoms into cycloalkylene ring, the ring being optionally substituted with side chains $T_1$, wherein $T_1$ is straight or branched $C_1$-$C_{10}$ alkyl;

b)

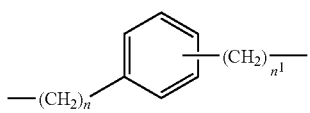

c)

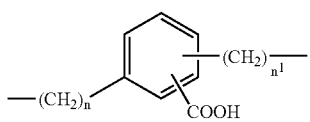

wherein n is an integer from 0 to 20, and n' is an integer from 1 to 20;

d)

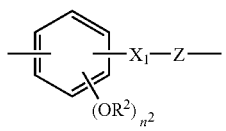

wherein $X_1$=—OCO— or —COO— and $R^2$ is H or $CH_3$;

Z is —$(CH_2)_n$— or the bivalent radical defined above under b);

$n^1$ is as defined above and $n^2$ is an integer from 0 to 2;

e)

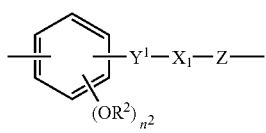

wherein:

$Y^1$ is $CH_2$—$CH_2$—$(CH_2)_{n^2}$— or —CH=CH—$(CH_2)_{n^2}$—;

Z, $n^1$, $n^2$, $R^2$ and X, are as defined above;

with the proviso that:
i) when Y is selected from the bivalent radicals mentioned under b)-e), then the terminal —$NO_2$ group is bound to —$(CH_2)_{n^1}$;

ii) when y is selected from the bivalent radicals mentioned under b) or c) and n=0, then m=1;
iii) when y is selected from the bivalent radicals mentioned under d) or e), then m=1;

g)

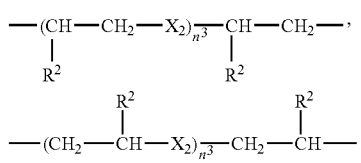

wherein $X_2$ is —O— or —S—, $n^3$ is an integer from 1 to 6, $R^2$ is as defined above;

h)

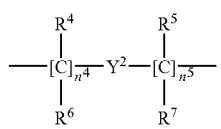

wherein:

$n^4$ is an integer from 0 to 10;

$n^5$ is an integer from 1 to 10;

$R^4$, $R^5$, $R^6$, $R^7$ are the same or different, and are H or straight or branched $C_1$-$C_4$ alkyl;

wherein the —$ONO_2$ group is linked to

wherein $n^5$ is as defined above;

$Y^2$ is an heterocyclic saturated, unsaturated or aromatic 5 or 6 members ring, containing one or more heteroatoms selected from nitrogen, oxygen, sulfur, and is selected from

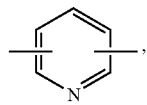  (Y1)

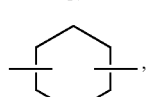  (Y2)

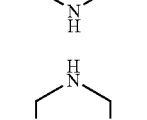  (Y3)

-continued

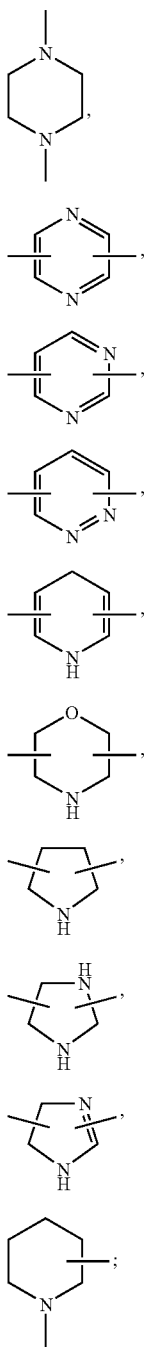

(Y4)
(Y5)
(Y6)
(Y7)
(Y8)
(Y9)
(Y10)
(Y11)
(Y12)
(Y13)

Preferred compounds of formula (I) are those wherein R, L, X and B are as above defined and Y is a bivalent radical having the following meaning:

a)
straight or branched $C_1$-$C_{10}$ alkylene, being optionally substituted with one or more of the substituents selected from the group consisting of: halogen atoms, hydroxy, —$ONO_2$ or T, wherein T is
—OC(O)($C_1$-$C_{10}$ alkyl)-$ONO_2$ or —O($C_1$-$C_{10}$ alkyl)-$ONO_2$;

cycloalkylene with 5 to 7 carbon atoms into cycloalkylene ring, the ring being optionally substituted with side chains $T_1$, wherein $T_1$ is $CH_3$;

b)

c)

—(CH$_2$)$_n$—⟨benzene⟩—(CH$_2$)$_{n^1}$—
                    COOH wherein n is an integer from 0 to 5, and $n^1$ is an integer from 1 to 5;

d)

—⟨benzene⟩—$X_1$—Z—
   (OR$^2$)$_{n^2}$ wherein:

$X_1$=—OCO— or —COO— and $R^2$ is H or $CH_3$;

Z is —(CH$_2$)$_{n^1}$— or the bivalent radical defined above under b);

$n^1$ is an integer from 1 to 10 and $n^2$ is an integer from 0 to 2;

e)

—⟨benzene⟩—$Y^1$—$X_1$—Z—
   (OR$^2$)$_{n^2}$ wherein:

$Y^1$ is —$CH_2$—$CH_2$— or —CH=CH—(CH$_2$)$_{n^2}$—;

Z, $n^1$, $n^2$, $R^2$ and $X_1$ are as above defined;

with the proviso that:

i) when Y is selected from the bivalent radicals mentioned under b)-e), then the terminal —$ONO_2$ group is bound to —(CH$_2$)$_{n^1}$;

ii) when y is selected from the bivalent radicals mentioned under b) or c) and n=0, then m=1;

iii) when y is selected from the bivalent radicals mentioned under d) or e), then m=1;

g)

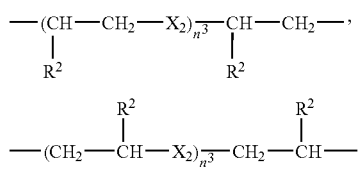

wherein $X_2$ is —O— or —S—, $n^3$ is an integer from 1 to 4 and $R^2$ is as defined above;

h)

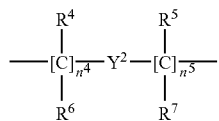

wherein:

$n^4$ is an integer from 0 to 3;

$n^5$ is an integer from 1 to 3;

$R^4$, $R^5$, $R^6$, $R^7$ are H;

wherein the —ONO$_2$ group is linked to

wherein $n^5$ is as defined above;

$Y^2$ is selected from

 (Y1)

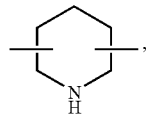 (Y2)

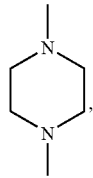 (Y4)

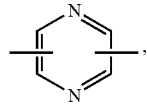 (Y5)

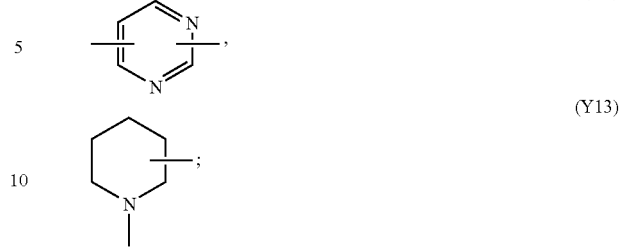

The term "$C_1$-$C_{20}$ alkylene" as used herein refers to branched or straight chain $C_1$-$C_{20}$ hydrocarbon, preferably having from 1 to 10 carbon atoms such as methylene, ethylene, propylene, isopropylene, n-butylene, pentylene, n-hexylene and the like.

The term "$C_1$-$C_{10}$ alkyl" as used herein refers to branched or straight chain alkyl groups comprising one to ten carbon atoms, including methyl, ethyl, n-propyl, isopropyl, n-butyl, isobutyl, t-butyl, pentyl, hexyl, octyl and the like.

The term "cycloalkylene" as used herein refers to ring having from 5 to 7 carbon atoms including, but not limited to, cyclopentylene, cyclohexylene optionally substituted with side chains such as straight or branched ($C_1$-$C_{10}$)-alkyl, preferably $CH_3$.

The term "heterocyclic" as used herein refers to saturated, unsaturated or aromatic 5 or 6 members ring, containing one or more heteroatoms selected from nitrogen, oxygen, sulphur, such as for example pyridine, pyrazine, pyrimidine, pyrrolidine, morpholine, imidazole and the like.

Preferred compounds of formula (I) are those wherein the prostaglandin residue R is selected from the group consisting of latanoprost, travoprost, unoprostone and cloprostenol, preferably R is latanoprost.

Most preferred meanings of Y are:

a)
straight or branched $C_2$-$C_6$ alkylene, being optionally substituted with —ONO$_2$;

b)

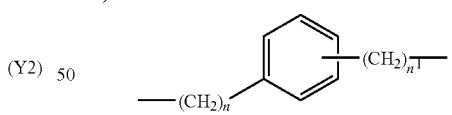

wherein n is 0 or 1, and $n^1$ is 1;

d)

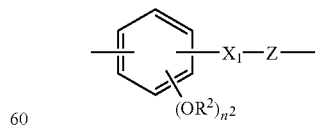

wherein $X_1$=—OCO— or —COO— and $R^2$ is H or $CH_3$;

Z is —(CH$_2$)$_{n^1}$—;

n' is an integer from 1 to 5 and $n^2$ is as above defined;

e)

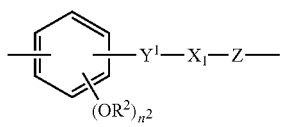

wherein:

$Y^1$ is —$CH_2$—$CH_2$—$(CH_2)_2$— or —$CH$=$CH$—$(CH_2)_n{}^2$—;

Z is —$(CH_2)_n{}^1$— or the bivalent radical defined above under b);

$n^1$ is an integer from 1 to 5;

$n^2 R^2$ and $X_1$ are as above defined;

g)

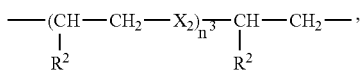

h)

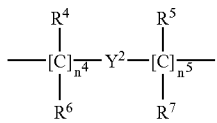

wherein:

$n^4$ is 2 or 3;

$n^5$ is 2 or 3;

$R^4, R^5, R^6, R^7$ are H;

wherein the —$ONO_2$ group is linked to

wherein $n^5$ is as defined above;

$Y^2$ is selected from

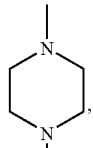 (Y4)

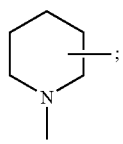 (Y13)

The following are preferred compounds according to the present invention:

(1)

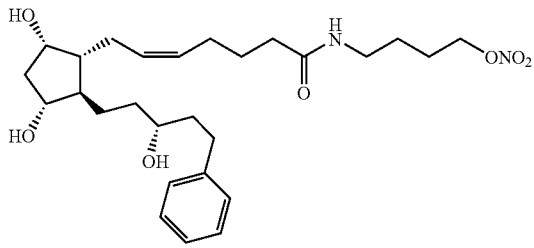

(2)

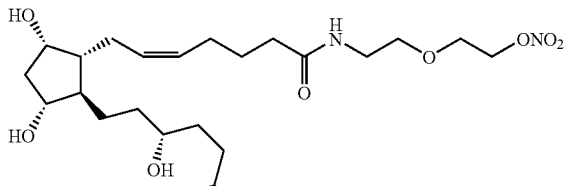

(3)

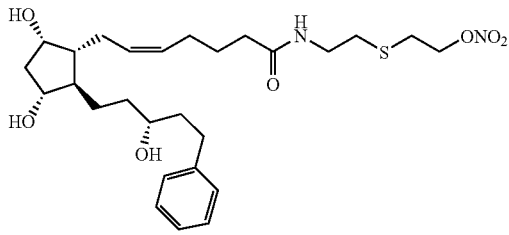

(4)

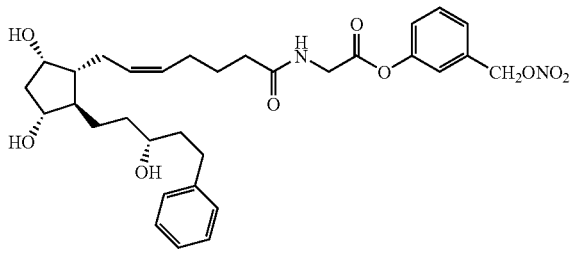

-continued
(5)
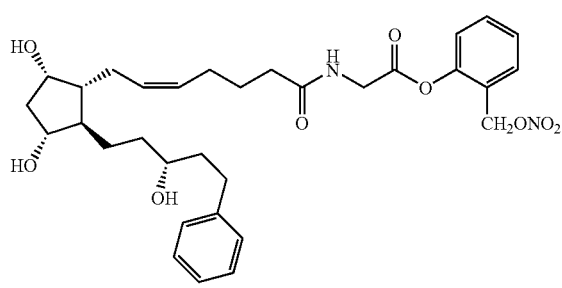
(6)
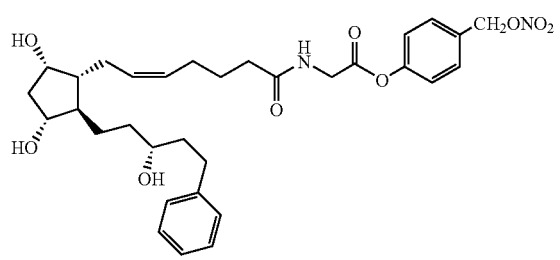
(7)
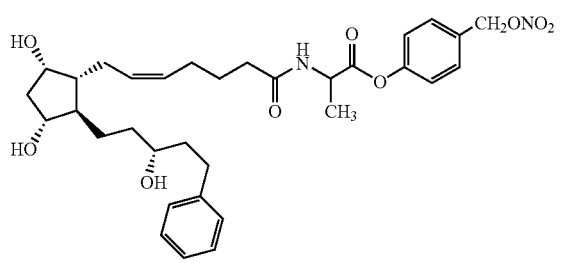
(8)
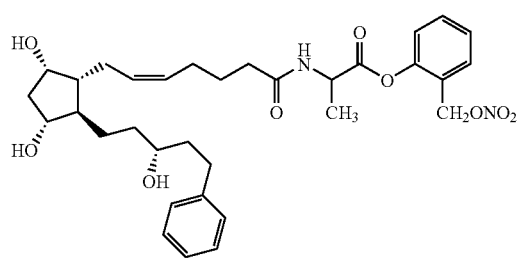
(9)
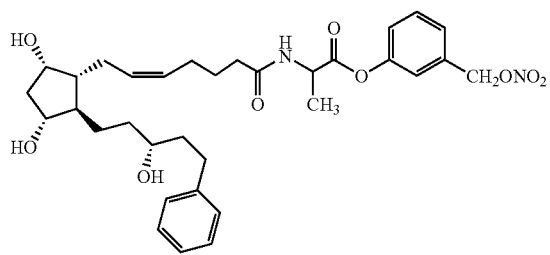
(10)
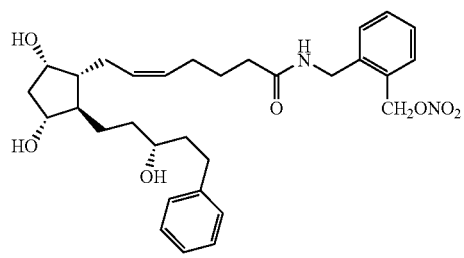
(11)
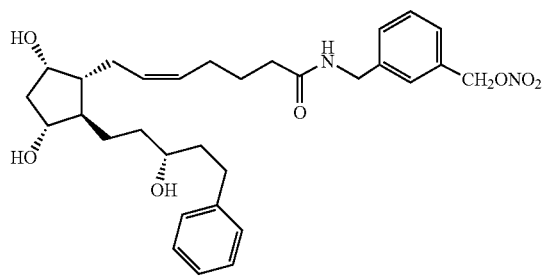
(12)
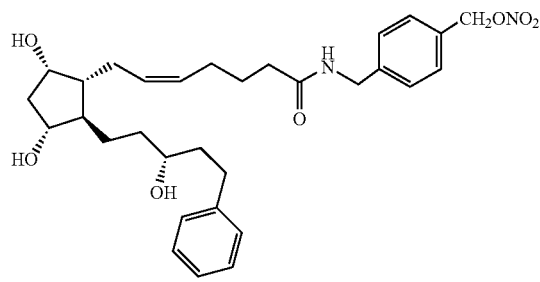
(13)
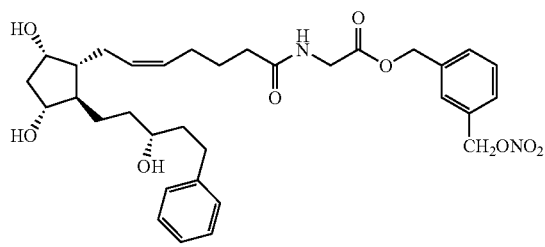
(14)
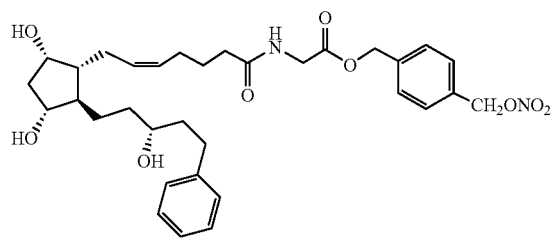

-continued
(15)
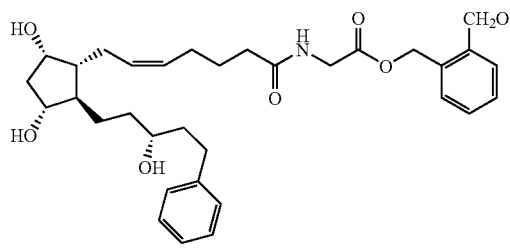
(16)
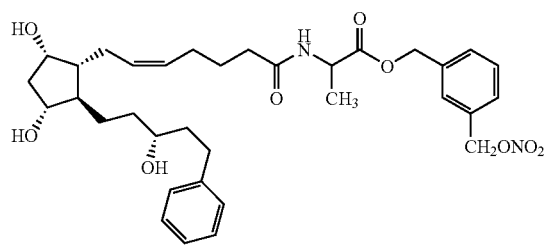
(17)
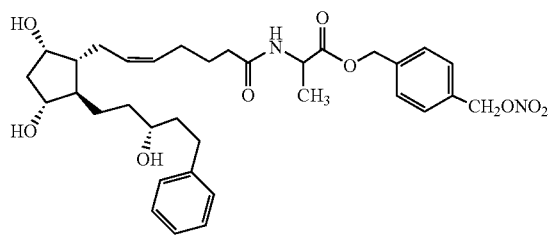
(18)
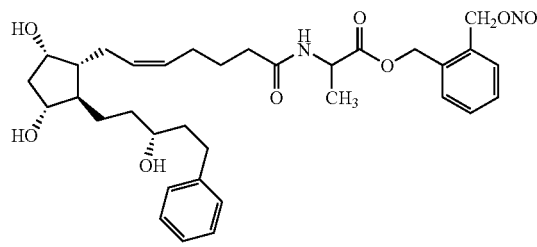
(19)
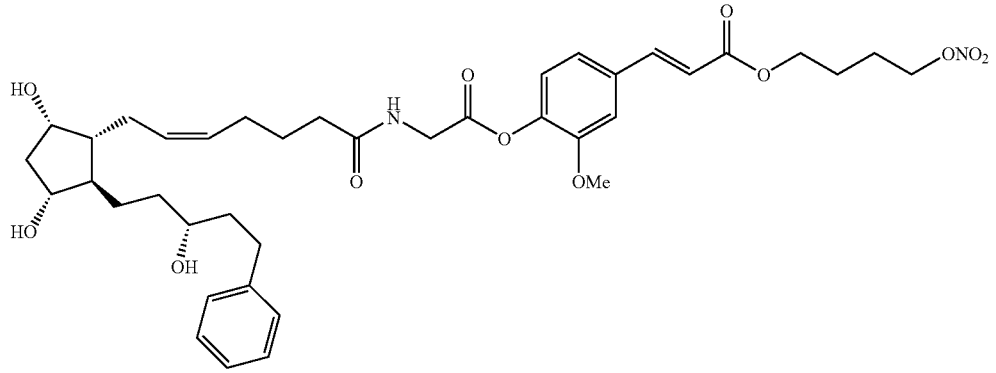
(20)
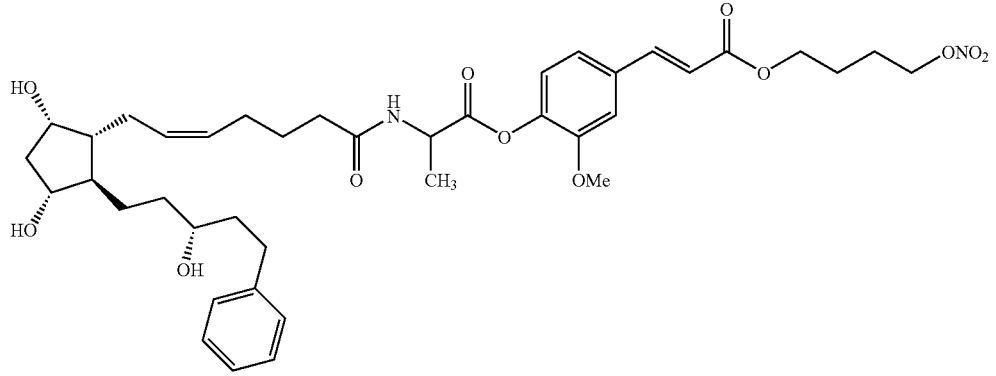
(21)
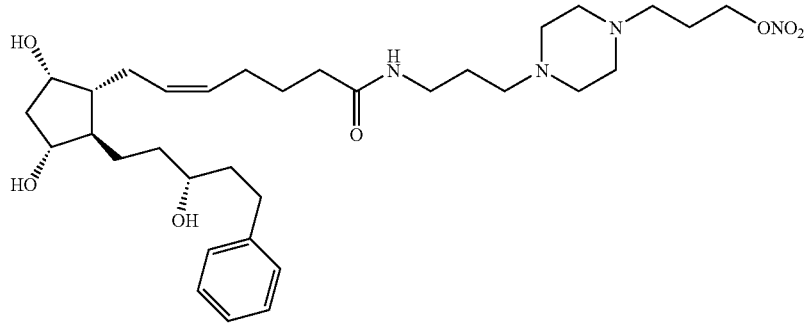

-continued
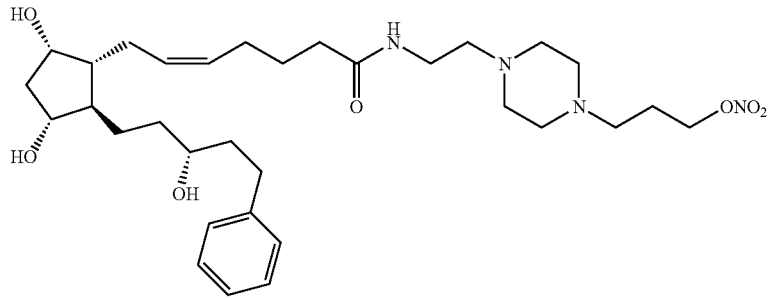
(22)
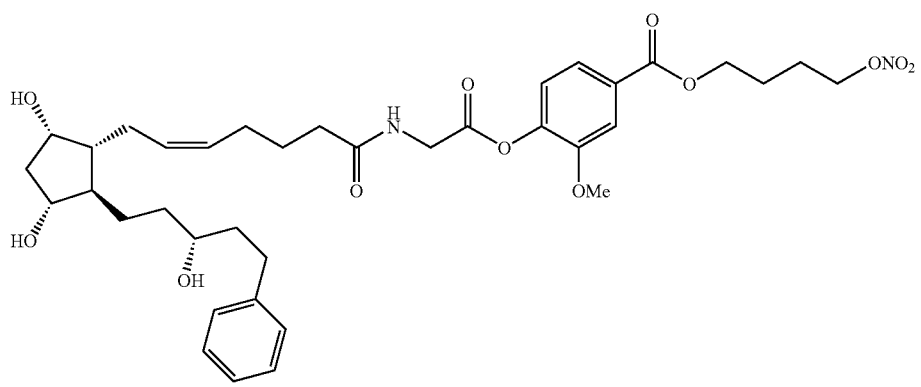
(23)
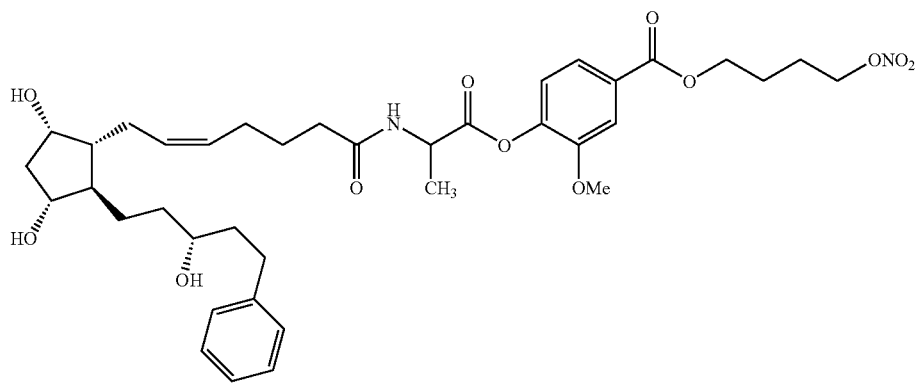
(24)
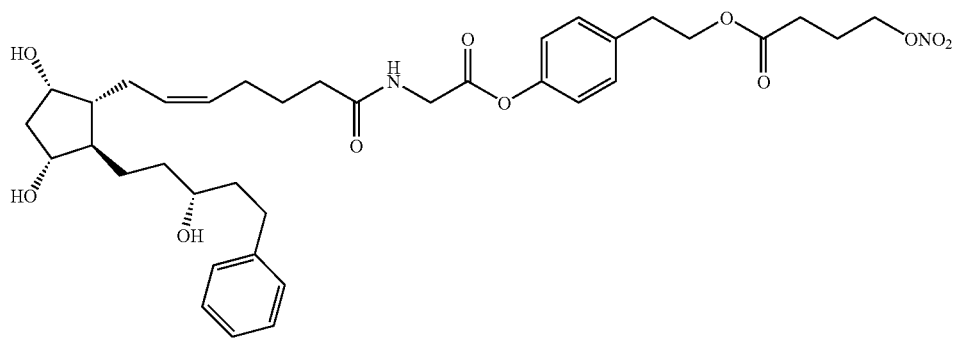
(25)

-continued
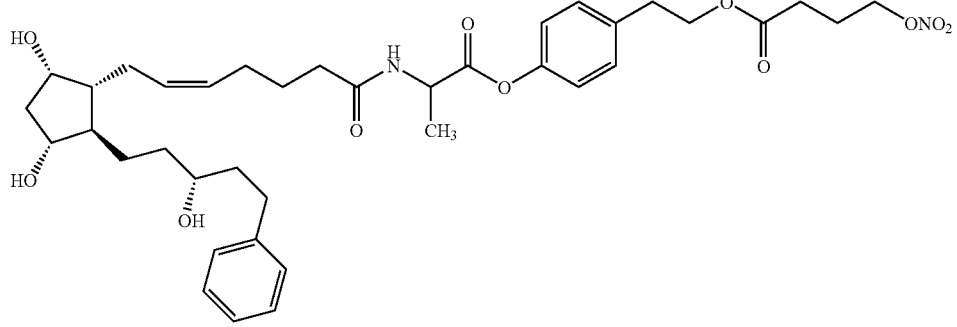
(26)
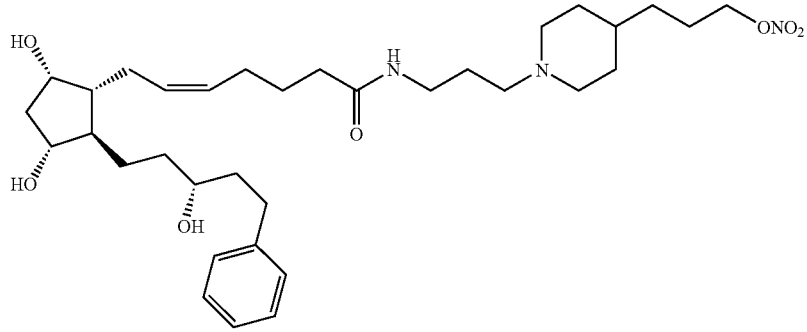
(27)
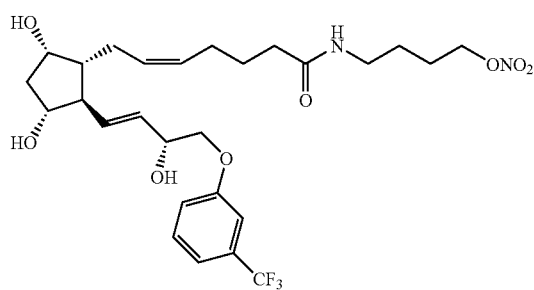
(28)
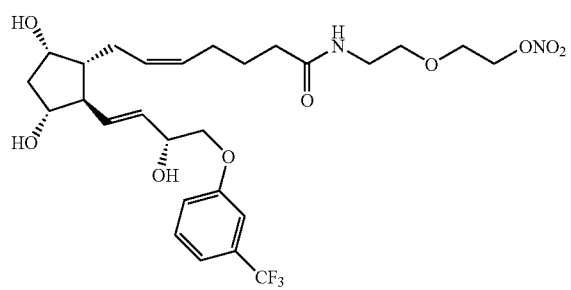
(29)
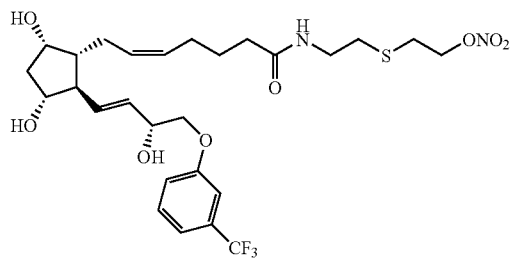
(30)
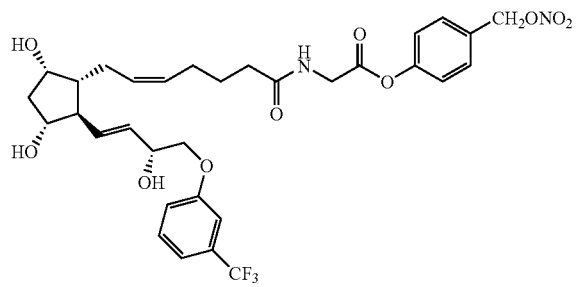
(31)
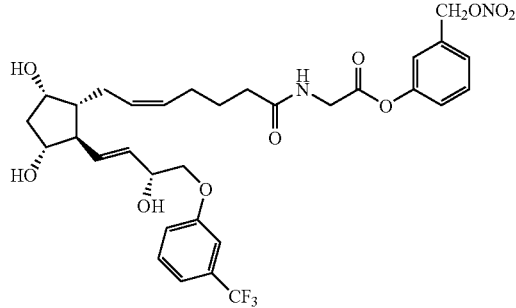
(32)
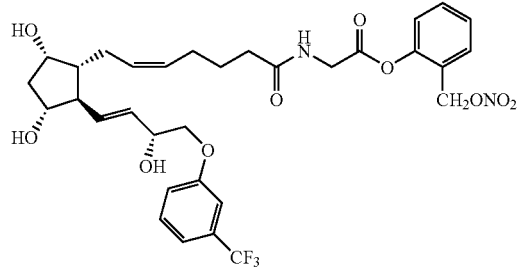
(33)

-continued
(34)
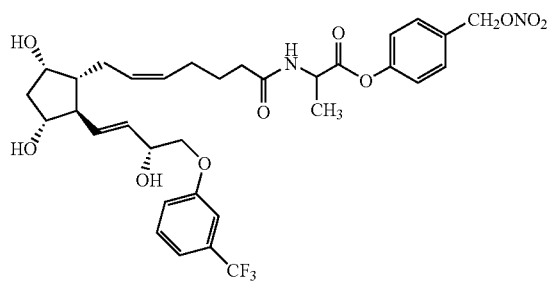
(35)
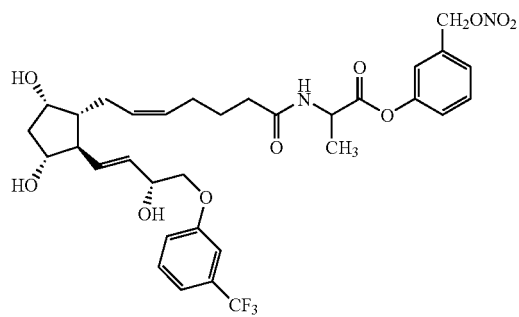
(36)
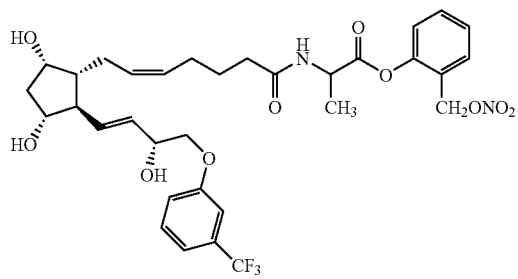
(37)
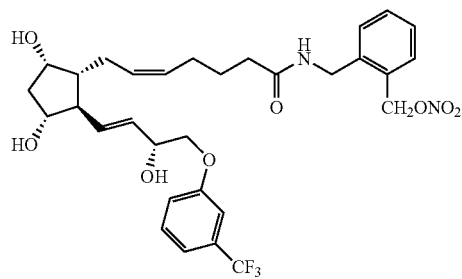
(38)
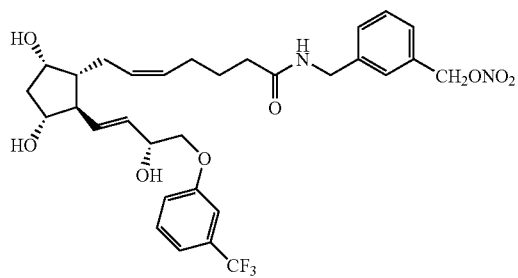
(39)
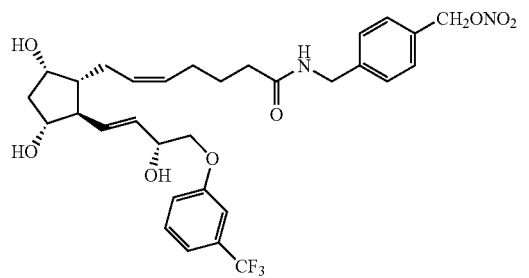
(40)
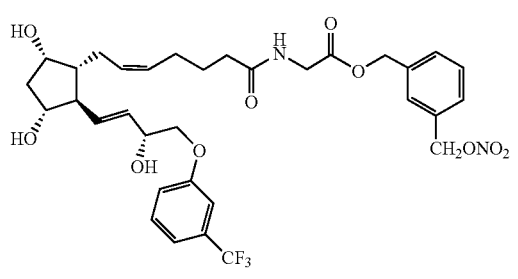
(41)
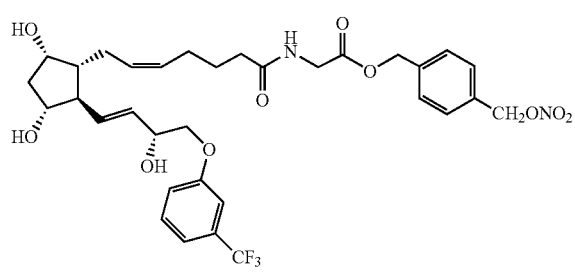
(42)
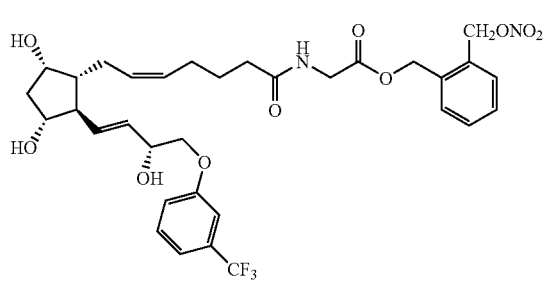
(43)
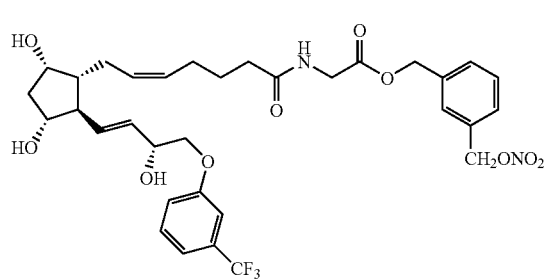

-continued
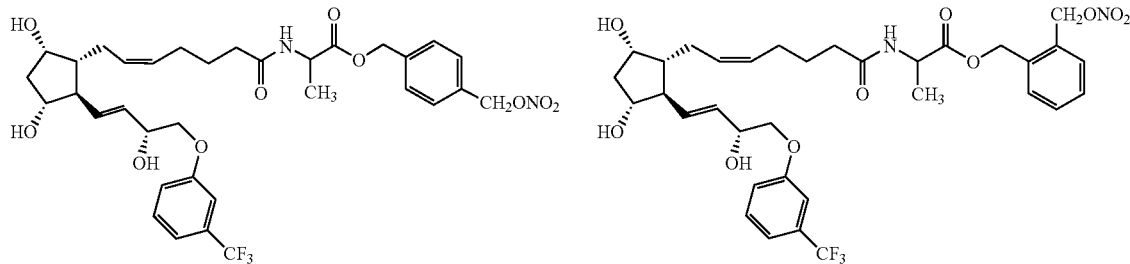
(44) (45)
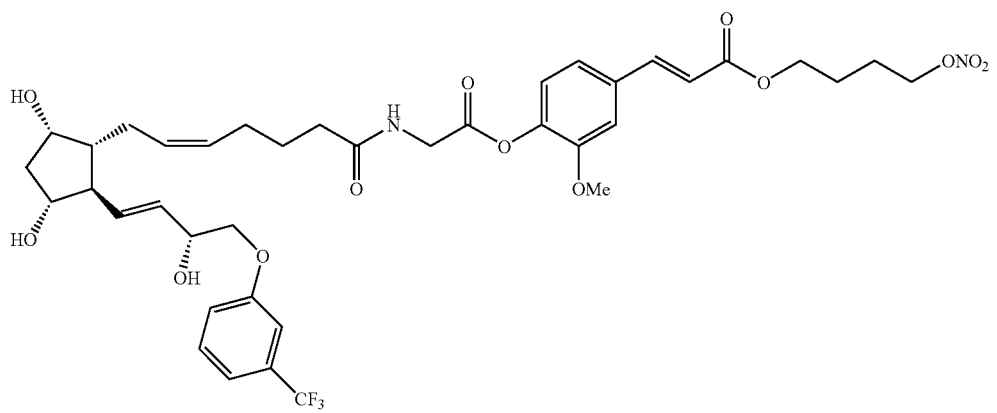
(46)
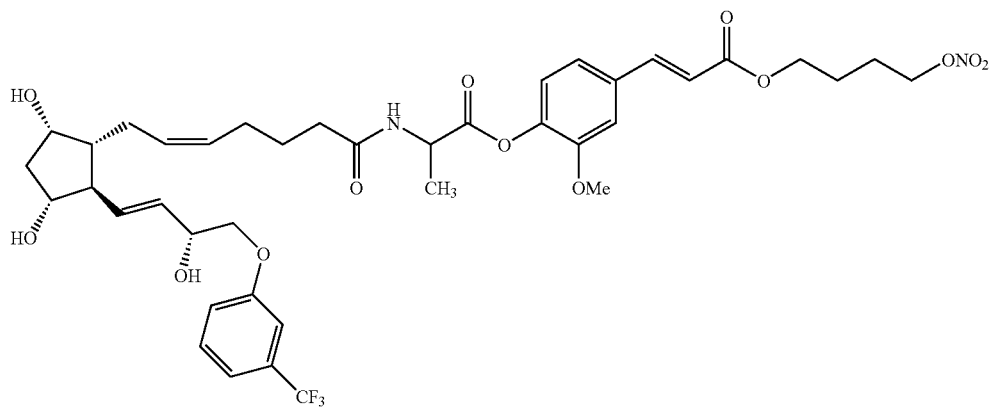
(47)
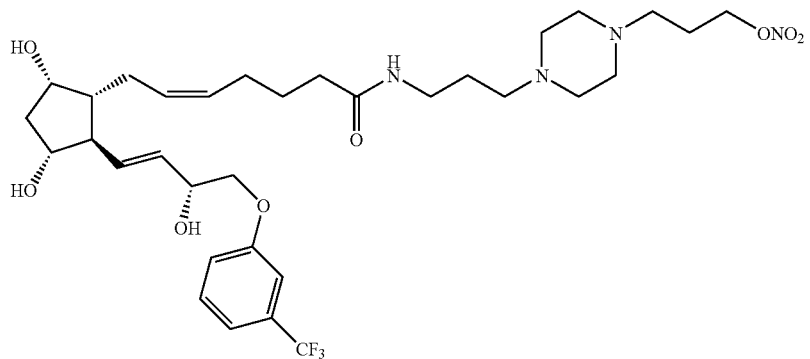
(48)

-continued
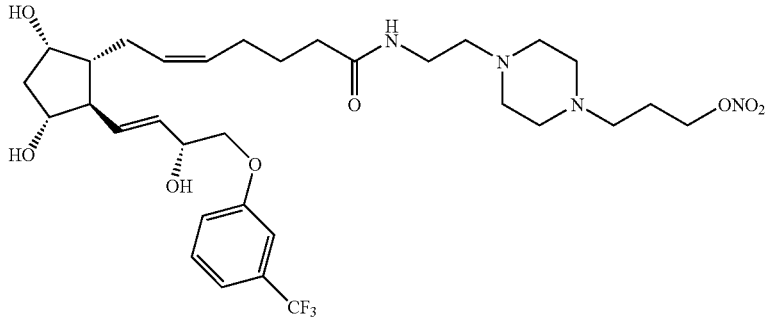
(49)
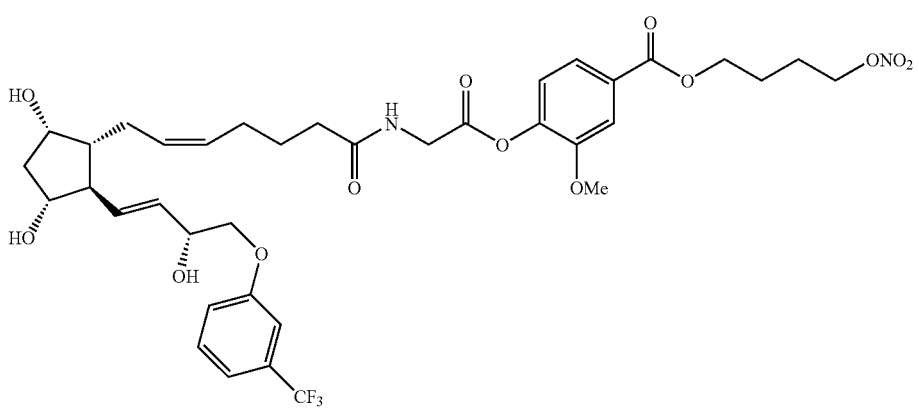
(50)
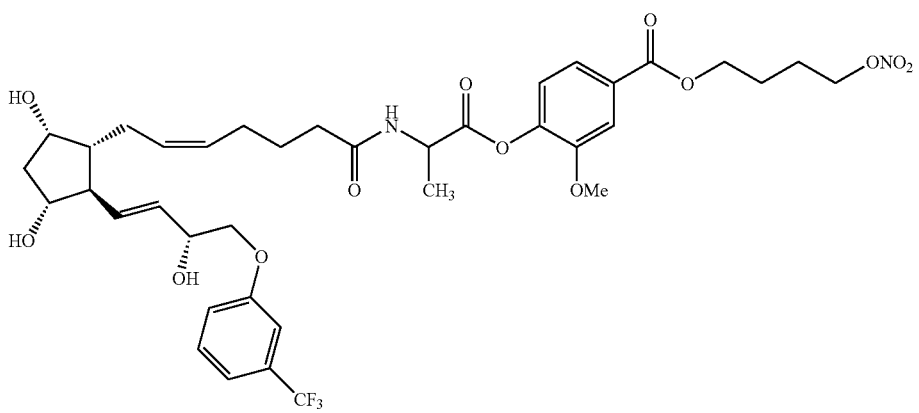
(51)
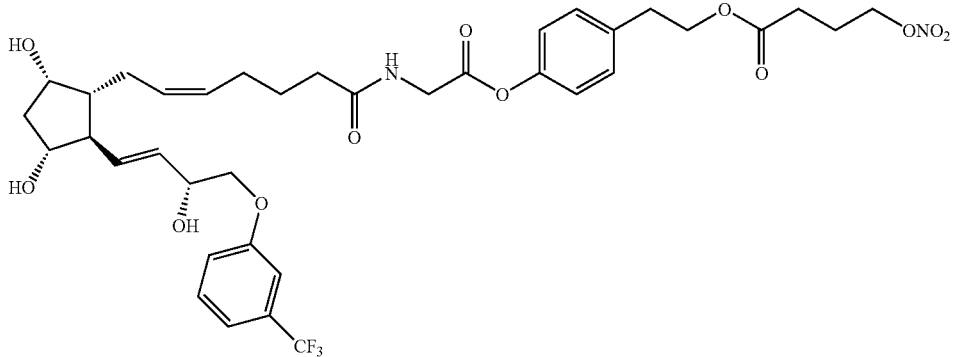
(52)

-continued
(53)
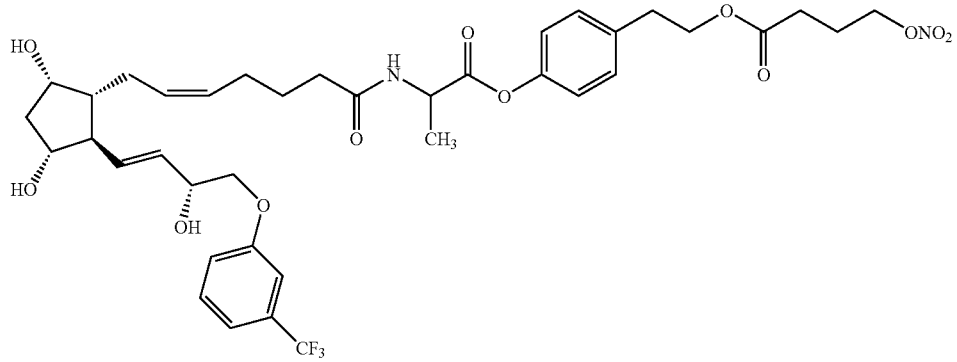
(54)
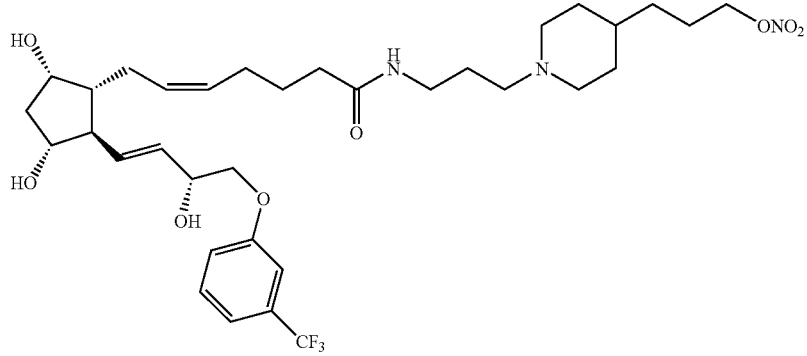
(55)
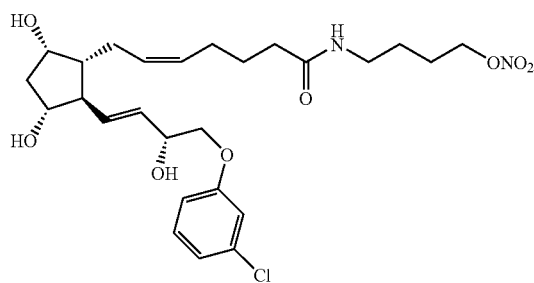
(56)
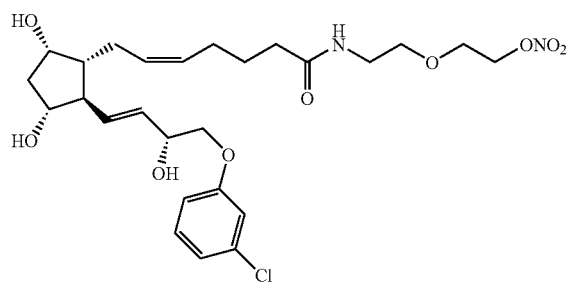
(57)
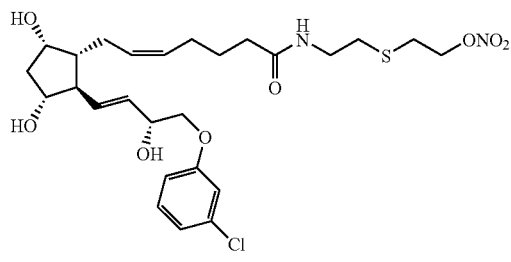
(58)
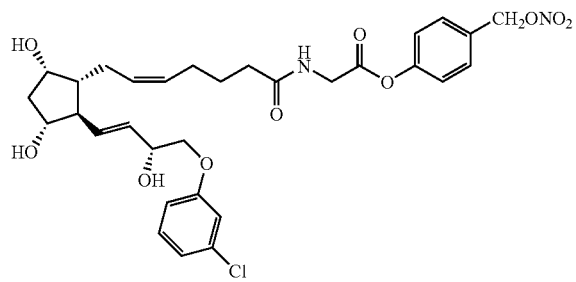

-continued
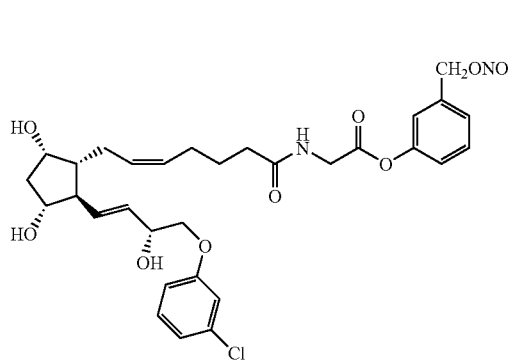
(59)
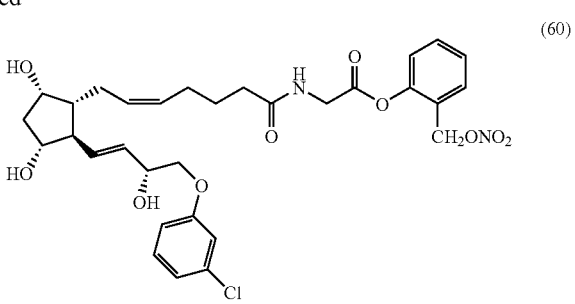
(60)
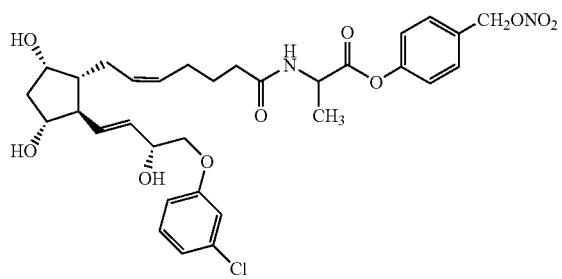
(61)
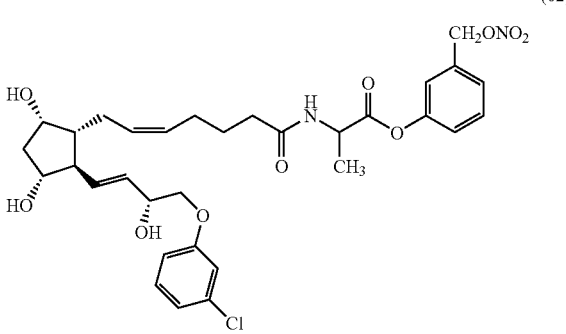
(62)
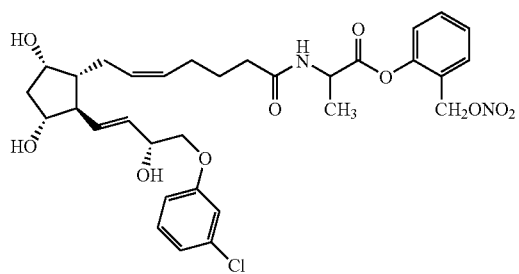
(63)
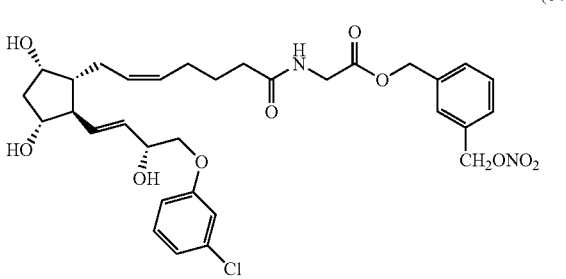
(64)
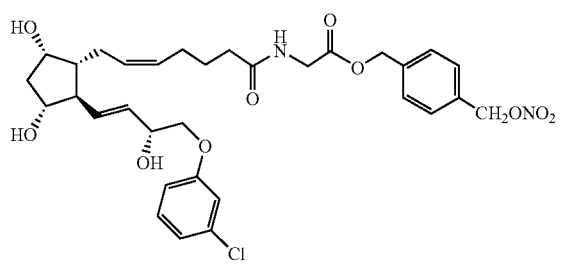
(65)
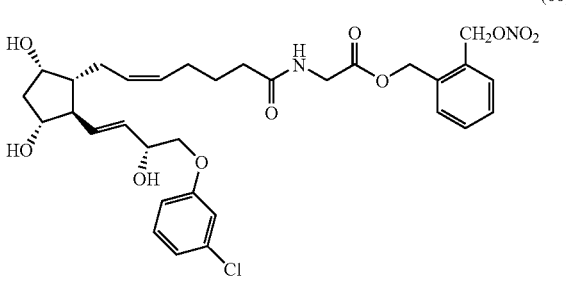
(66)
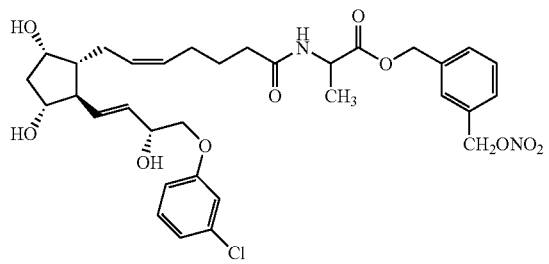
(67)
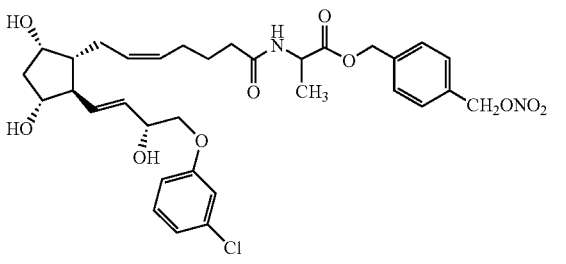
(68)

-continued
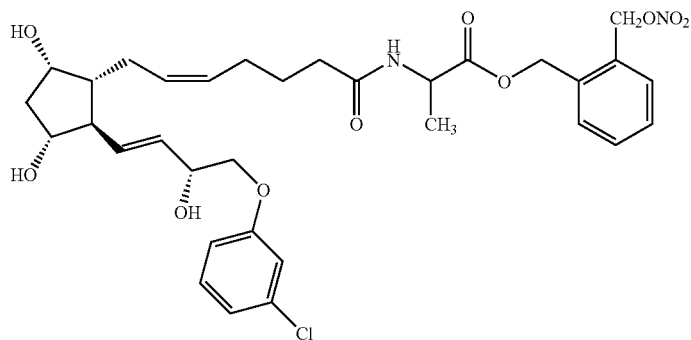
(69)
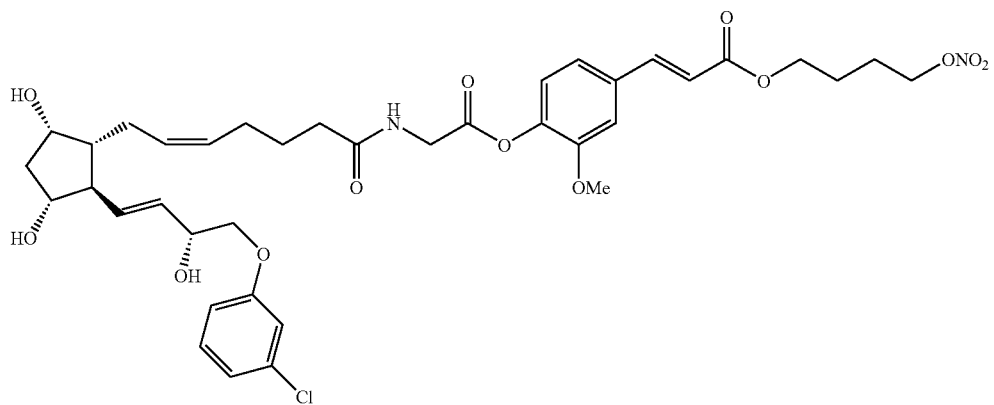
(70)
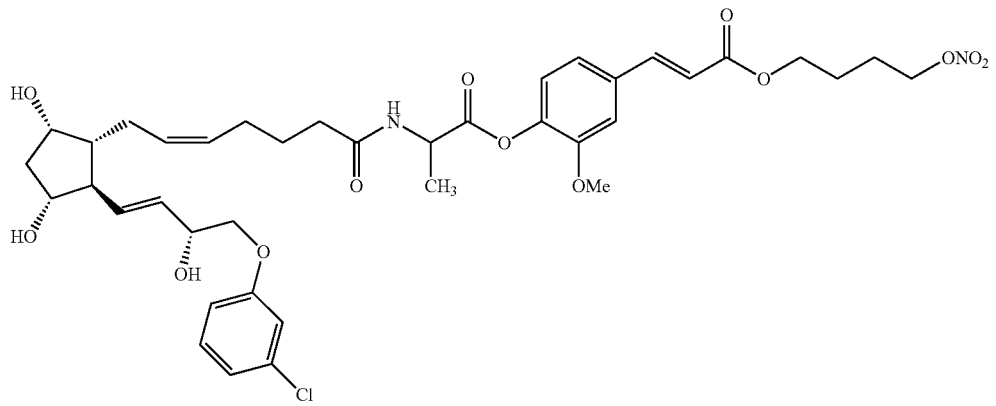
(71)
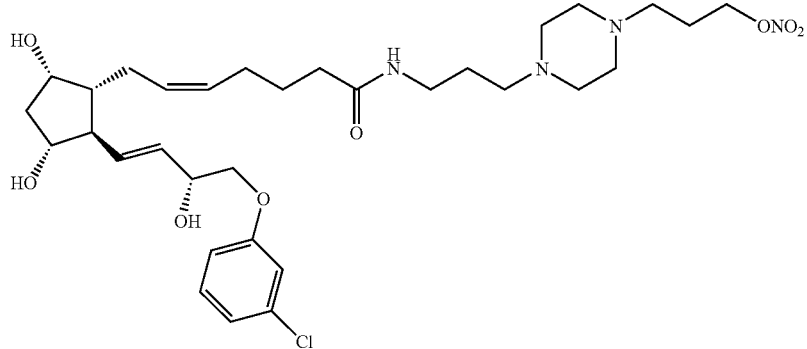
(72)

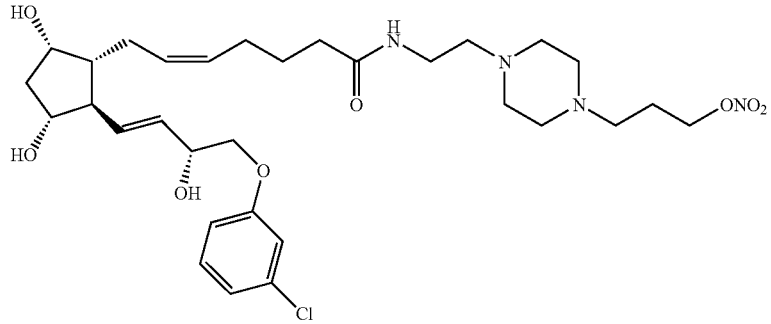
(73)
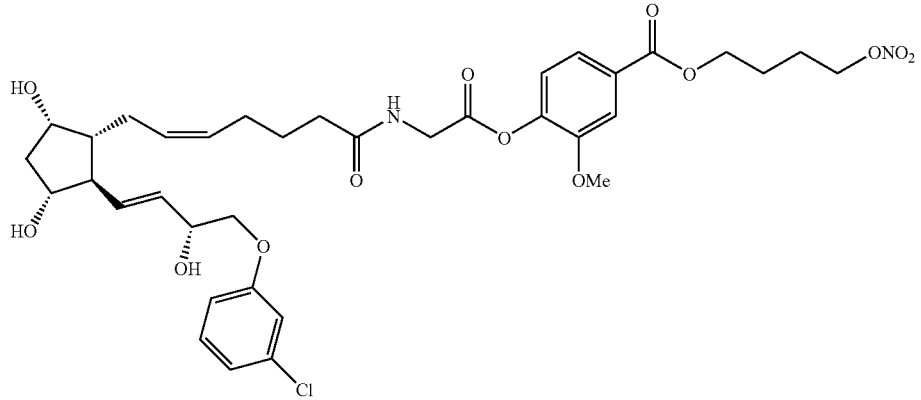
(74)
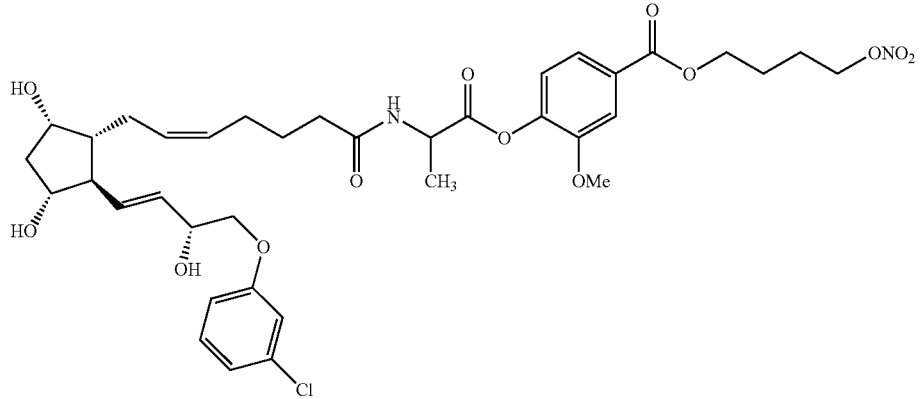
(75)
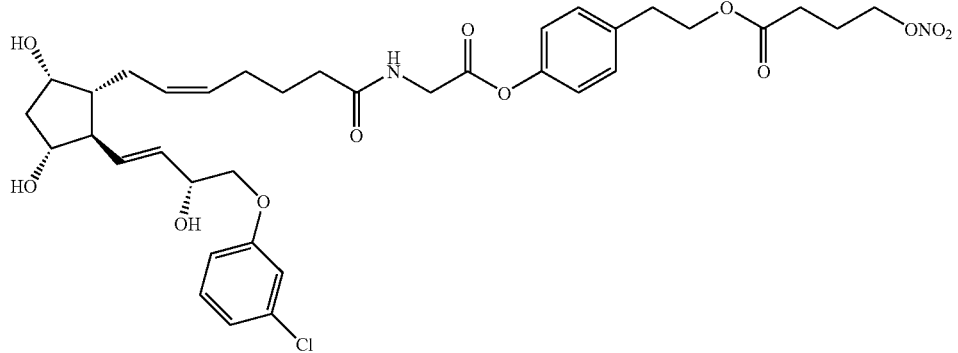
(76)

-continued
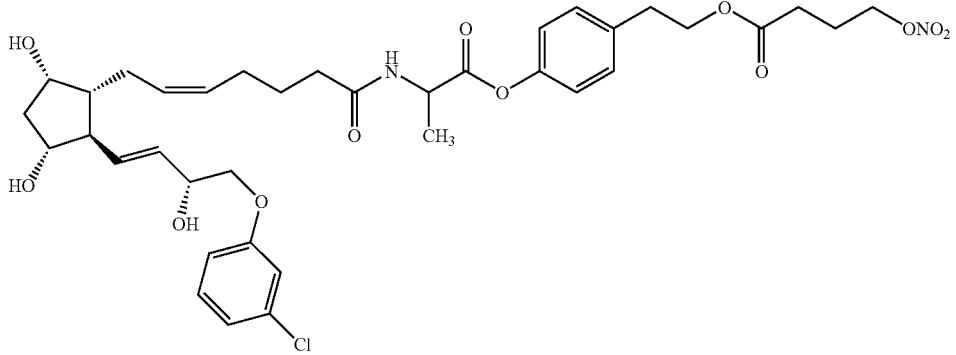
(77)
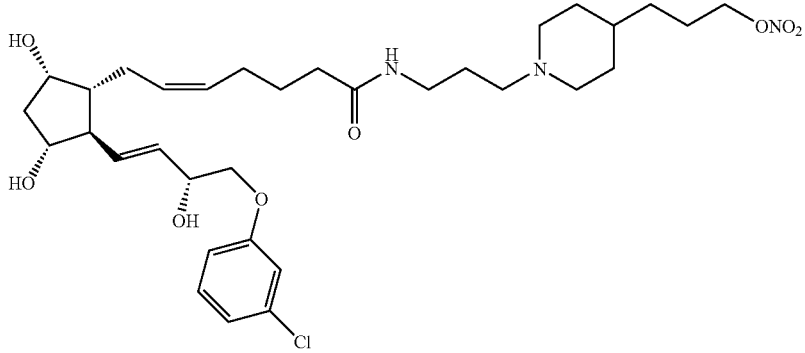
(78)
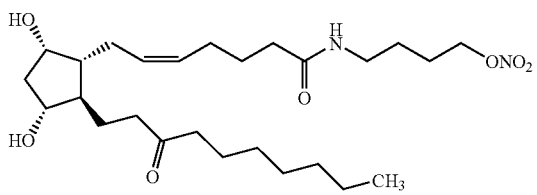
(79)
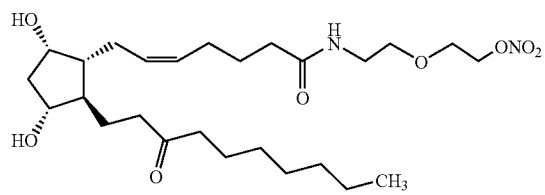
(80)
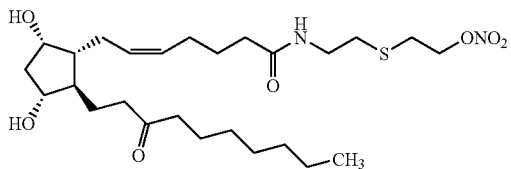
(81)
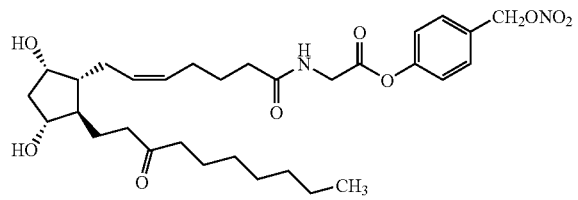
(82)
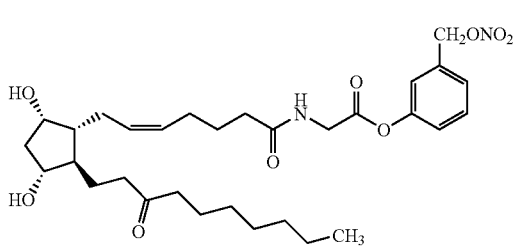
(83)
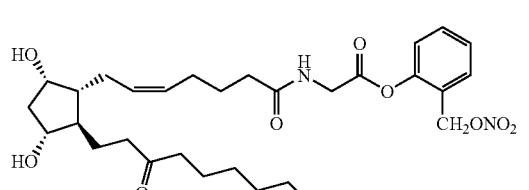
(84)

-continued
(85)
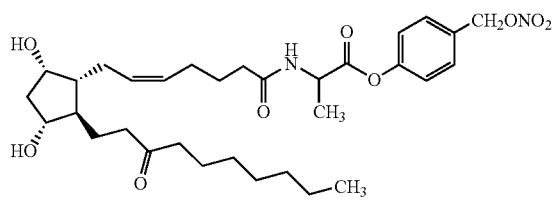
(86)
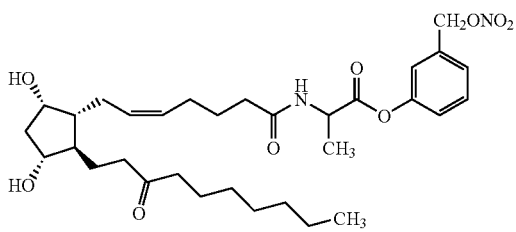
(87)
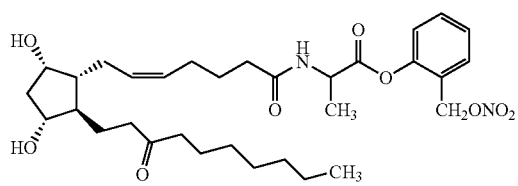
(88)
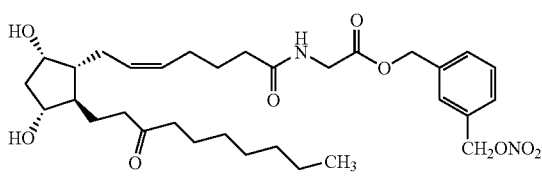
(89)
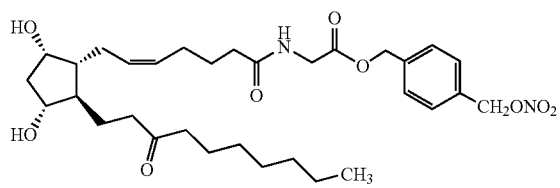
(90)
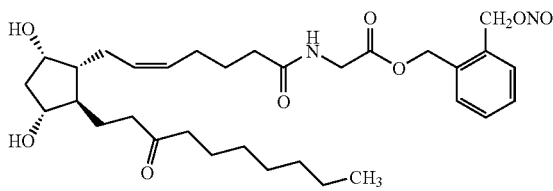
(91)
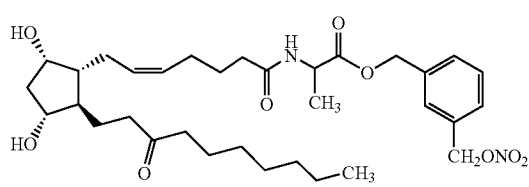
(92)
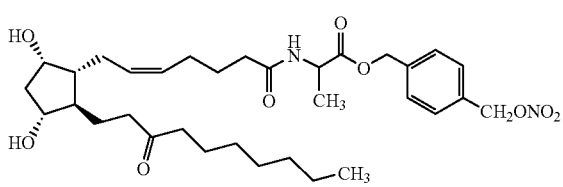
(93)
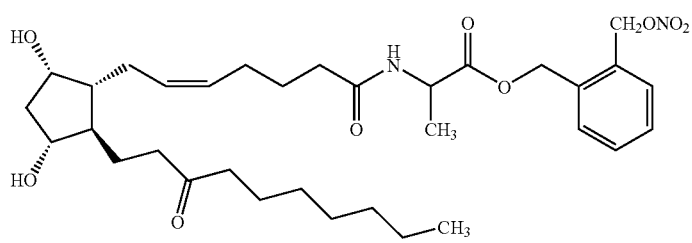
(94)
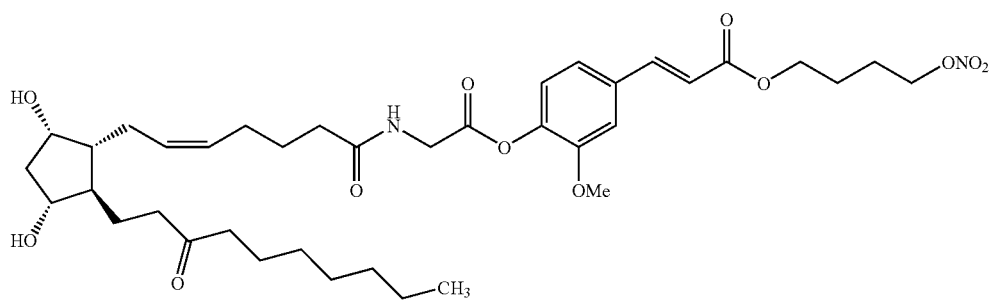

-continued
(95)
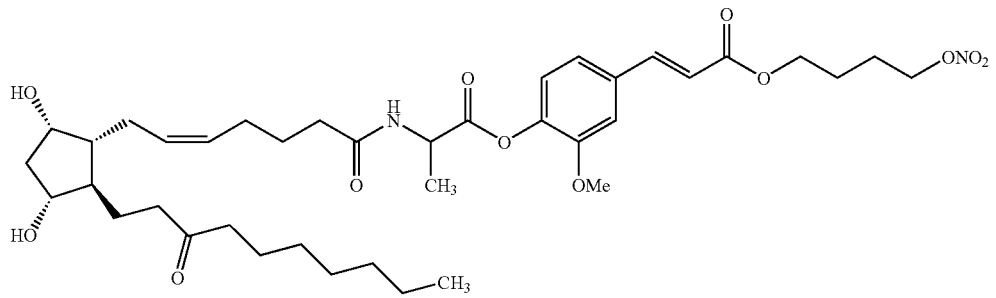
(96)
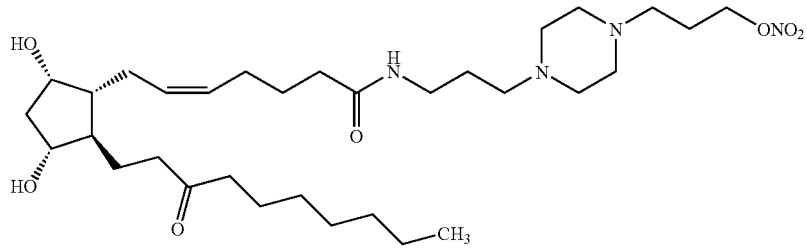
(97)
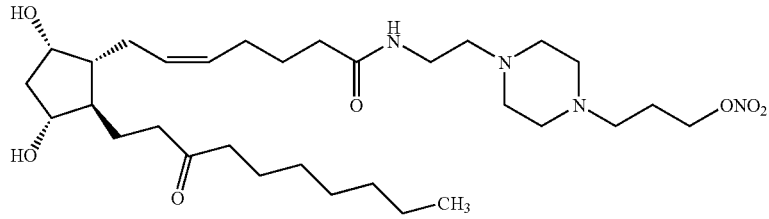
(98)
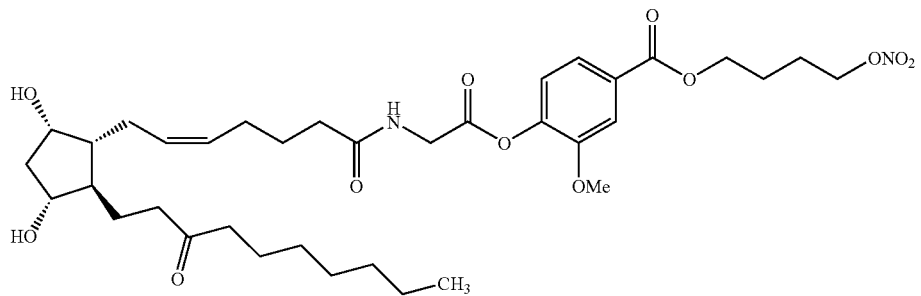
(99)
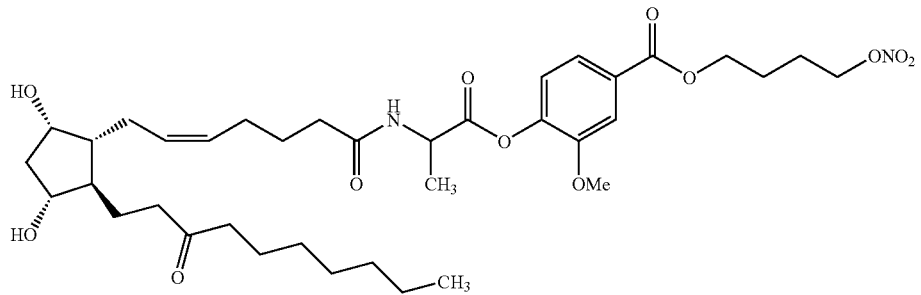

(100)
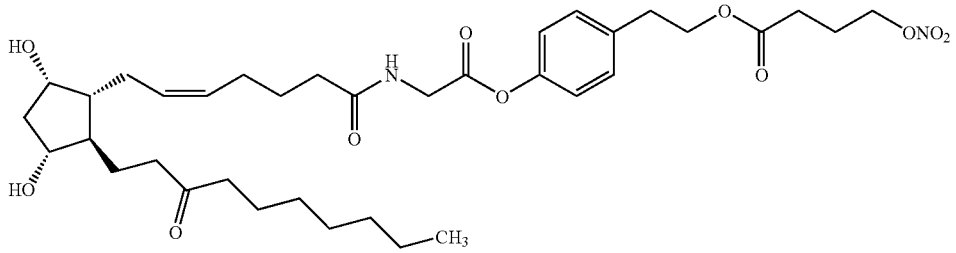
(101)
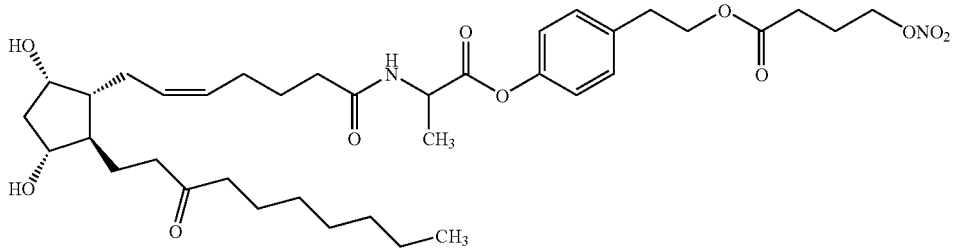
(102)
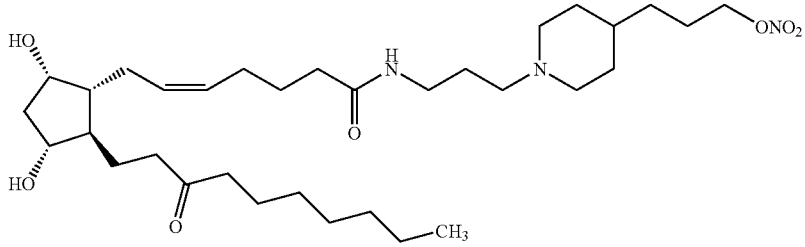
(103)
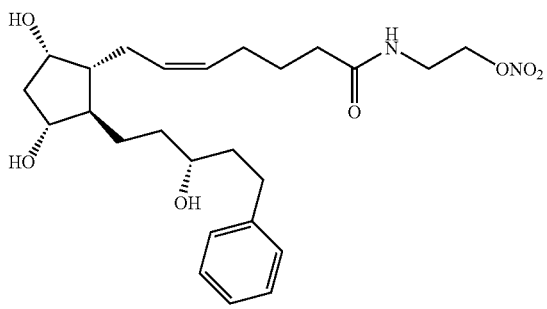
(104)
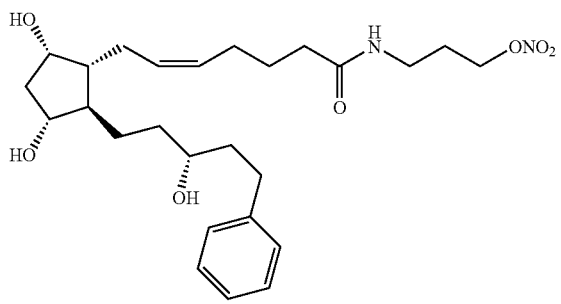
(105)
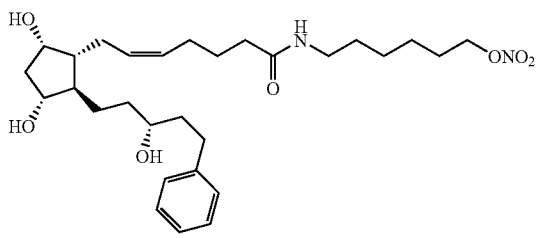
(106)
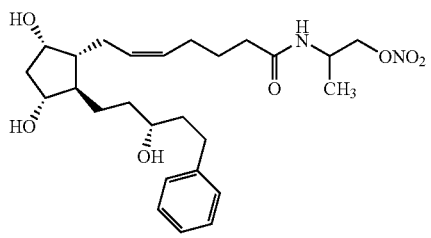

-continued
(107)
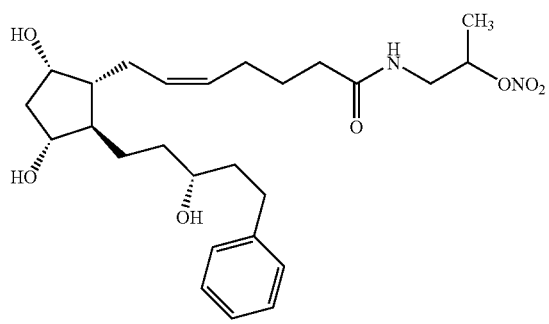
(108)
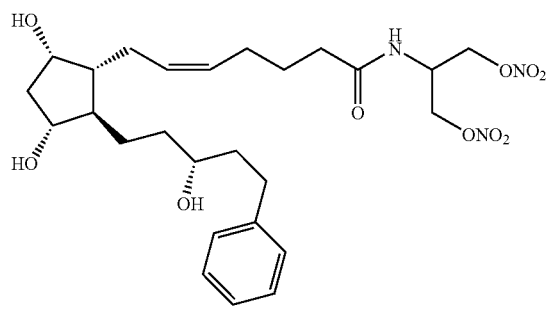
(109)
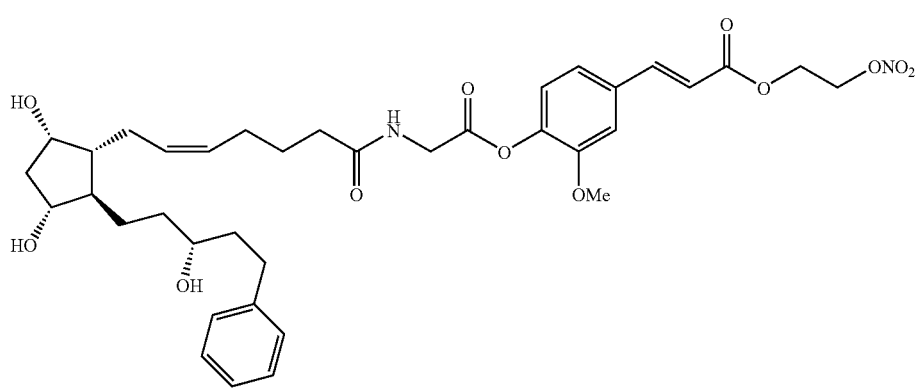
(110)
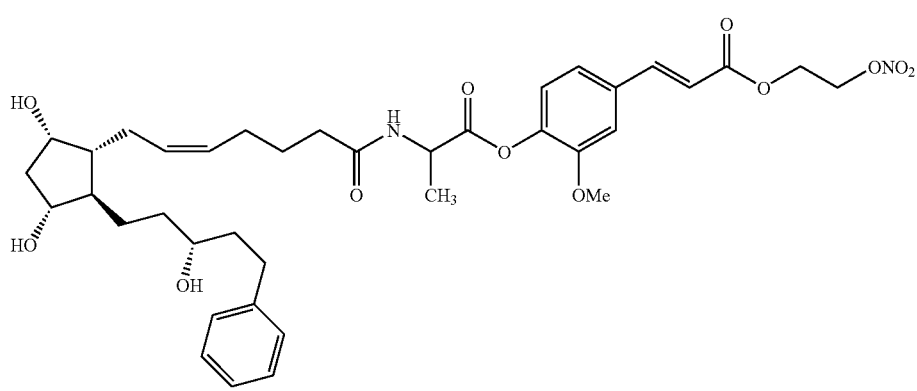
(111)
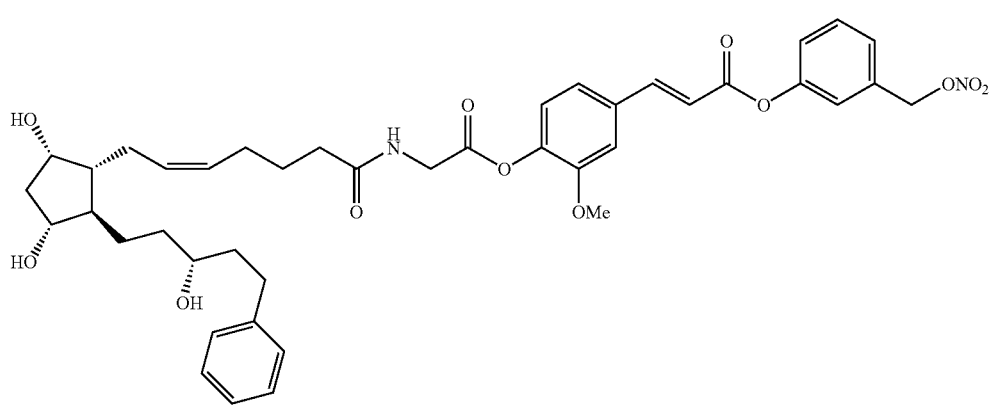

-continued
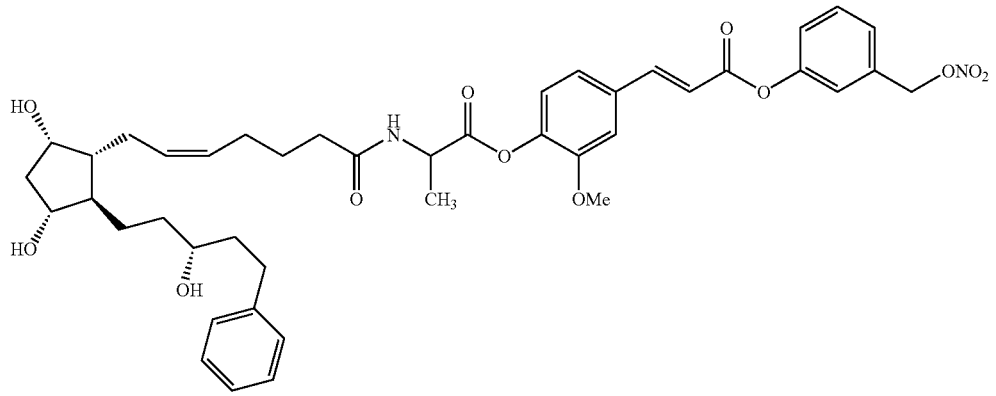
(112)
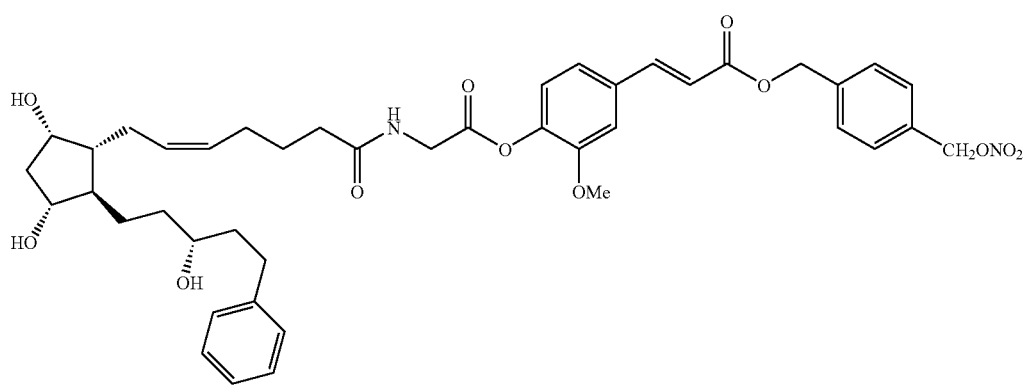
(113)
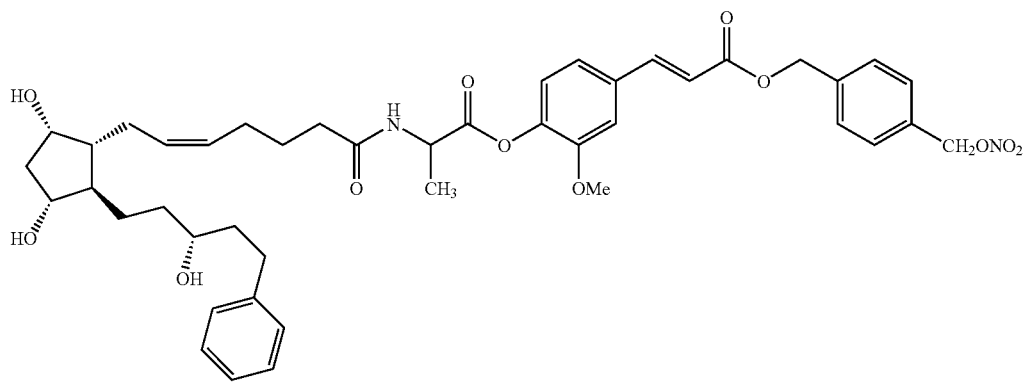
(114)
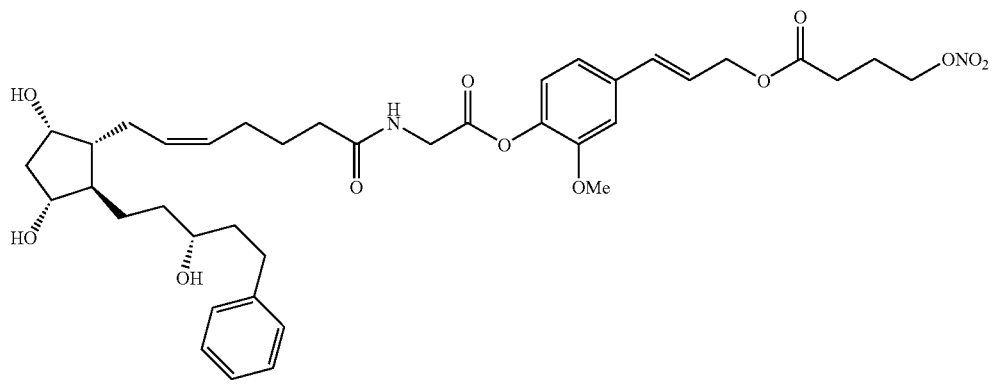
(115)

-continued
(116)
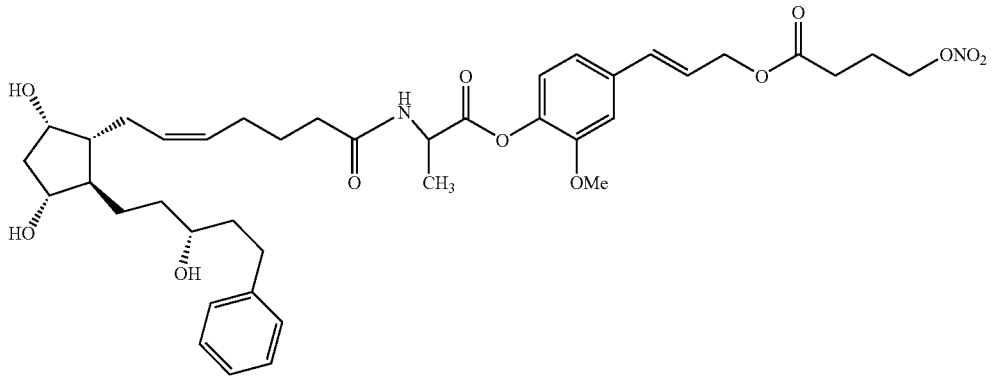
(117)
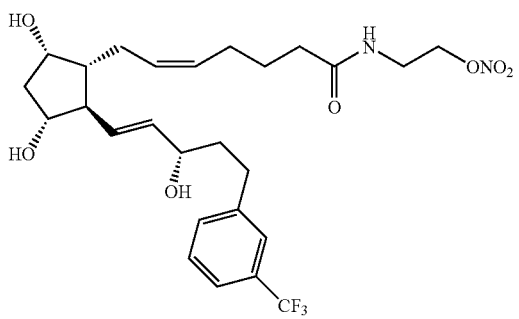
(118)
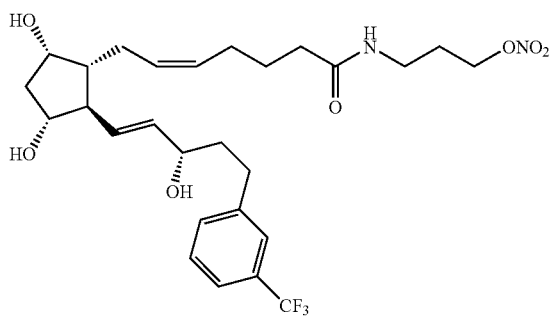
(119)
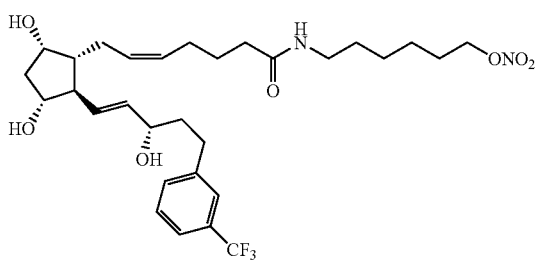
(120)
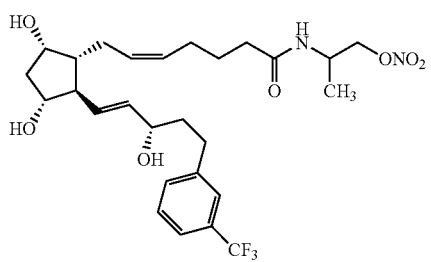
(121)
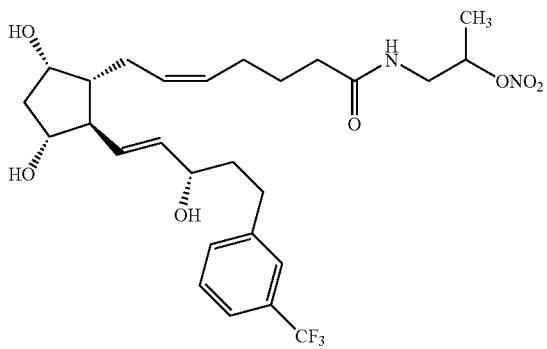
(122)
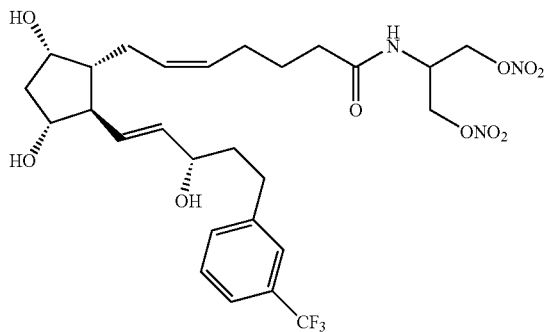

-continued
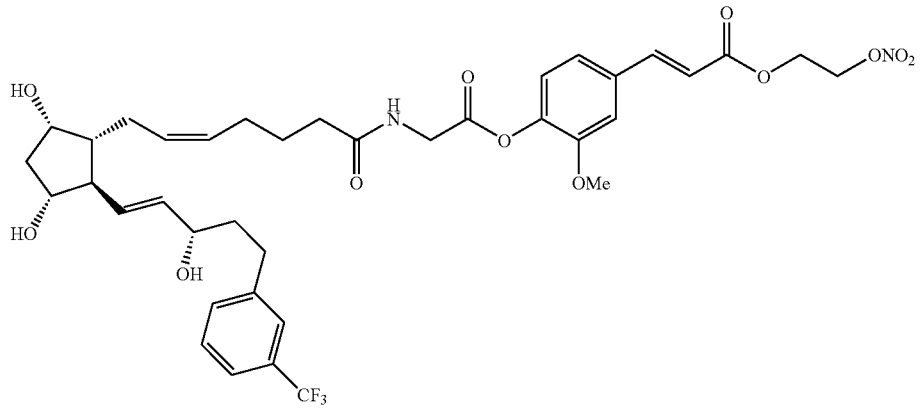
(123)
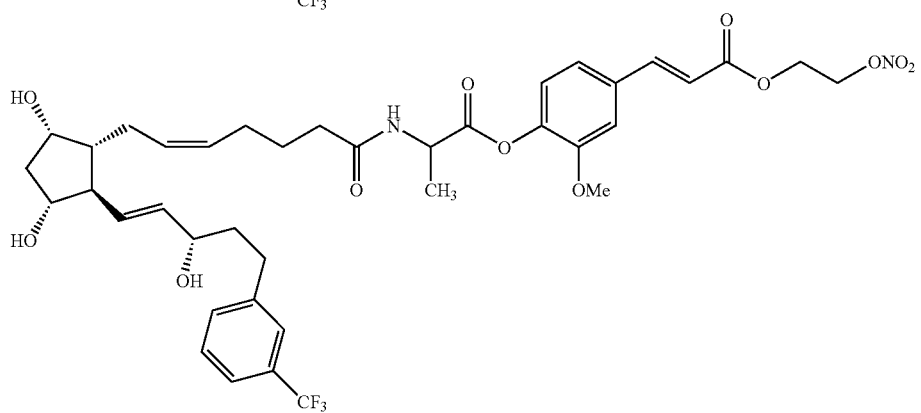
(124)
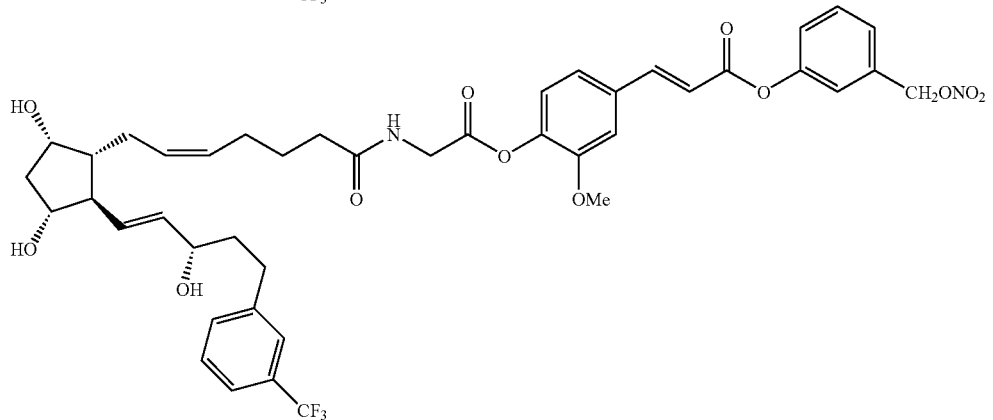
(125)
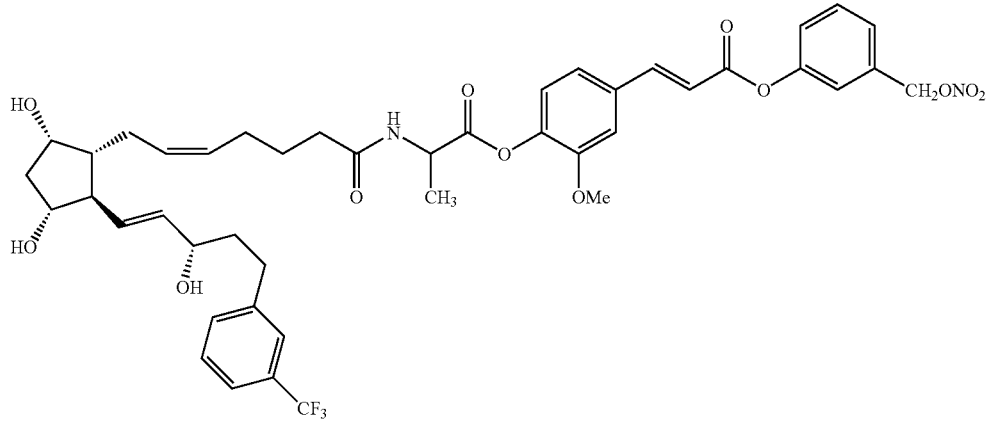
(126)

-continued
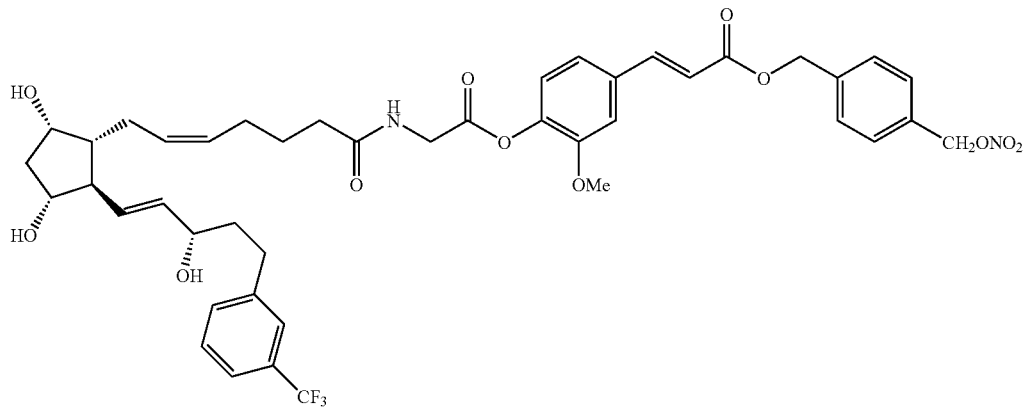
(127)
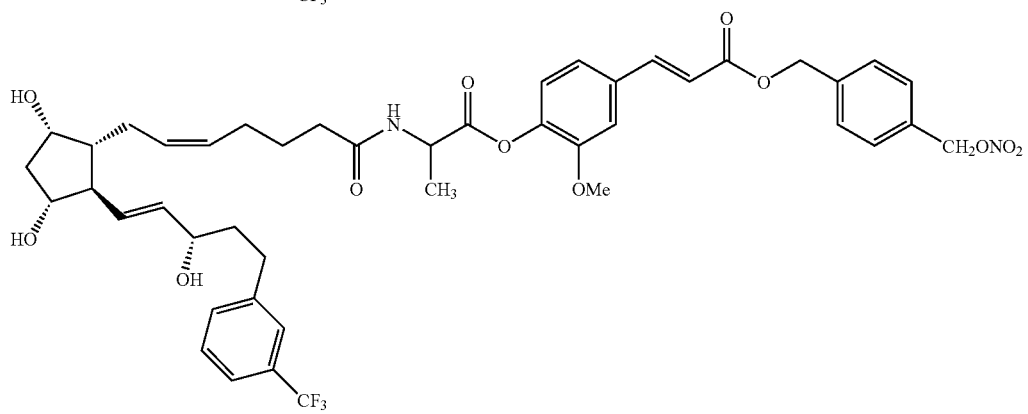
(128)
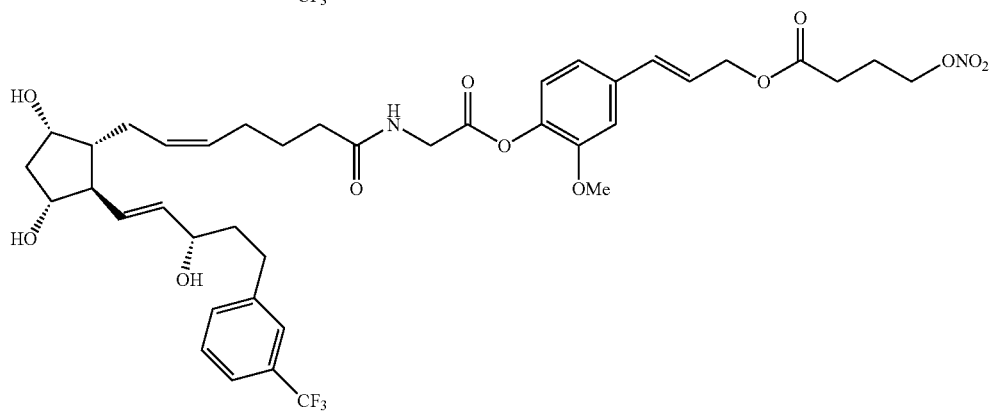
(129)
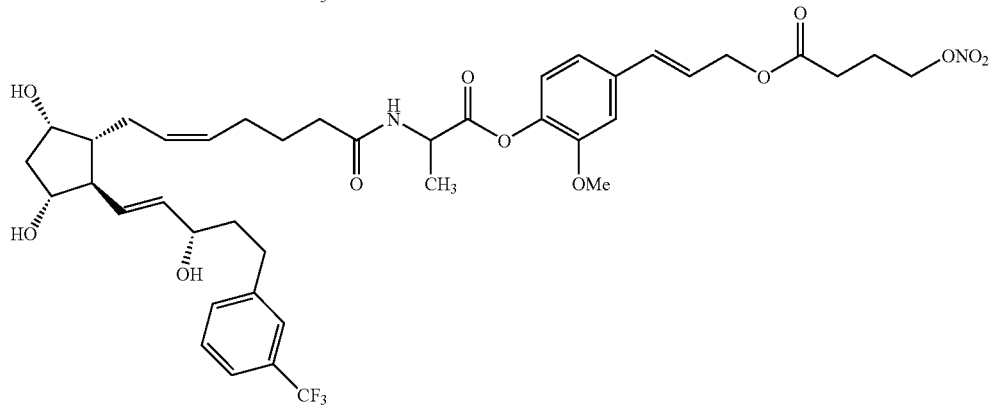
(130)

(131)
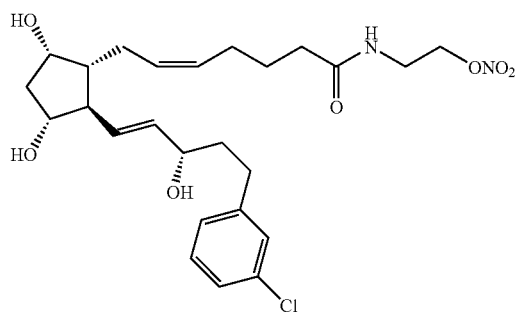
(132)
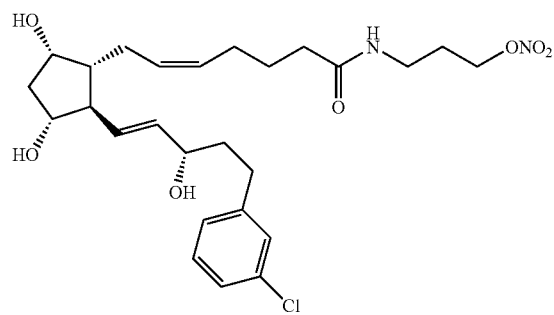
(133)
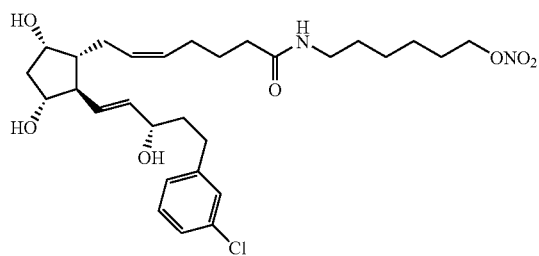
(134)
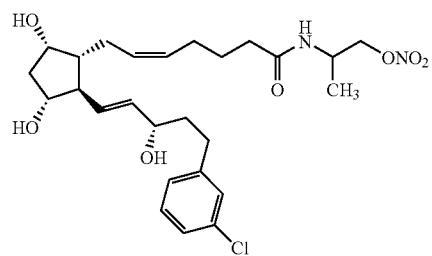
(135)
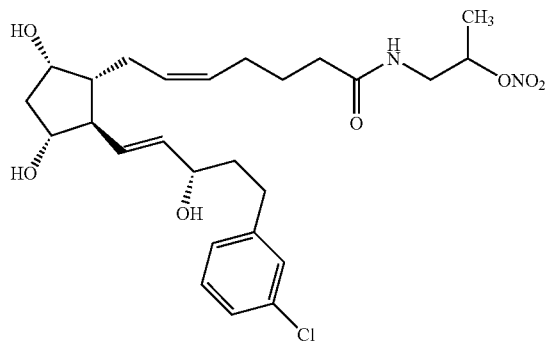
(136)
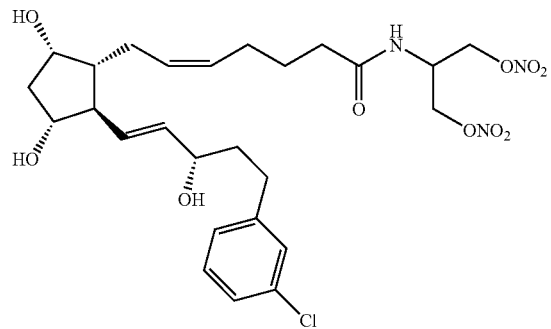
(137)
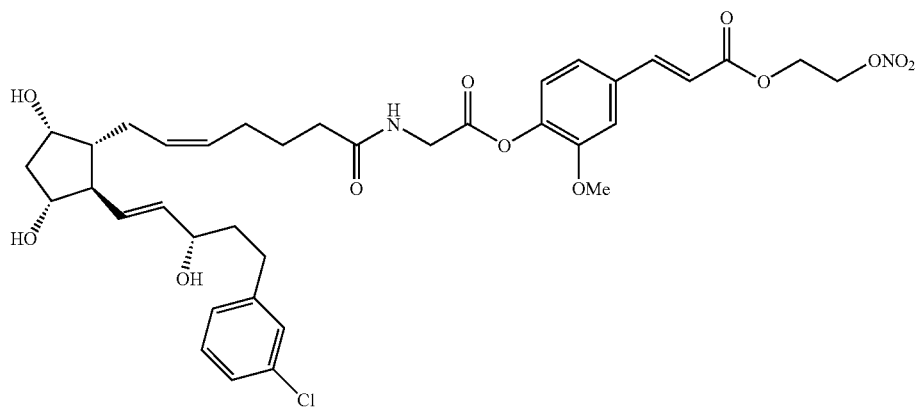

-continued
(138)
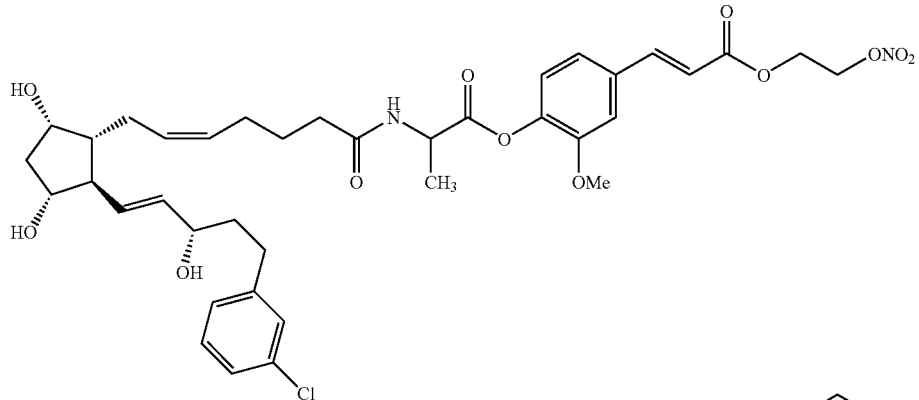
(139)
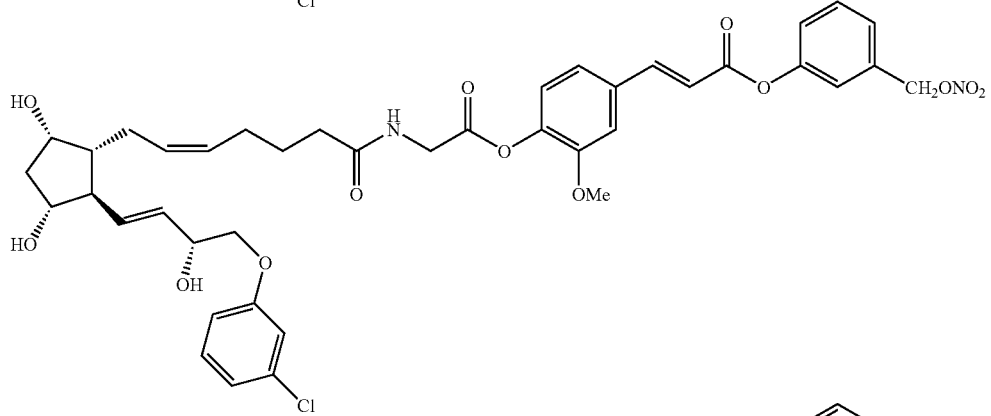
(140)
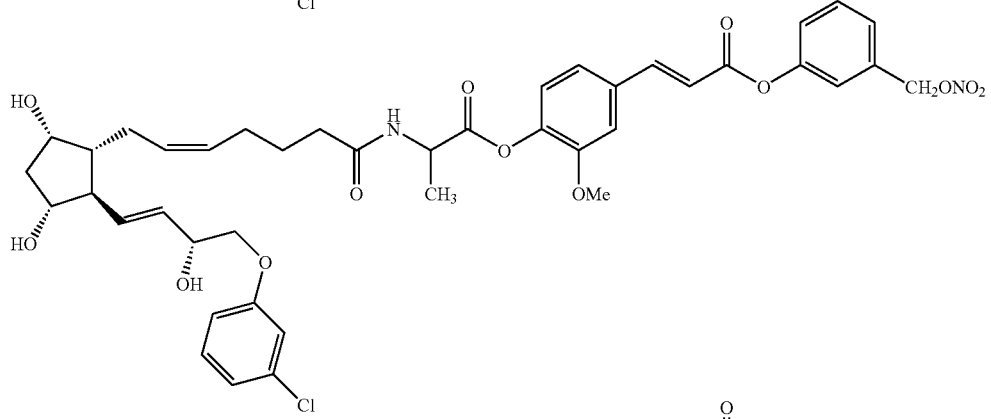
(141)
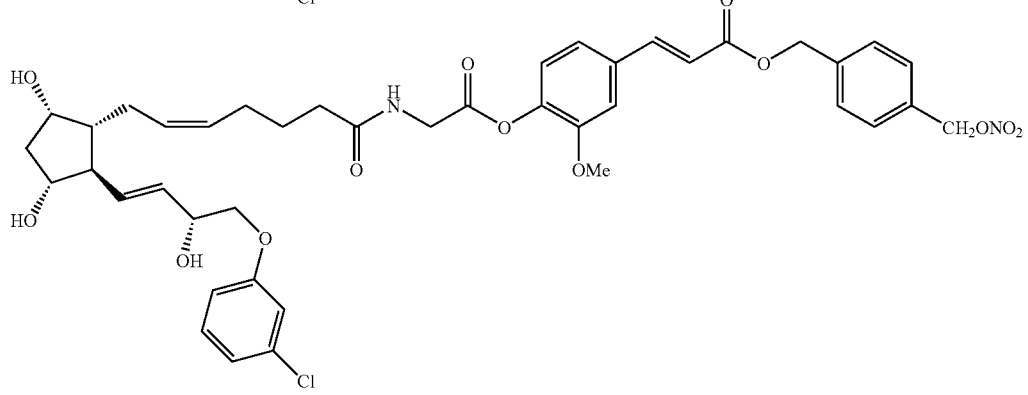

-continued
(142)
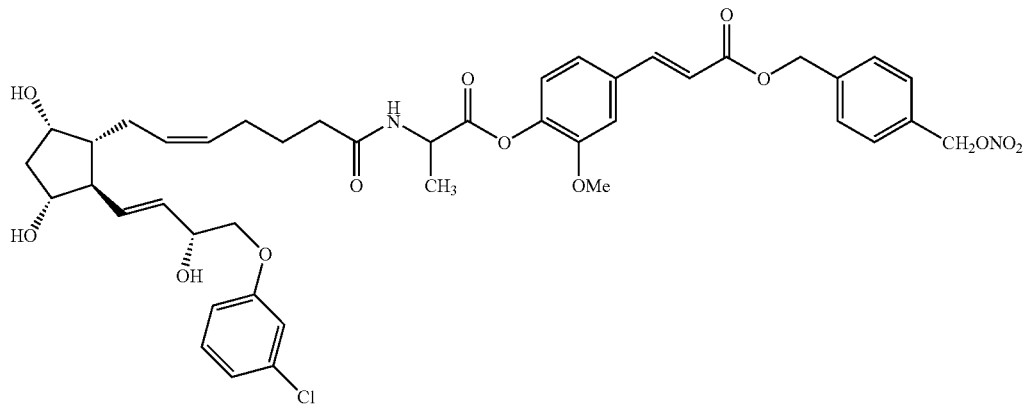
(143)
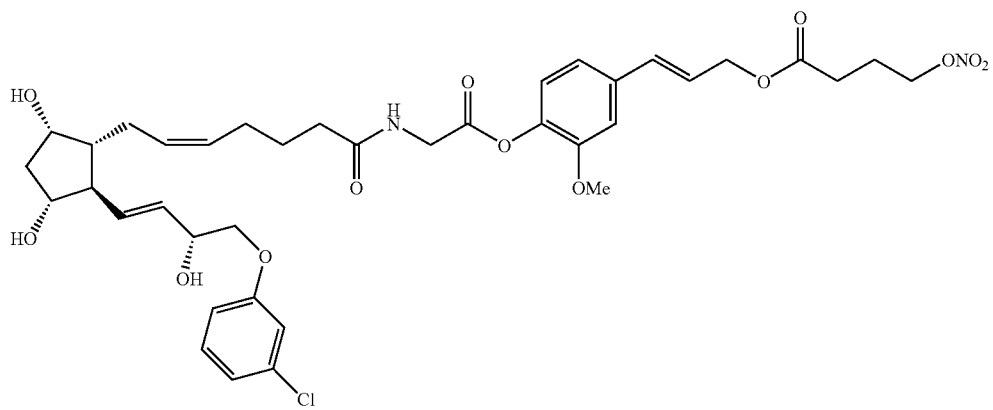
(144)
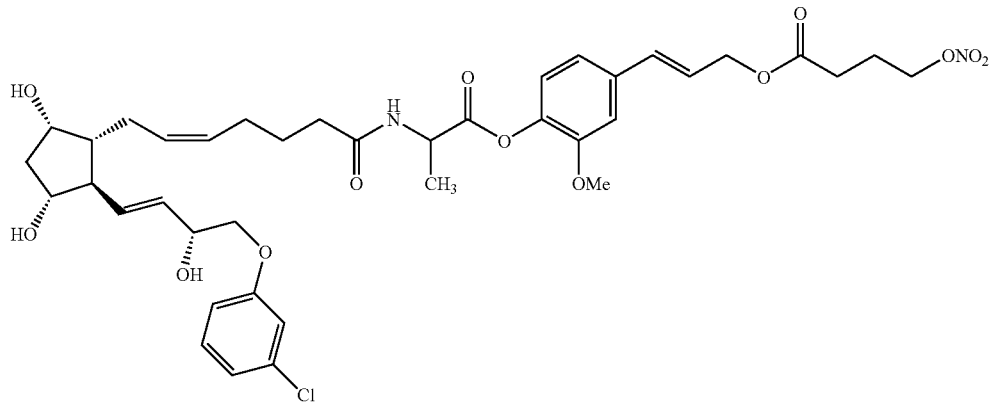
(145)
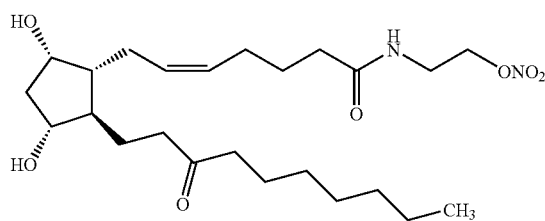
(146)
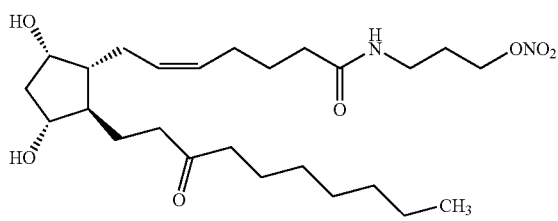

-continued
(147)
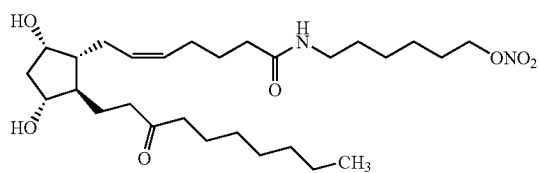
(148)
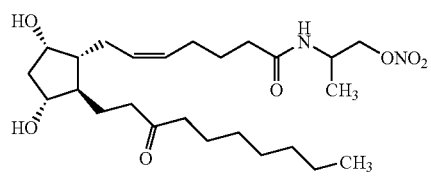
(149)
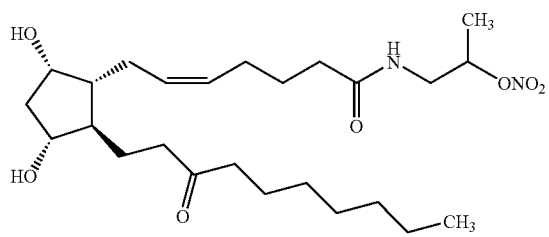
(150)
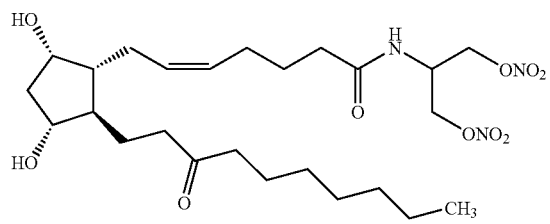
(151)
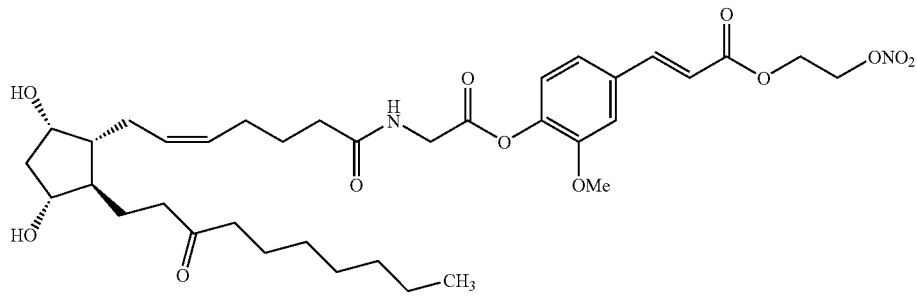
(152)
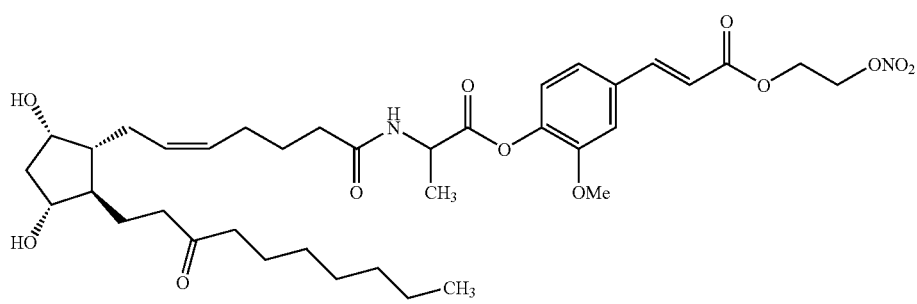
(153)
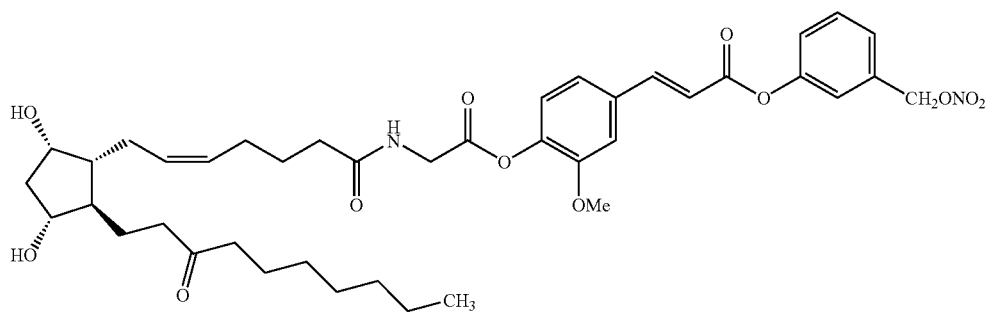

(154)
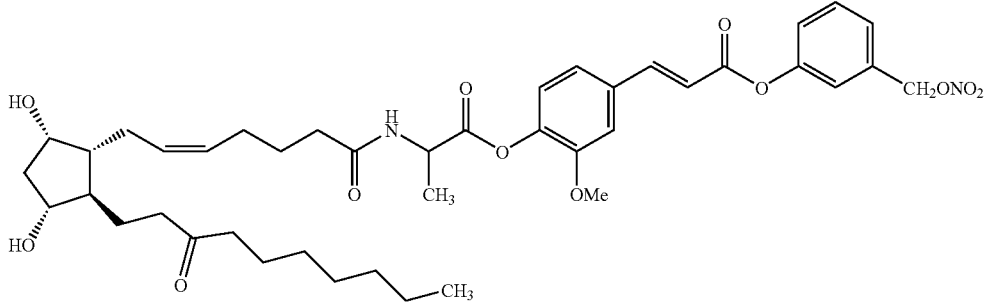
(155)
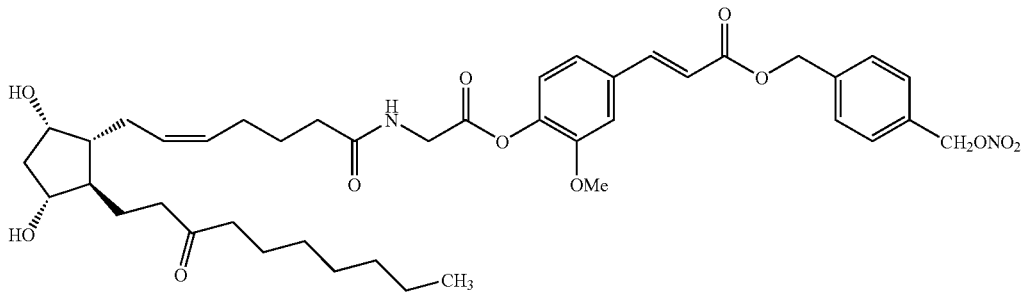
(156)
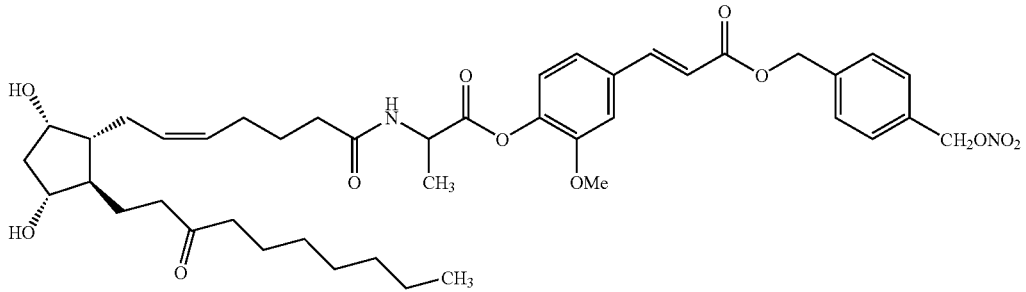
(157)
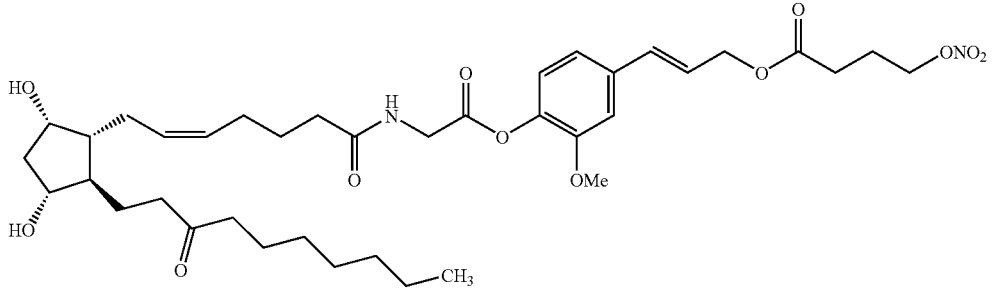
(158)
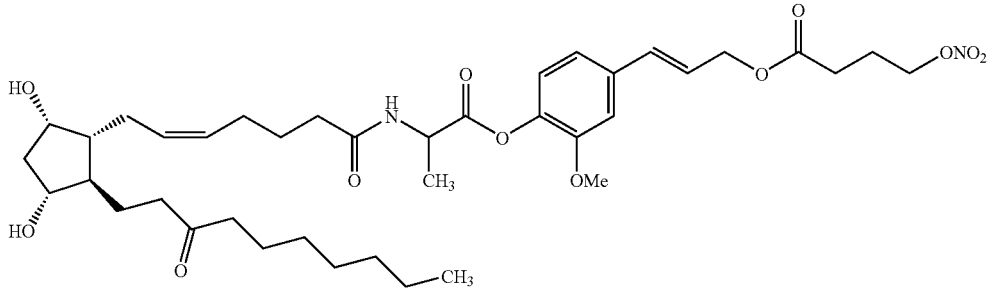

-continued
(159)
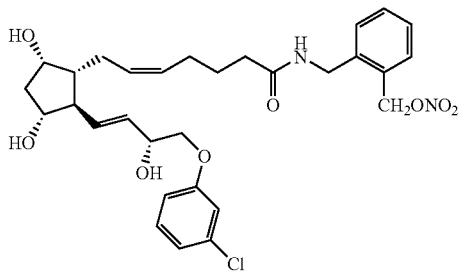
(160)
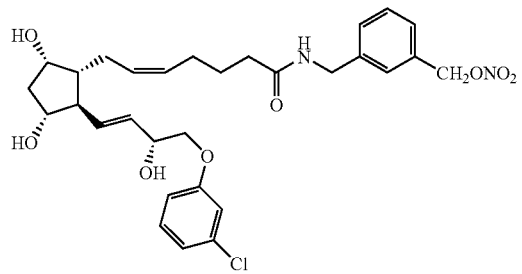
(161)
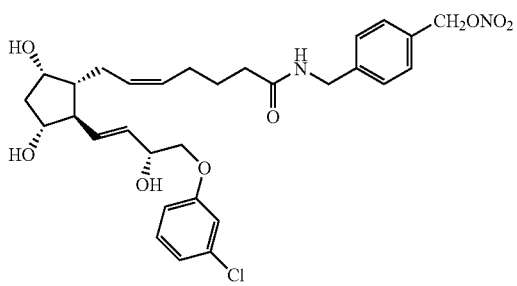
(162)
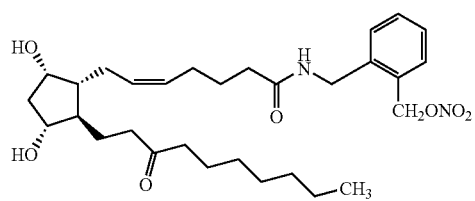
(163)
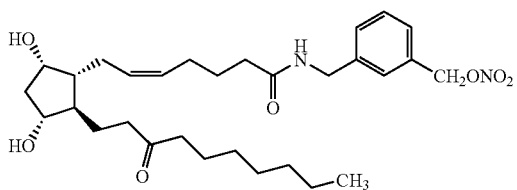
(164)
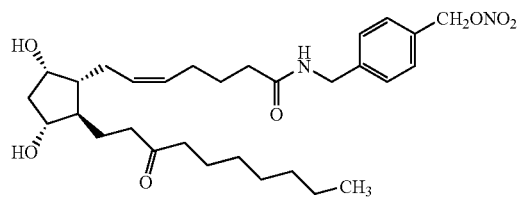
(165)
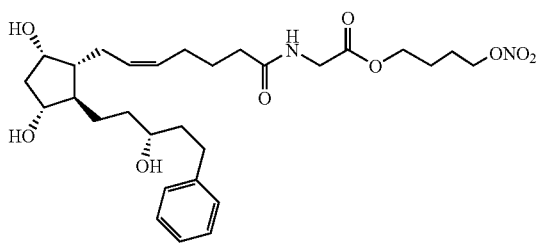
(166)
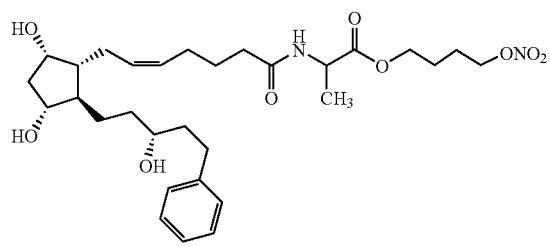
(167)
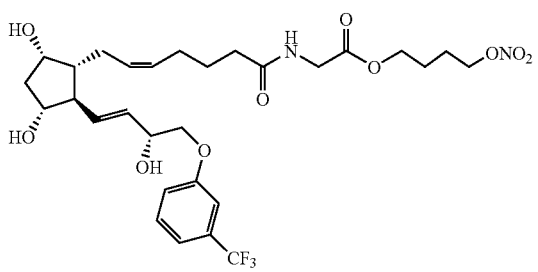
(168)
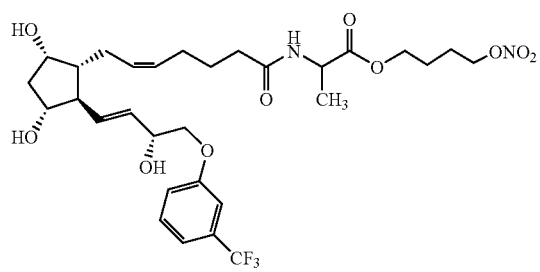

-continued
(169)
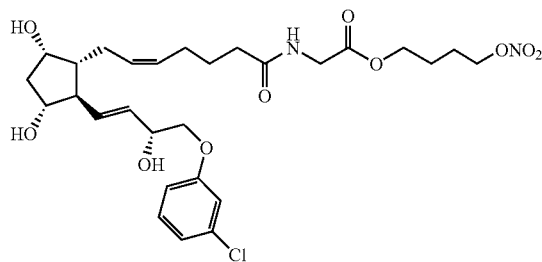
(170)
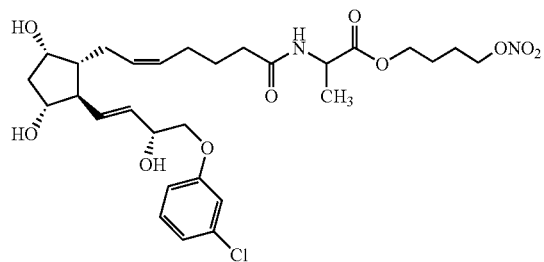
(171)
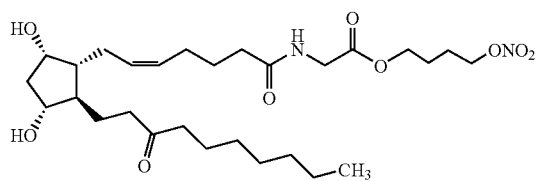
(172)
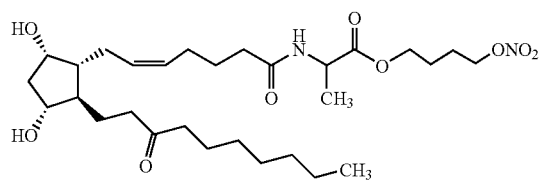
(173)
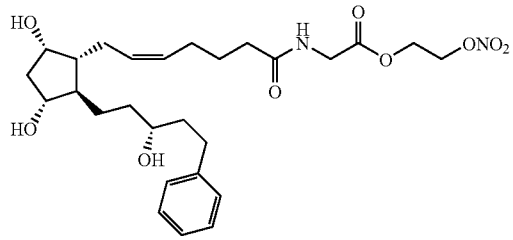
(174)
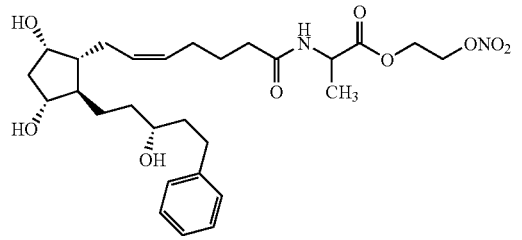
(175)
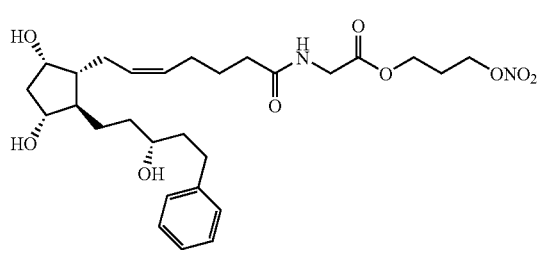
(176)
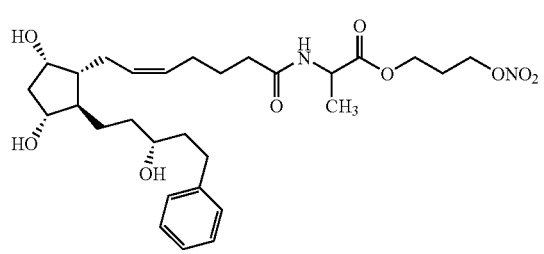
(177)
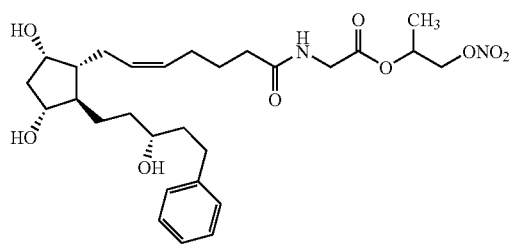
(178)
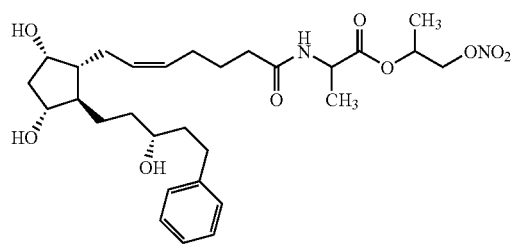
(179)
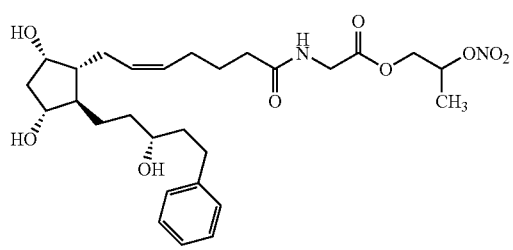
(180)
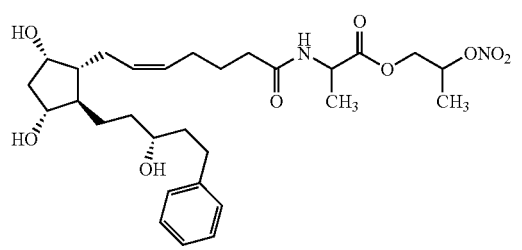

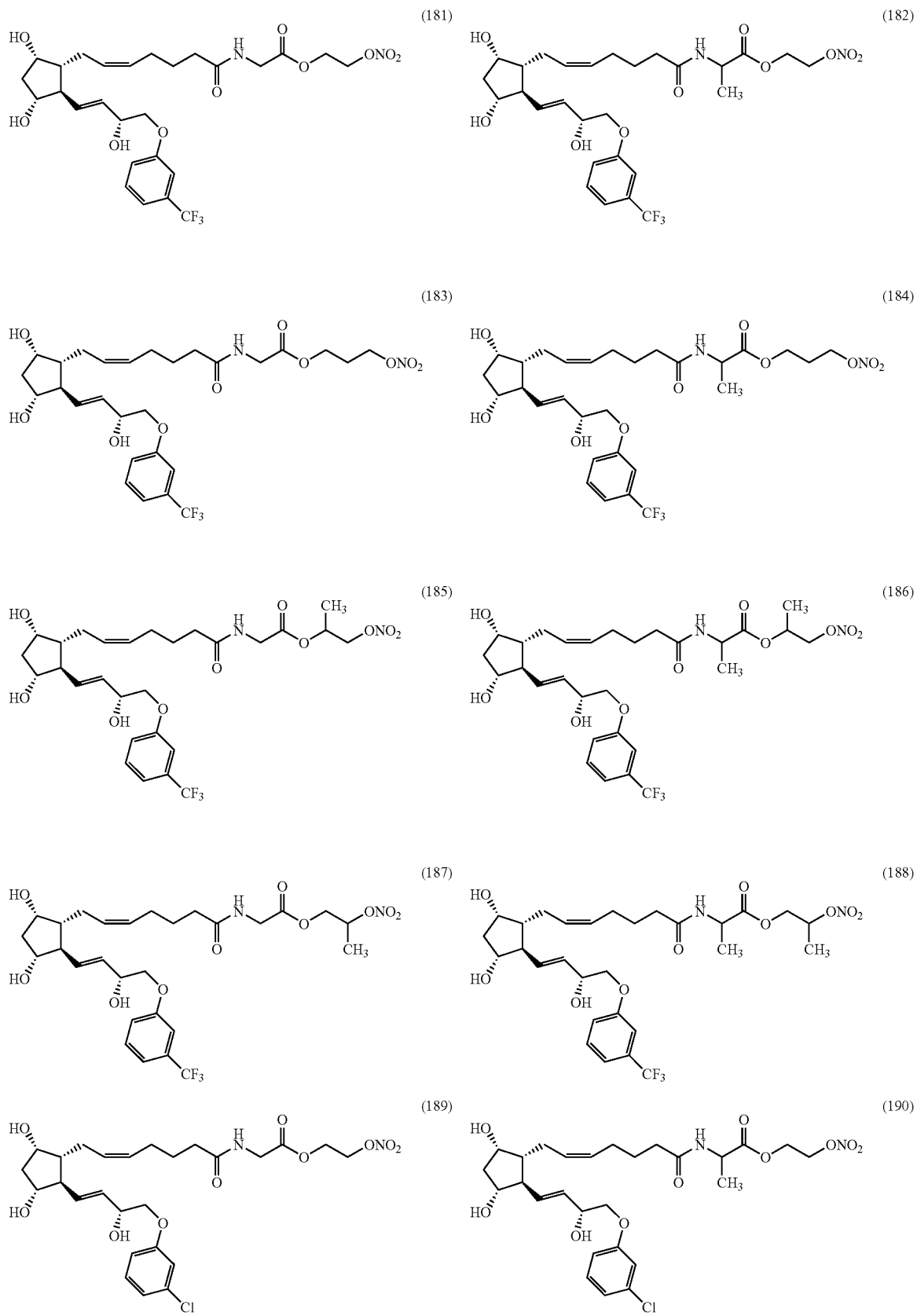

-continued
(191) 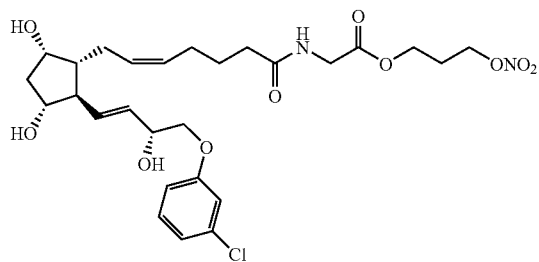
(192) 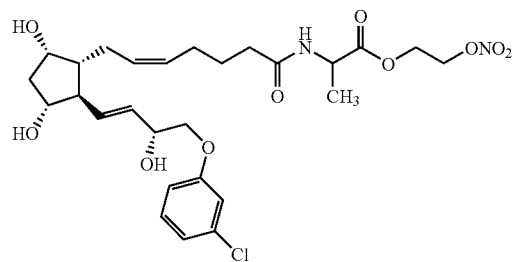
(193) 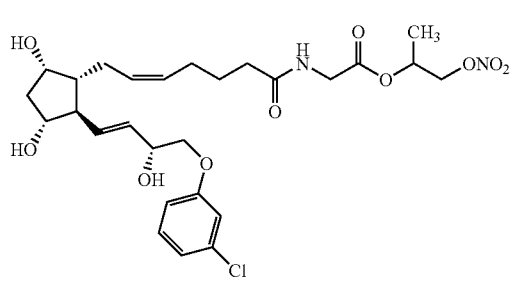
(194) 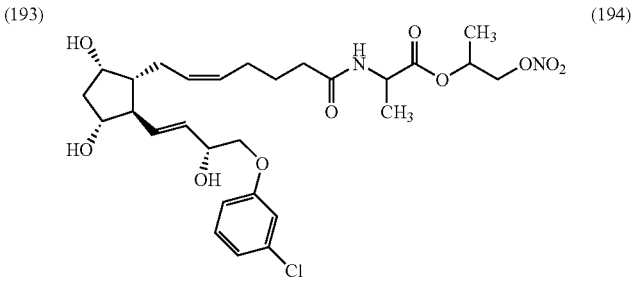
(195) 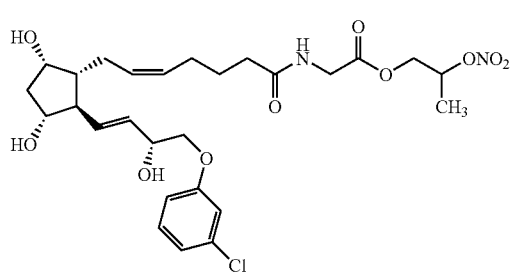
(196) 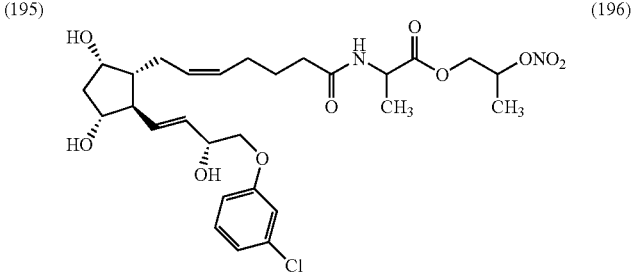
(197) 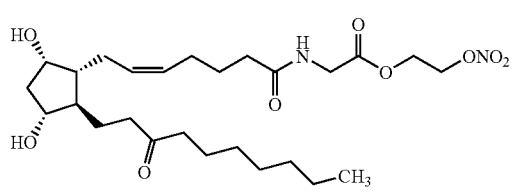
(198) 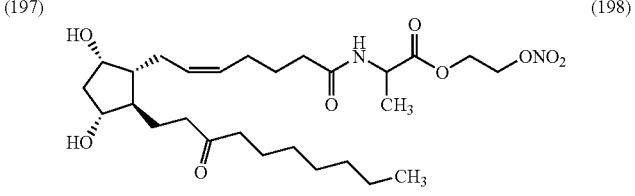
(199) 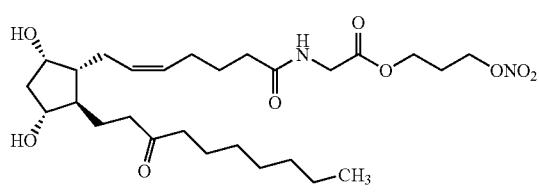
(200) 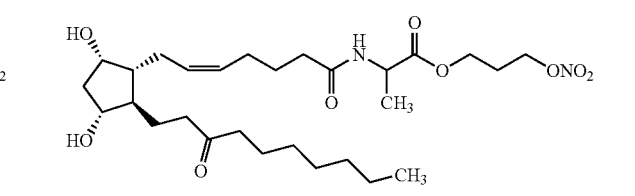
(201) 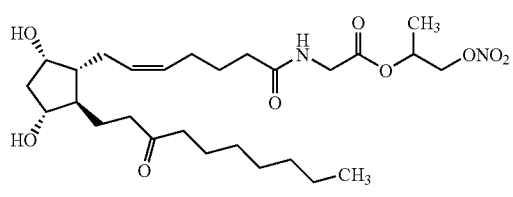
(202) 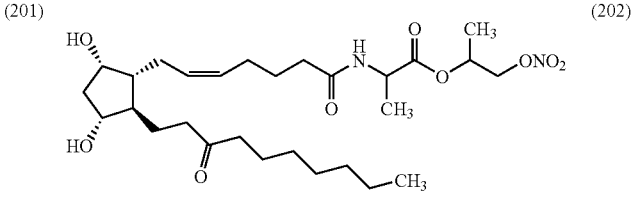
(203) 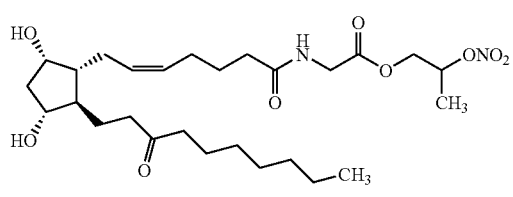
(204) 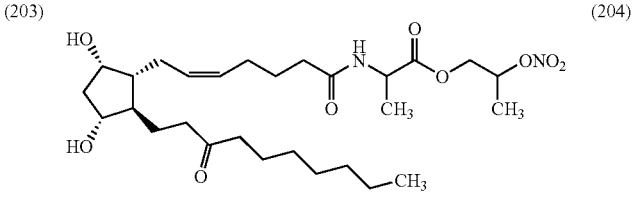

-continued
(205)
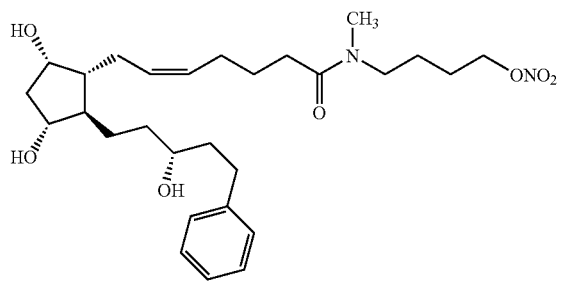
(206)
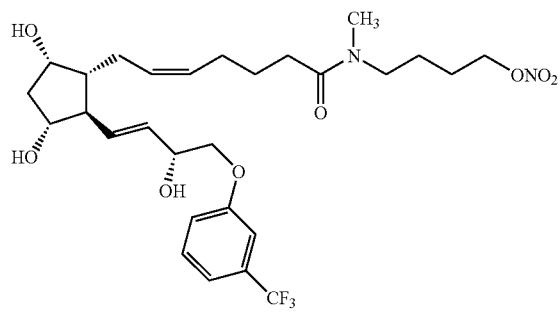
(207)
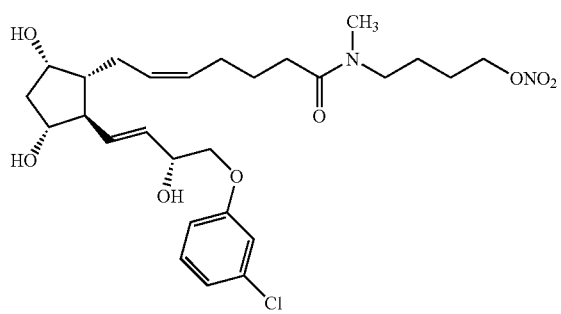
(208)
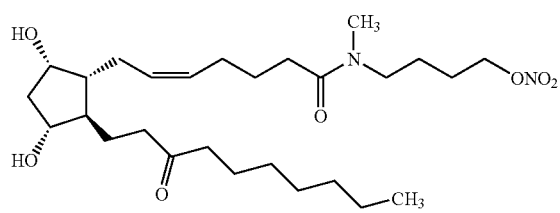
(209)
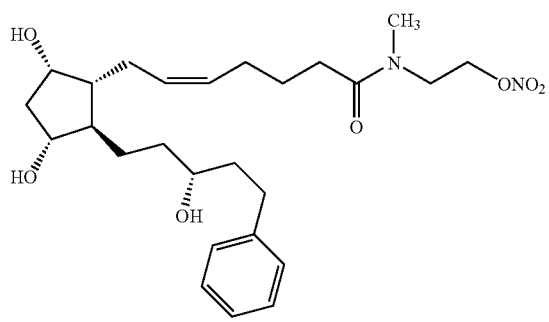
(210)
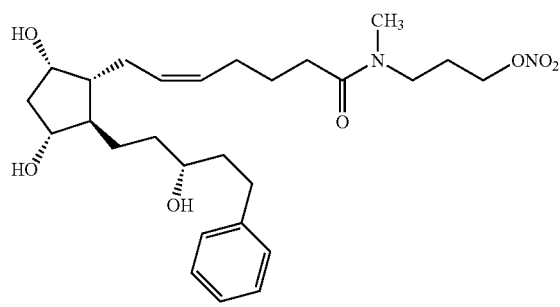
(211)
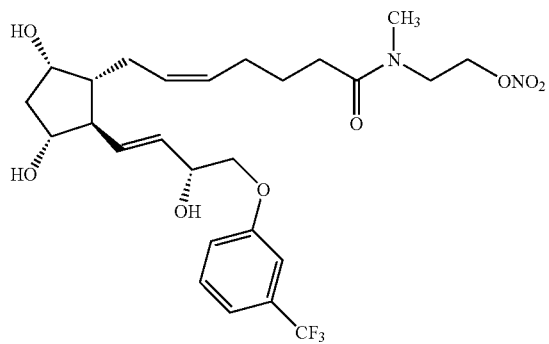
(212)
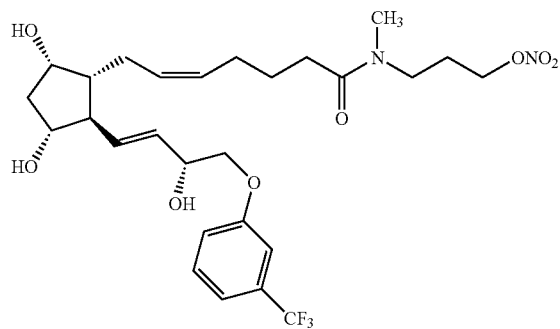

(213)

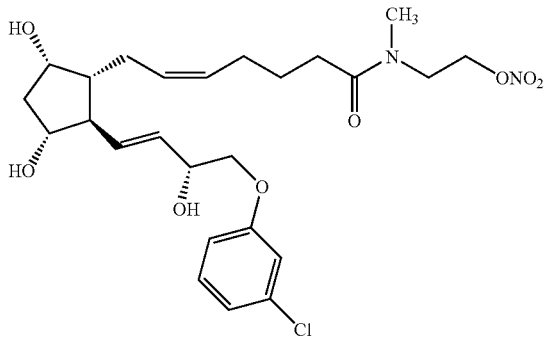

(214)

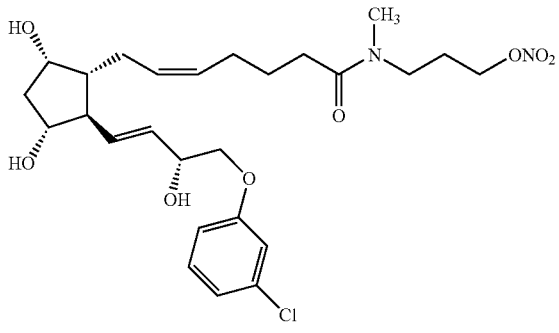

(215)

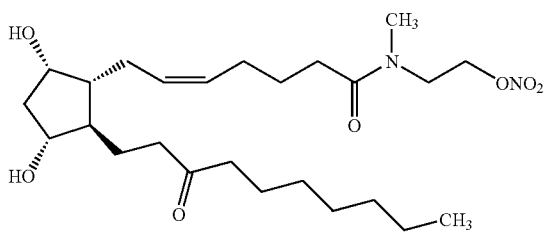

(216)

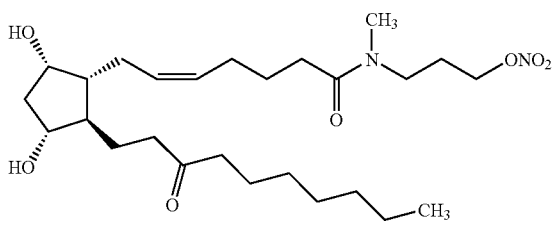

As stated above, the invention includes also the pharmaceutically acceptable salts of the compounds of formula (I) and stereoisomers thereof.

Examples of pharmaceutically acceptable salts are either those with inorganic bases, such as sodium, potassium, calcium and aluminium hydroxides, or with organic bases, such as lysine, arginine, triethylamine, dibenzylamine, piperidine and other acceptable organic amines.

The compounds according to the present invention, when they contain in the molecule one salifiable nitrogen atom, can be transformed into the corresponding salts by reaction in an organic solvent such as acetonitrile, tetrahydrofuran with the corresponding organic or inorganic acids.

Examples of organic acids are: oxalic, tartaric, maleic, succinic, citric acids. Examples of inorganic acids are: nitric, hydrochloric, sulphuric, phosphoric acids. Salts with nitric acid are preferred.

The compounds of the invention which have one or more asymmetric carbon atoms can exist as optically pure enantiomers, pure diastereomers, enantiomers mixtures, diastereomers mixtures, enantiomer racemic mixtures, racemates or racemate mixtures. Within the scope of the invention are also all the possible isomers, stereoisomers and their mixtures of the compounds of formula (I), including mixtures enriched in a particular isomer.

As mentioned above, objects of the present invention are also pharmaceutical compositions containing at least a compound of the present invention of formula (I) together with non toxic adjuvants and/or carriers usually employed in the pharmaceutical field.

The preferred route of administration is topical. The compounds of the present invention can be administered as solutions, suspensions or emulsions (dispersions) in an ophthalmically acceptable vehicle. The term "ophthalmically acceptable vehicle" as used herein refers to any substance or combination of substances which are non-reactive with the compounds and suitable for administration to patient.

Preferred are aqueous vehicles suitable for topical application to the patient's eyes.

Other ingredients which may be desirable to use in the ophthalmic compositions of the present invention include antimicrobials, preservatives, co-solvents, surfactants and viscosity building agents.

The invention also relates to a method for treating glaucoma or ocular hypertension, said method consisting in contacting an effective intraocular pressure reducing amount of a composition with the eye in order to reduce eye pressure and to maintain said pressure on a reduced level.

The doses of prostaglandin nitroderivatives can be determined by standard clinical techniques and are in the same range or less than those described for the corresponding underivatized, commercially available prostaglandin compounds as reported in the: Physician's Desk Reference, Medical Economics Company, Inc., Oradell, N.J., 58th Ed., 2004; The pharmacological basis of therapeutics, Goodman and Gilman, J. G. Hardman, L. e. Limbird, Tenth Ed.

The compositions contain 0.1-0.30 µg, especially 1-10 µg, per application of the active compound.

The treatment may be advantageously carried out in that one drop of the composition, corresponding to about 30 µl, is administered about 1 to 2 times per day to the patient's eye.

It is further contemplated that the compounds of the present invention can be used with other medicaments known to be useful in the treatment of glaucoma or ocular hypertension, either separately or in combination. For example the compounds of the present invention can be combined with (i) beta-blockers, such as timolol, betaxolol, levobunolol and the like (see U.S. Pat. No. 4,952,581); (ii) carbonic anhydrase inhibitors, such as brinzolamide; (iii) adrenergic agonists including clonidine derivatives, such as apraclonidine or brimonidine (see U.S. Pat. No. 5,811,443). Also contemplated is the combination with nitrooxy derivatives of the above reported compounds, for example nitrooxy derivatives of beta-blockers such as those described in U.S. Pat. No. 6,242,432.

The compounds of general formula (I) as above defined, can be obtained by a process comprising the following steps:
a) reacting a compound of formula (III)

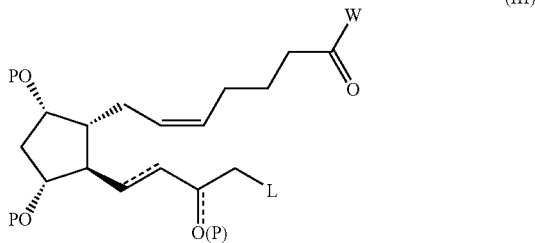

wherein
L is as above defined; P is H or a hydroxylic protecting group, W is —OH, Cl, or —OC(O)$R_1$ wherein $R_1$ is a linear or branched $C_1$-$C_5$ alkyl;
with a compound of formula (IV)

wherein $R^1$, Y, B and m are as above defined, Q is —$ONO_2$ or $Z_1$ wherein $Z_1$ is selected from the group consisting of: chlorine, bromine, iodine, mesyl, tosyl; and
b) when Q is $Z_1$, converting the compound obtained in the step a) into the corresponding nitro derivative by reaction with a nitrate source; and
c) optionally deprotecting the compound obtained in step a) or b).

Step a
Preferred hydroylic protecting groups are silyl ethers, such as trimethylsilyl, tert-butyl-dimethylsilyl, or acetyl and those described in T. W. Greene 'Protective groups in organic synthesis', Harvard University Press, 1980;
The reaction of a compound of formula (III) wherein W=—OH, P and L are as above defined, with a compound of formula (IV) wherein Q, Y, B, $R^1$ and m are as above defined may be carried out in presence of a condensing agent as dicyclohexylcarbodiimide (DCC), N'-(3-dimethylaminopropyl)-N-ethylcarbodiimide hydrochloride (EDAC) and a catalyst, such as N,N-dimethylamino pyridine (DMAP) or N,N'-carbonyldiimidazole (CDI). The reaction is carried out in an inert organic solvent dry such as N,N'-dimethylformamide, tetrahydrofuran, benzene, toluene, dioxane, a polyhalogenated aliphatic hydrocarbon at a temperature from −20° C. and 40° C. The reaction is completed within a time range from 30 minutes to 36 hours.
The reaction of a compound of formula (III) wherein W=—OC(O)$R^1$ wherein $R_1$ and P are as above defined, with a compound of formula (IV) wherein Q, Y, B, $R^1$ and m are as above defined may be carried out in presence of a catalyst, such as N,N-dimethylamino pyridine (DMAP). The reaction is carried out in an inert organic solvent such as N,N'-dimethylformamide, tetrahydrofuran, benzene, toluene, dioxane, a polyhalogenated aliphatic hydrocarbon at a temperature from −20° C. and 40° C. The reaction is completed within a time range from 30 minutes to 36 hours.
The reaction of a compound of formula (III) wherein W=Cl and P is as above defined, with a compound of formula (IV) wherein Q, Y, B, $R^1$ and m are as above defined may be carried out in presence of an organic base such as N,N-dimethylamino pyridine (DMAP), triethylamine, pyridine. The reaction is carried out in an inert organic solvent such as N,N'-dimethylformamide, tetrahydrofuran, benzene, toluene, dioxane, a polyhalogenated aliphatic hydrocarbon at a temperature from −20° C. and 40° C. The reaction is completed within a time range from 30 minutes to 36 hours.

Step b)
A nitrate source may be silver nitrate, lithium nitrate, sodium nitrate, potassium nitrate, magnesium nitrate, calcium nitrate, iron nitrate, zinc nitrate or tetraalkylammonium nitrate (wherein alkyl is $C_1$-$C_{10}$ alkyl. Preferred nitrate source is silver nitrate. The reaction of step b) is carried out preferably in the dark, in a suitable organic solvent such as acetonitrile, tetrahydrofurane, methyl ethyl ketone, ethyl acetate, DMF, at a temperature from room temperature to the boiling temperature of the solvent.

Step C
The reaction of step C) may be carried out as described in T. W. Greene "Protective groups in organic synthesis", Harvard University Press, 1980. The reaction with fluoride ion is the preferred method for removing silyl ether protecting group.
The compounds of formula (III) wherein W=—OH and P=H are commercially available;
The compounds of formula (III) wherein W=—OH and P is a hydroxylic protecting group may be prepared from the corresponding compounds wherein P=H as well known in the art, for example as described in T. W. Greene "Protective groups in organic synthesis", Harvard University Press, 1980.
The compounds of formula (III) wherein W=—OC(O)$R_1$ and P is as above defined may be obtained from the corresponding acids wherein W=—OH by reaction with a chloroformate such as isobutylchloroformate, ethylchloroformate in presence of a non-nucleophilic base such as triethylamine in an inert organic solvent such as N,N'-dimethylformamide, tetrahydrofuran, a polyhalogenated aliphatic hydrocarbon at a temperature from −20° C. and 40° C. The reaction is completed within a time range from 1 to 8 hours.
The compounds of formula (III) wherein W=Cl may be obtained from the corresponding acids wherein W=—OH by reaction with a thionyl or oxalyl chloride, halides of $P^{III}$ or $P^V$ in solvents inert such as toluene, chloroform, DMF.
The compounds of formula (IV), wherein Q is $Z_1$, Y, B, $R^1$ are as above defined and m=0 can be obtained by reacting a compound of formula (IV$_a$)

with a suitable reagent such as thionyl or oxalyl chloride, halides of $P^{III}$ or $P^V$, mesyl chloride, tosyl chloride in an inert solvent such as toluene, chloroform, DMF, etc.
The compounds of formula (IV), wherein Q is —$ONO_2$, $Z_1$, Y, B, $R^1$ are as above defined and m=0 are obtained by convertion of the above compounds of formula (IV$_a$) as above described in step b). Alternatively the nitration can be carried out in the presence of nitric acid and acetic anhydride in a temperature range from −50° C. to 0° C. according to methods well known in the literature.
The compounds of formula (IV) wherein $R^1$, Q, Y, B, Z are as above defined and m=1 can be obtained by a process comprising the following steps:
a) reacting a compound of formula (V)

wherein W is as above defined, $B_1$ is a radical of the formula —CH($R^1$)CO—, wherein $R^1$ is as above defined, $P_1$ is H or a amino protecting group such as tert-butylcarbamate (BOC), 2,2,2-trichloroethyl carbamate (TROC) and those described in T. W. Greene "Protective groups in organic synthesis", Harvard University Press, 1980, with a compound of formula (VI)

$$Z_3\text{-Y-Q} \tag{VI}$$

wherein Y and Q are as above defined, $Z_3$ is HO or $Z_1$, and optionally deprotecting the obtained compounds as described in T. W. Greene "Protective groups in organic synthesis", Harvard University Press, 1980; and b) when Q is $Z_1$, converting the compound obtained in the step a) into a nitro derivative by the procedure above described.

The reaction of a compound of formula (V) wherein W=—OH, with a compound of formula (VI) $Z_3$-Y-Q wherein $Z_3$ is —OH, Y and Q are as above defined, may be carried out in presence of a dehydrating agent as dicyclohexylcarbodiimide (DCC) or N'-(3-dimethylaminopropyl)-N-ethylcarbodiimide hydrochloride (EDAC) and a catalyst, such as N,N-dimethylamino pyridine (DMAP). The reaction is carried out in an inert organic solvent dry such as N,N'-dimethylformamide, tetrahydrofuran, benzene, toluene, dioxane, a polyhalogenated aliphatic hydrocarbon at a temperature from −20° C. and 40° C. The reaction is completed within a time range from 30 minutes to 36 hours.

The compounds of formula (V) wherein W=—OH are commercially available or can be synthesized according to methods well known in the literature.

The reaction of a compound of formula (V) wherein W=—OC(O)$R_1$ wherein $R_1$ is as above defined with a compound of formula (VI) $Z_3$-Y-Q wherein $Z_3$ is —OH, Y and Q are as above defined, may be carried out in presence of a catalyst, such as N,N-dimethylamino pyridine (DMAP). The reaction is carried out in an inert organic solvent such as N,N'-dimethylformamide, tetrahydrofuran, benzene, toluene, dioxane, a polyhalogenated aliphatic hydrocarbon at a temperature from −20° C. and 40° C. The reaction is completed within a time range from 30 minutes to 36 hours.

The compounds of formula (V) wherein W=—OC(O)$R^1$ may be obtained from the corresponding acids wherein W=—OH by reaction with a chloroformate such as isobutylchloroformate, ethylchloroformate in presence of a non-nucleophilic base such as triethylamine in an inert organic solvent such as N,N'-dimethylformamide, tetrahydrofuran, a polyhalogenated aliphatic hydrocarbon at a temperature from −20° C. and 40° C. The reaction is completed within a time range from 1 to 8 hours.

The reaction of a compound of formula (V) wherein W=—OH, with a compound of formula (VI) $Z_3$-Y-Q wherein $Z_3$ is $Z_1$, Y and Q are as above defined, may be carried out in presence of a organic base such as 1,8-diazabiciclo[5.4.0]undec-7-ene (DBU), N,N-diisopropylethylamine, diisopropylamine or inorganic base such as alkaline-earth metal carbonate or hydroxide, potassium carbonate, cesium carbonate, in an inert organic solvent such as N,N'-dimethylformamide, tetrahydrofuran, acetone, methyl ethyl ketone, acetonitrile, a polyhalogenated aliphatic hydrocarbon at a temperature from −20° C. and 40° C., preferably from 5° C. to 25° C. The reaction is completed within a time range from 1 to 8 hours. When $Z_1$ is chosen among chlorine or bromine the reaction is carried out in presence an iodine compound such as KI.

The reaction of a compound of formula (V) wherein W=Cl with a compound of formula (VI) $Z_3$-Y-Q wherein $Z_3$ is —OH, Y and Q are as above defined, may be carried out in presence of a of a organic base such as N,N-dimethylamino pyridine (DMAP), triethylamine, pyridine. The reaction is carried out in an inert organic solvent such as N,N'-dimethylformamide, tetrahydrofuran, benzene, toluene, dioxane, a polyhalogenated aliphatic hydrocarbon at a temperature from −20° C. and 40° C. The reaction is completed within a time range from 30 minutes to 36 hours.

The compounds of formula (V) wherein W=Cl may be obtained from the corresponding acids wherein W=—OH by reaction with a thionyl or oxalyl chloride, halides of $P^{III}$ or $P^V$ in solvents inert such as toluene, chloroform, DMF.

The compounds of formula (VI) $Z_3$-Y-Q wherein $Z_3$ is —OH, Q is —ONO$_2$ and Y is as above defined can be obtained by converting the corresponding diol derivative of formula (VII)

$$HO\text{—Y—}OH \tag{VII}$$

wherein Y is as above defined, in a compound of formula (VIII)

$$Z_3\text{-Y-}Z_1 \tag{VIII}$$

wherein $Z_3$, Y, $Z_1$ are as above defined, by well known reactions, for example by reaction with thionyl or oxalyl chloride, halides of $P^{III}$ or $P^V$, mesyl chloride, tosyl chloride in solvents inert such as toluene, chloroform, DMF, etc. The final conversion to the nitro derivative is carried out as above described. Alternatively the diol derivative of formula (VII) can be nitrated by reaction with nitric acid and acetic anhydride in a temperature range from −50° C. to 0° C. according to methods well known in the literature.

Compounds of formula (VII) are commercially available, or can be synthesized by well known reactions.

The compounds of formula (VI) wherein $Z_3$ is $Z_1$, Q is —ONO$_2$ and Y and $Z_1$ are as above defined can be obtained from the halogen derivative of formula (IX)

$$Z_1\text{-Y-Hal} \tag{IX}$$

wherein Hal is halogen, by conversion to the nitro derivative following the methods above described.

Compounds of formula (IX) are commercially available or can be synthesized according to methods well known in the literature.

The following examples are to further illustrate the invention without limiting it.

EXAMPLE 1

Synthesis of [1R-[1α(Z),2β(R*),3α,5α]]-7-[3,5-dihydroxy-2-(3-hydroxy-5-phenylpentyl)cyclopentyl]-5-heptenoic acid 3-(nitrooxy)propyl amide (corresponding to compound 104)

A) [1R-[1α(Z),2β(R*),3α,5α]]-7-[3,5-di-TBDMSilyl-oxy-2-(3 TBDMSilyl-oxy-5-phenyl-pentyl)cyclopentyl]-5-heptenoic acid To a solution of latanoprost acid (1 g, 2.56 mmol) in dimethylformamide dry (12 ml), TBDMSiCl (4.6 g, 30.72 mmol) and imidazole (2.1 g, 30.72 mmol) were added. The reaction was stirred at room temperature for 24 hours. The solution was treated with KHSO$_4$ and extracted three times with AcOEt. The organic layers were washed with brine, dried with sodium sulfate and concentrated under reduced pressure. The residue was purified by flash chromatography, eluent n-hexane/ethyl acetate 8/2. The product (1.3 g) was obtained as an oil.

B) [1R-[1α(Z),2β(R*),3α,5α]]-7-[3,5-di-TBDMSi-lyl-oxy-2-(3-TBDMSilyl-oxy-5-phenyl-pentyl)cyclopentyl]-5-heptenoic acid 3-bromopropylamide To a suspension of 3-bromopropylamine hydrobromide (0.12 g, 0.55 mmol) in $CH_2Cl_2$ (50 ml), TEA (0.55 mg, 0.55 mmol) was added. After 30 min compound A (0.2 g, 0.27 mmol), EDAC (0.77 g, 0.40 mmol) and DMAP (cat. amount) were added and the reaction was stirred at room temperature for 4 hours. The solution was washed with water and the organic layers were dried with sodium sulfate and concentrated under reduced pressure. The residue was purified by flash chromatography, eluent n-hexane/ethyl acetate 8/2. The product (0.13 g) was obtained as an oil.

C) [1R-[1α(Z),2β(R*),3α,5α]]-7-[3,5-di-TBDMSi-lyl-oxy-2-(3-TBDMSilyl-oxy-5-phenyl-pentyl)cyclopentyl]-5-heptenoic acid 3-(nitrooxy)propylamide A solution of compound B (0.1 g, 0.11 mmol) and silver nitrate (0.03 g, 0.17 mmol) in acetonitrile (50 ml) was stirred at 40° C., in the dark, for 4 hours. The precipitated (silver salts) was filtered off and the solvent was evaporated under vacuum. The residue was purified by flash chromatography, eluent n-hexane/ethyl acetate 8/2. The product (0.07 g) was obtained as oil.

D) [1R-[1α(Z),2β(R*),3α,5α]]-7-[3,5-dihydroxy-2-(3-hydroxy-5-phenylpentyl)cyclopentyl]-5-heptenoic acid 3-(nitrooxy)propylamide To a solution of compound C (0.05 g, 0.06 mmol) in THF dry under inert atmosphere a solution of n-$Bu_4$-NF in THF (1M) (0.27 ml, 0.27 mmol) was added. The mixture was stirred at room temperature 3 days and washed with water. AcOEt was added and the organic layers were washed with brine, dried with sodium sulfate and concentrated under reduced pressure. The residue was purified by flash chromatography, eluent ethyl acetate/n-hexane 7/3. The product was obtained as an oil.

$^1$H-NMR ($CDCl_3$): 7.35-7.10 (5H, m); 5.46 (2H, m); 4.54 (2H, t); 4.10 (1H, m); 3.76 (1H, m); 3.67 (1H, m); 3.35 (2H, m); 2.75 (2H, m); 2.40-2.0 (8H, m); 1.90-1.45 (10H, m); 1.45-1.25 (2H, m).

What we claim is:

1. A compound of general formula (I) or a pharmaceutically acceptable salt or stereoisomer thereof $$R—X—(B)_m—Y—ONO_2 \quad (I)$$

wherein R is the prostaglandin residue of formula (II):

(II)

wherein
the symbol ═══ represents a single bond or a double bond;

L is selected from the following groups:

—$CH_2$—phenyl,

—O—(3-$CF_3$-phenyl),

—($CH_2$)$_5$—$CH_3$,

—O—(3-Cl-phenyl);

X is —$NR^1$—, wherein $R^1$=H or $C_1$-$C_6$ alkyl;

m is an integer equal to 0 or 1;

B is a radical of the formula —CH($R^1$)COO—, wherein $R^1$ is as above defined;

Y is a bivalent radical having the following meaning:

a)
  straight or branched $C_1$-$C_{20}$ alkylene, being optionally substituted with one or more of the substituents selected from the group consisting of: halogen atoms, hydroxy, —$ONO_2$ or T, wherein T is
  —OC(O)($C_1$-$C_{10}$ alkyl)-$ONO_2$ or —O($C_1$-$C_{10}$ alkyl)-$ONO_2$;
  cycloalkylene with 5 to 7 carbon atoms into cycloalkylene ring, the ring being optionally substituted with side chains $T_1$, wherein $T_1$ is straight or branched $C_1$-$C_{10}$ alkyl;

b)
  —($CH_2$)$_n$-phenyl-($CH_2$)$_{n^1}$— c)
  —($CH_2$)$_n$-phenyl(COOH)-($CH_2$)$_{n^1}$— wherein n is an integer from 0 to 20, and $n^1$ is an integer from 1 to 20;

d)
  —phenyl($OR^2$)$_{n^2}$—$X_1$—Z— wherein
$X_1$=—OCO— or —COO— and $R^2$ is H or $CH_3$;

Z is —($CH_2$)$_{n^1}$— or the bivalent radical defined above under b);

$n^1$ is as defined above and $n^2$ is an integer from 0 to 2;

e)

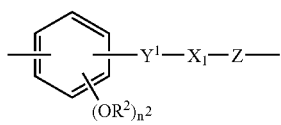

wherein:
$Y^1$ is $-CH_2-CH_2-(CH_2)_{n^2}-$ or $-CH=CH-(CH_2)_{n^2}-$;
Z, $n^1$, $n^2$, $R^2$ and $X_1$ are as defined above;
with the proviso that:
  i) when Y is selected from the bivalent radicals mentioned under b)-e), then the terminal $-ONO_2$ group is bound to $-(CH_2)_{n^1}$;
  ii) when y is selected from the bivalent radicals mentioned under b) or c) and n=0, then m=1;
  iii) when y is selected from the bivalent radicals mentioned under d) or e), then m=1;

g)

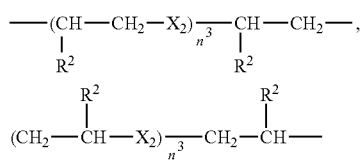

wherein $X_2$ is $-O-$ or $-S-$, $n^3$ is an integer from 1 to 6, $R^2$ is as defined above;

h)

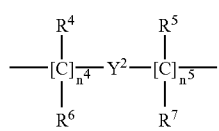

wherein:
$n^4$ is an integer from 0 to 10;
$n^5$ is an integer from 1 to 10;
$R^4, R^5, R^6, R^7$ are the same or different, and are H or straight or branched $C_1$-$C_4$ alkyl;
wherein the $-ONO_2$ group is linked to

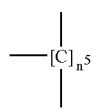

wherein $n^5$ is as defined above;
$Y^2$ is an heterocyclic saturated, unsaturated or aromatic 5 or 6 members ring, containing one or more heteroatoms selected from nitrogen, oxygen, sulfur, and is selected from

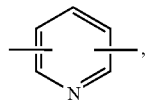 (Y1)

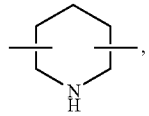 (Y2)

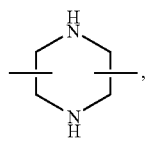 (Y3)

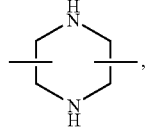 (Y4)

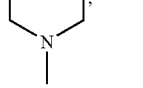 (Y5)

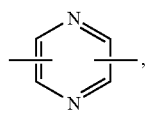 (Y6)

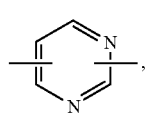 (Y7)

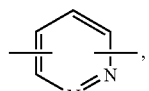 (Y8)

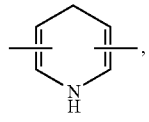 (Y9)

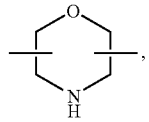 (Y10)

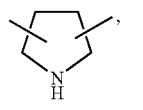 (Y11)

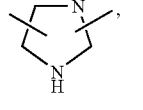 (Y12)

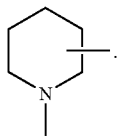
(Y13)

2. The compound of claim 1, wherein R is the prostaglandin residue of formula (II) having formula:

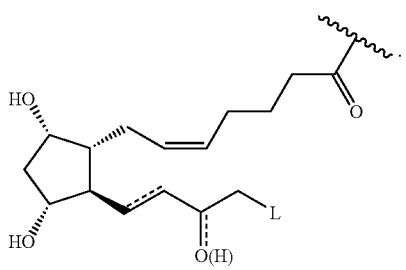
(II)

3. A compound of general formula (I) according to claim 1 or a pharmaceutically acceptable salt or stereoisomer thereof, wherein R, L, X, and B are as defined in claim 1 and Y is a bivalent radical having a meaning selected from the following group:

a)
straight or branched $C_1$-$C_{10}$ alkylene, being optionally substituted with one or more of the substituents selected from the group consisting of: halogen atoms, hydroxy, —$ONO_2$ or T, wherein T is
OC(O)($C_1$-$C_{10}$ alkyl)-$ONO_2$ or —O($C_1$-$C_{10}$ alkyl)-$ONO_2$;
cycloalkylene with 5 to 7 carbon atoms into cycloalkylene ring, the ring being optionally substituted with side chains Ti, wherein Ti is $CH_3$;

b)
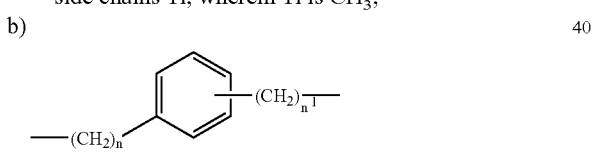

c)
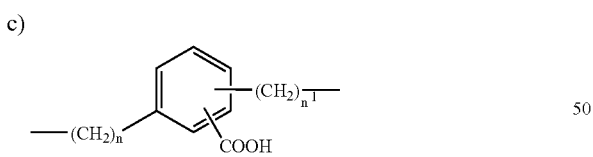

wherein n is an integer from 0 to 5, and $n^1$ is an integer from 1 to 5;

d)

wherein:
$X_1$=—OCO— or —COO— and $R^2$ is H or $CH_3$;
Z is $(CH_2)_n^1$— or the bivalent radical defined above under b);

$n^1$ is an integer from 1 to 10 and $n^2$ is an integer from 0 to 2;

e)
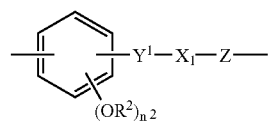

wherein:
$Y^1$ is $CH_2$—$CH_2$— or CH=CH—$(CH_2)_n^2$—;
Z, $n^1$, $n^2$, $R^2$ and $X_1$ are as above defined;
with the proviso that:
i) when Y is selected from the bivalent radicals mentioned under b)-e), then the terminal —$ONO_2$ group is bound to —$(CH_2)_n^1$;
ii) when Y is selected from the bivalent radicals mentioned under b) or c) and n=0, then m=1;
iii) when Y is selected from the bivalent radicals mentioned under d) or e), then m=1;

f)

$$—(CH—CH_2—X_2)_{\overline{n^3}}CH—CH_2—,$$
$$\quad\;\;|\qquad\qquad\qquad\;\;|$$
$$\quad R^2\qquad\qquad\qquad R^2$$

$$\qquad\qquad R^2\qquad\qquad\;\; R^2$$
$$\qquad\qquad\;|\qquad\qquad\;\;\;|$$
$$—(CH_2—CH—X_2)_{\overline{n^3}}CH_2—CH—$$

wherein $X_2$ is —O— or —S—, $n^3$ is an integer from 1 to 4 and $R^2$ is as defined above;

g)
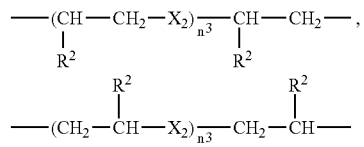

wherein:
$n^4$ is an integer from 0 to 3;
$n^5$ is an integer from 1 to 3;
$R^4$, $R^5$, $R^6$, $R^7$ are H;
wherein the —$ONO_2$ group is linked to

wherein $n^5$ is as defined above;
$Y^2$ is selected from

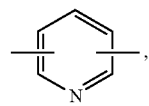
(Y1)

-continued

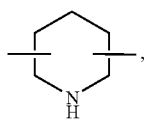 (Y2)

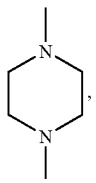 (Y4)

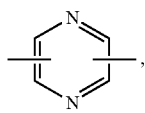 (Y5)

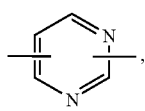 (Y6)

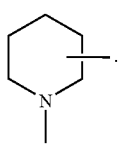 (Y13)

4. A compound of general formula (I) according to claim 1, wherein L is selected from the following groups:

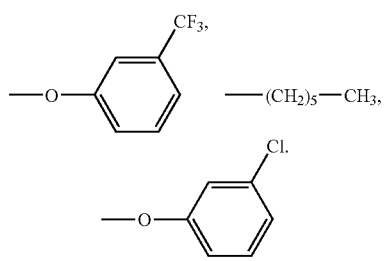

5. A compound of general formula (I) according to claim 1, wherein the residue R is selected from the group consisting of travoprost, unoprostone and cloprostenol.

6. A compound of general formula (I) according to claim 1, wherein the residue R is latanoprost.

7. A compound of general formula (I) according to claim 1, wherein Y is a bivalent radical having the following meaning:
 a) straight or branched $C_2$-$C_6$ alkylene, being optionally substituted with —$ONO_2$;
 b)

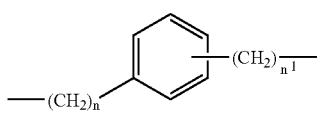

wherein n is 0 or 1, and $n^1$ is 1;

c)

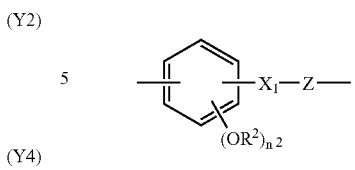

wherein
 $X_1$=—OCC— or —COO— and $R^2$ is H or $CH_3$;
 Z is $(CH_2)_n{}^1$—;
 n is an integer from 1 to 5 and n is an integer from 0 to 2;

d)

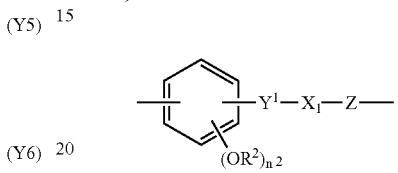

wherein:
 $Y^1$ is —$CH_2$—$CH_2$—$(CH_2)_n{}^2$— or —CH=CH—$(CH_2)_n{}^2$—;
 Z is $(CH_2)_n{}^1$— or the bivalent radical defined above under b);
 $n^1$ is an integer from 1 to 5;
 $n^2$, $R^2$ and $X_1$ are as above defined;
 with the proviso that:
  i) when Y is selected from the bivalent radicals mentioned under b), d) and e), then the terminal —$ONO_2$ group is bound to —$(CH_2)_n{}^1$;
  ii) when Y is selected from the bivalent radicals mentioned under b) and n=0, then m=1;
  iii) when Y is selected from the bivalent radicals mentioned under d) or e), then m=1;

e)

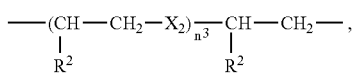

wherein $X_2$ is —O— or —S—, $n^3$ is 1, $R^2$ is hydrogen;

f)

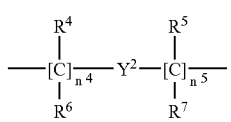

wherein:
 $n^4$ is 2 or 3;
 $n^5$ is 2 or 3;
 $R^4$, $R^5$, $R^6$, $R^7$ are H;
 wherein the —$ONO_2$ group is linked to

wherein $n^5$ is as defined above;

$Y^2$ is selected from
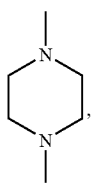
(Y4)
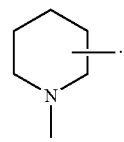
(Y13)
8. A compound according to claim 1, selected from the group consisting of:
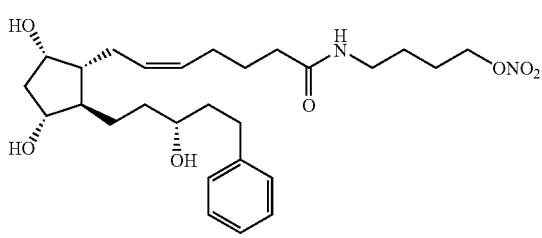
(1) (2)
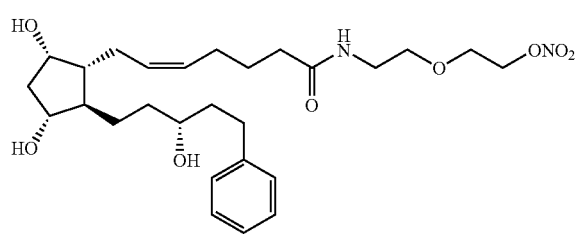
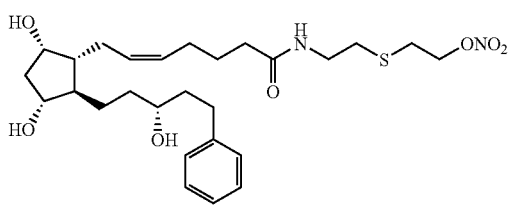
(3) (4)
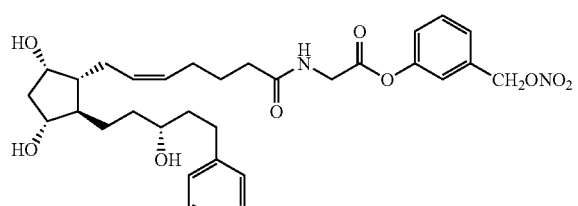
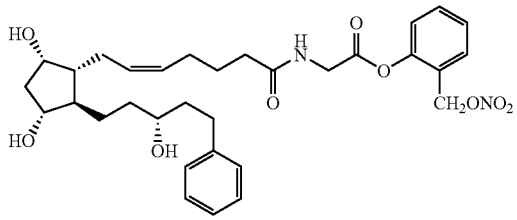
(5) (6)
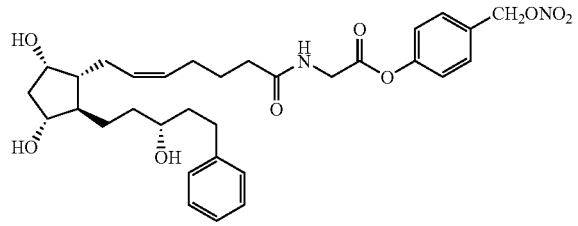
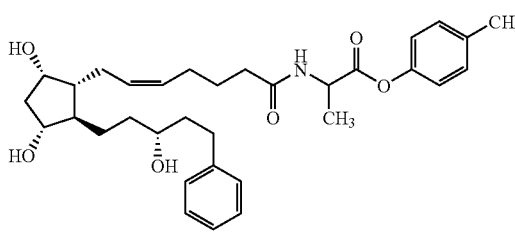
(7) (8)
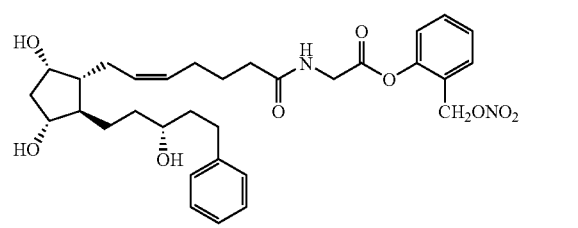
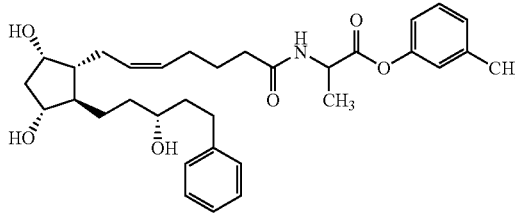
(9) (10)
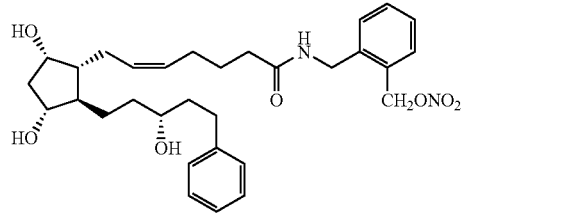

-continued
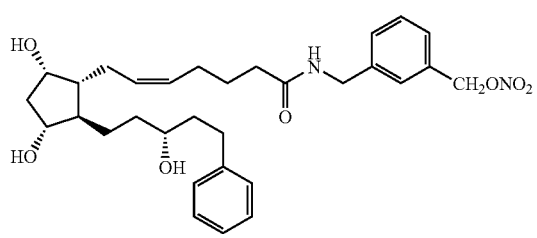
(11)
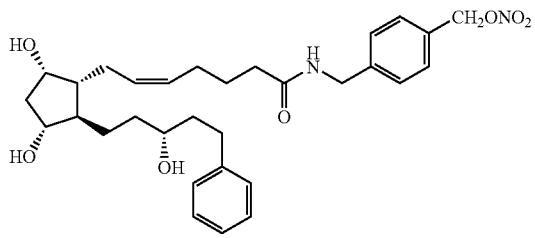
(12)
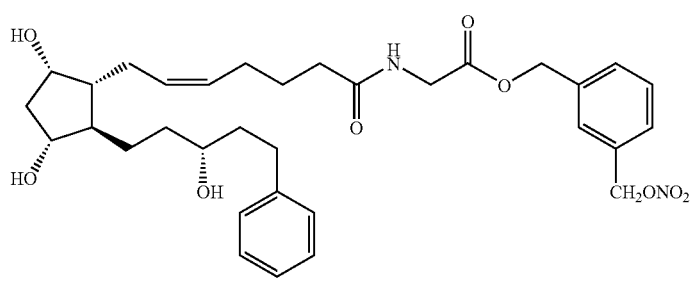
(13)
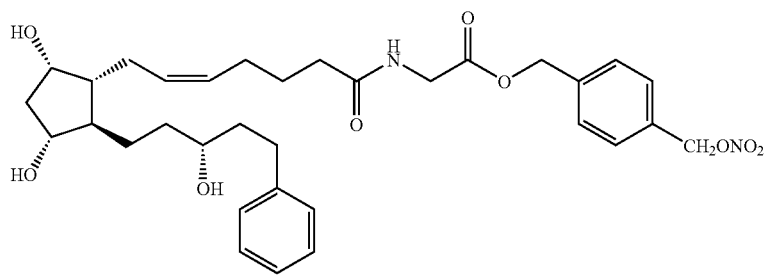
(14)
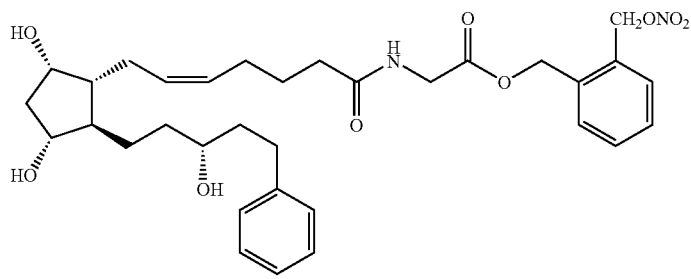
(15)
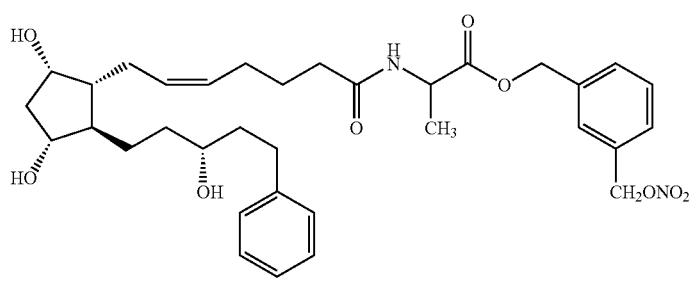
(16)

-continued
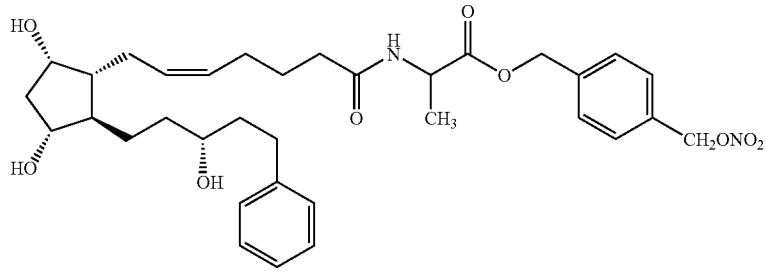
(17)
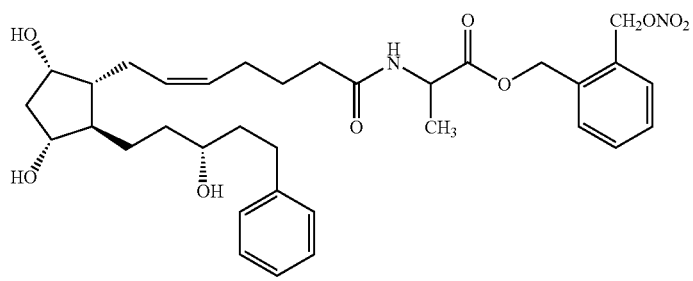
(18)
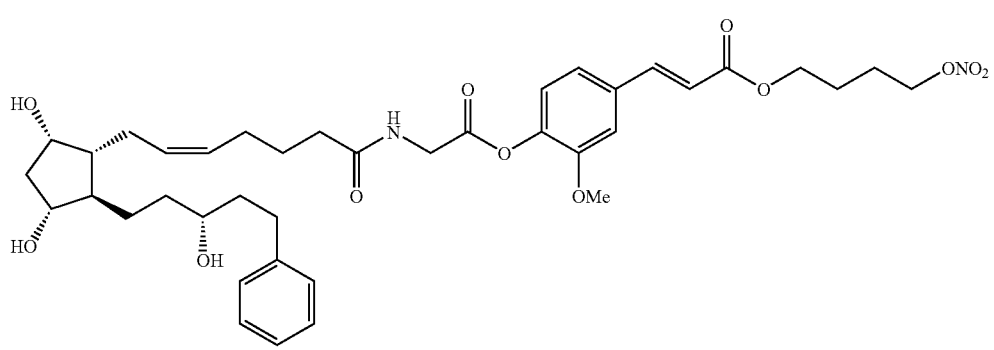
(19)
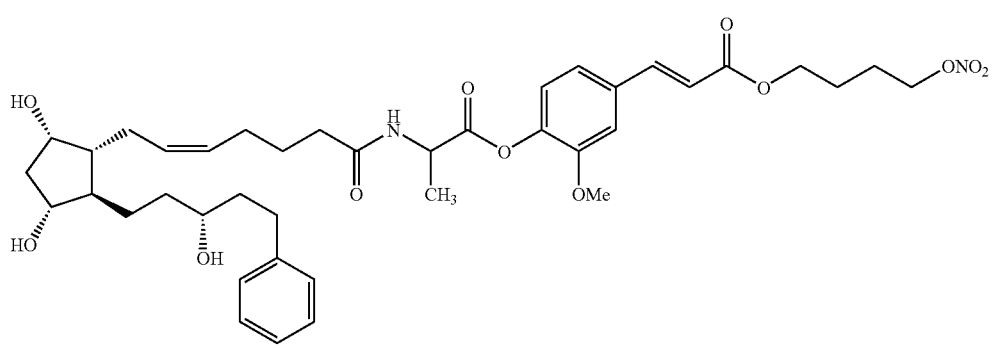
(20)
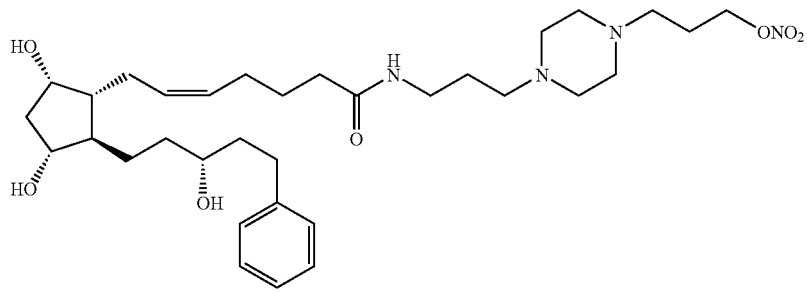
(21)

-continued
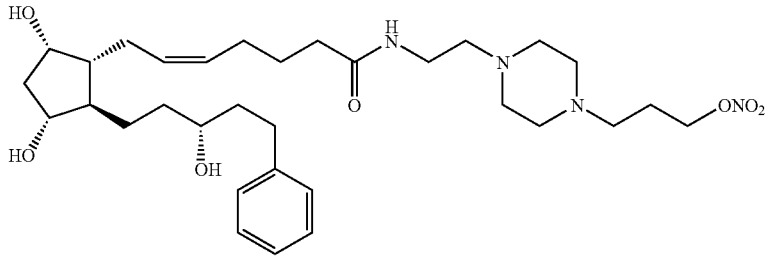
(22)
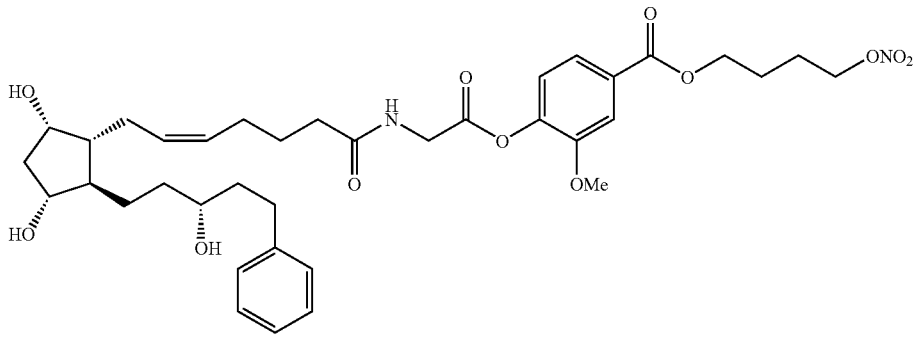
(23)
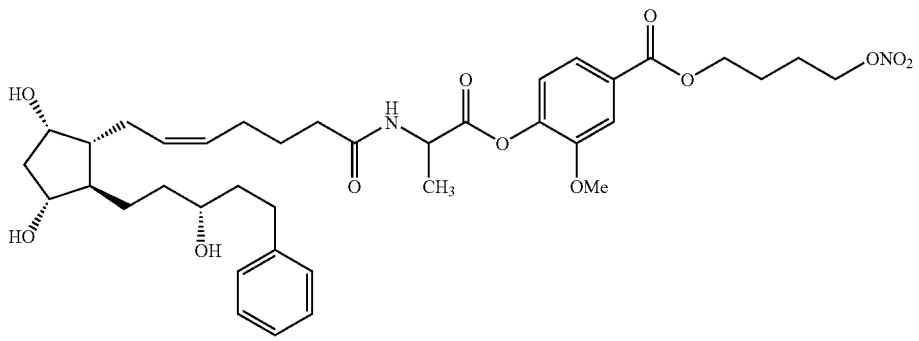
(24)
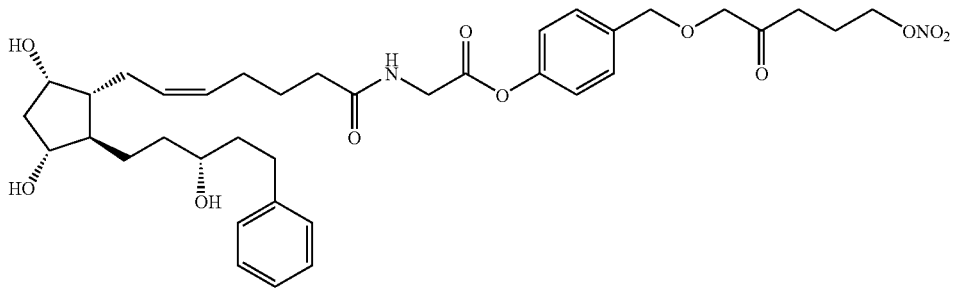
(25)
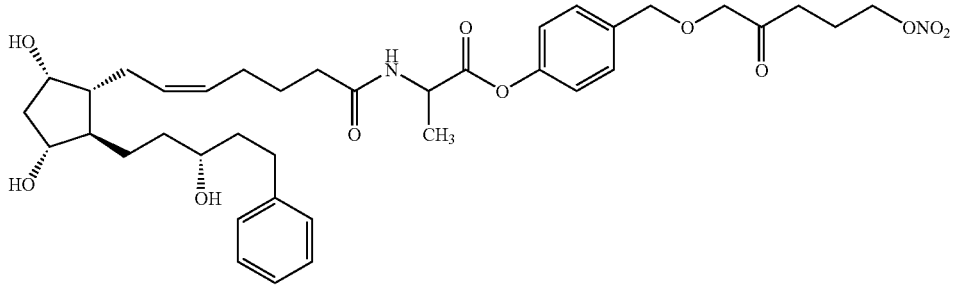
(26)

(27)
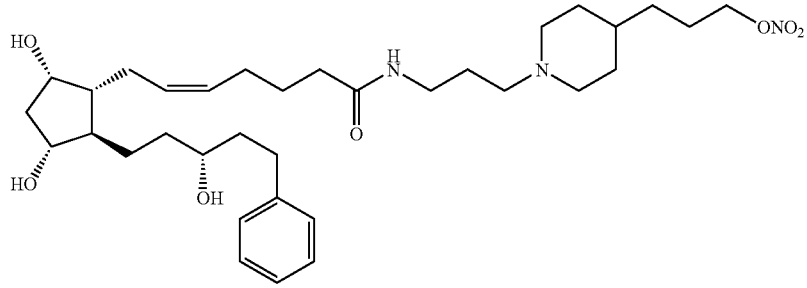
(28)
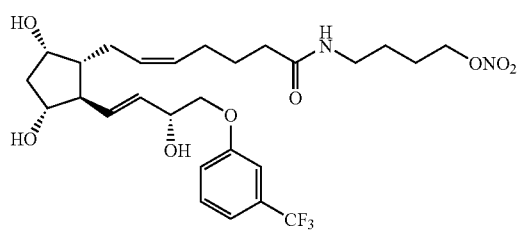
(29)
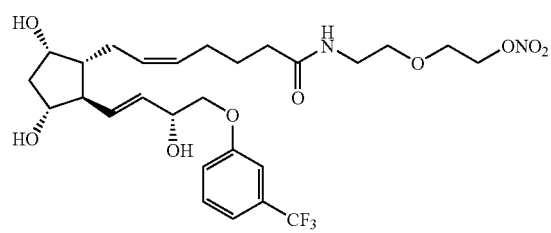
(30)
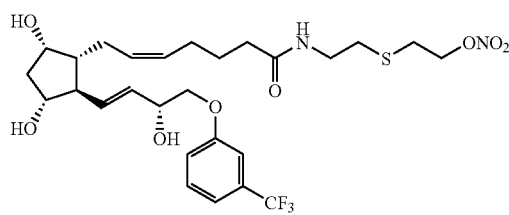
(31)
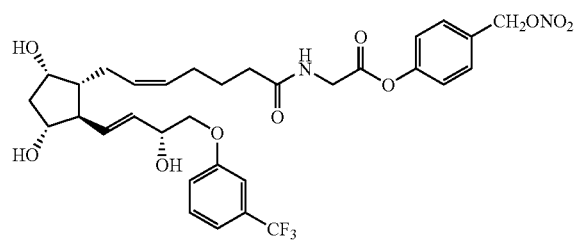
(32)
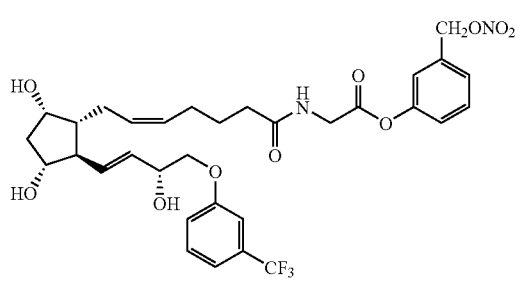
(33)
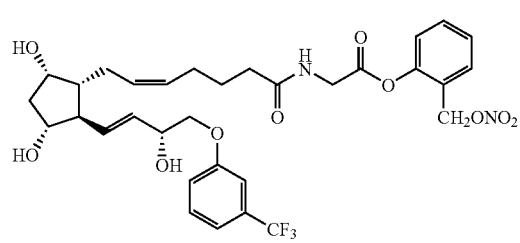
(34)
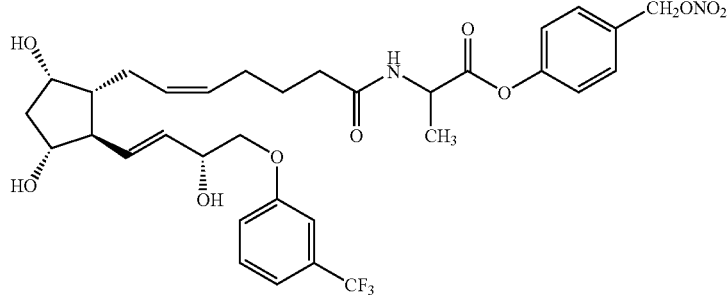

-continued
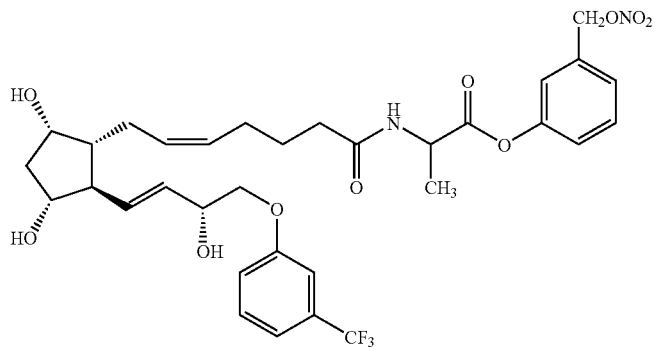
(35)
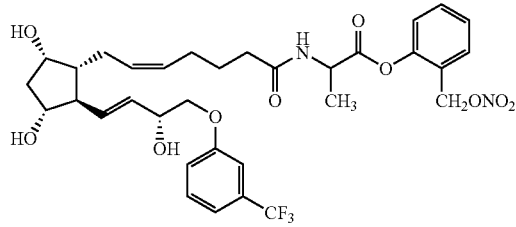
(36)
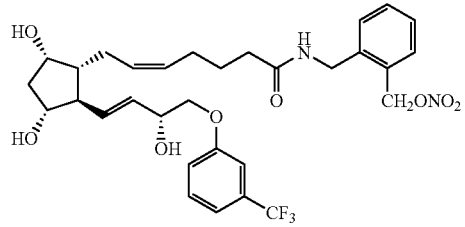
(37)
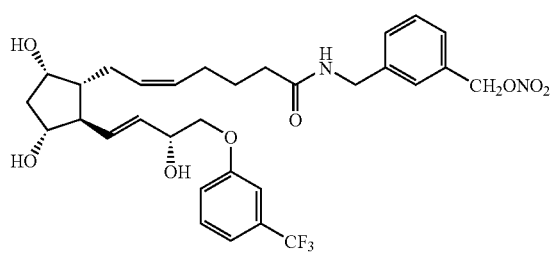
(38)
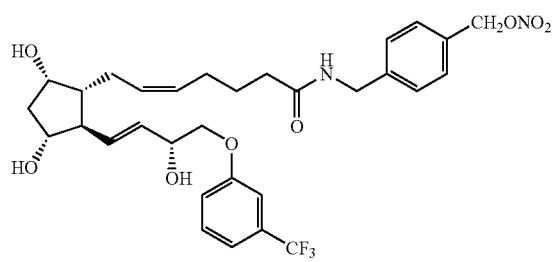
(39)
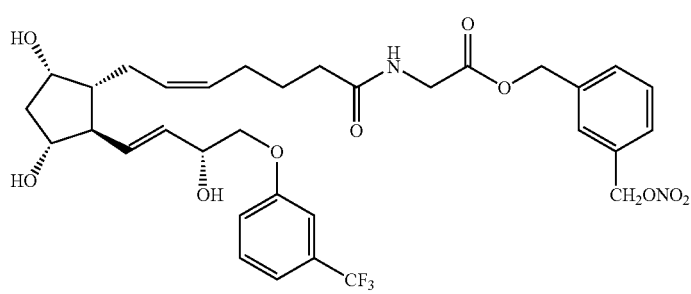
(40)
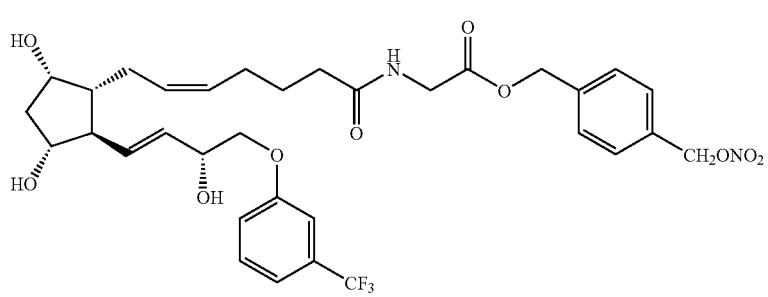
(41)

-continued
(42)
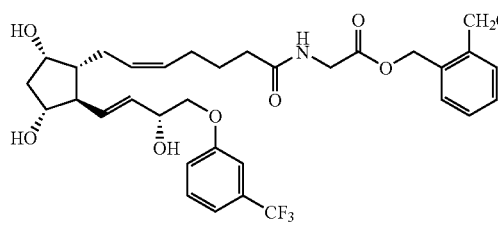
(43)
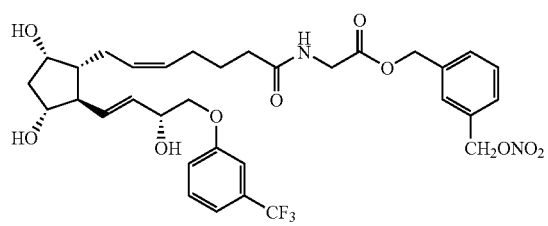
(44)
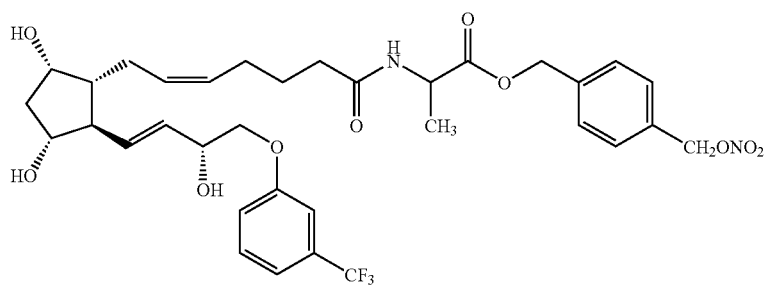
(45)
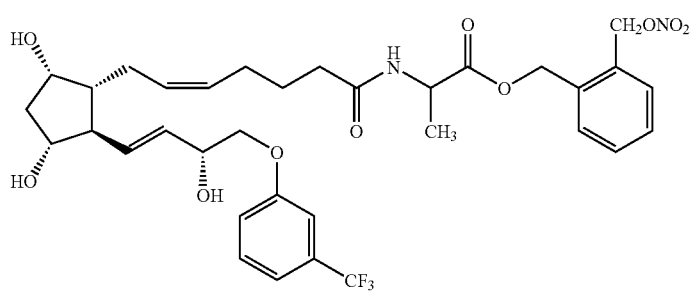
(46)
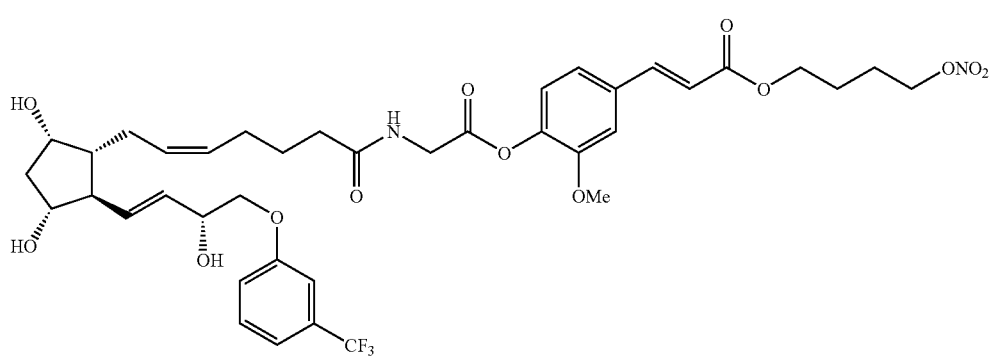
(47)
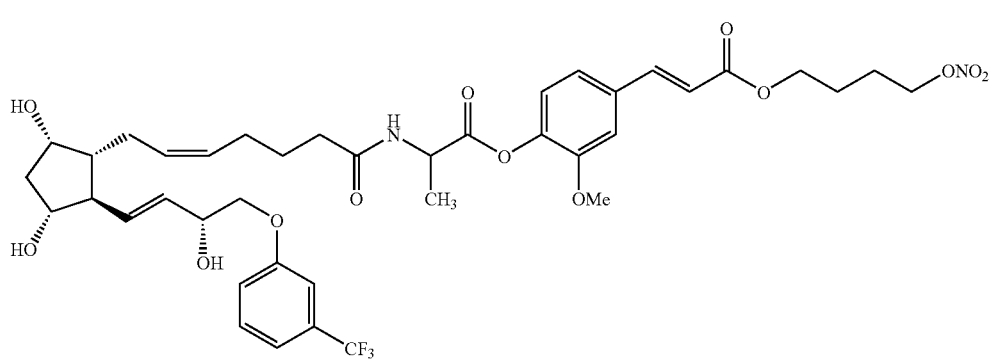

-continued
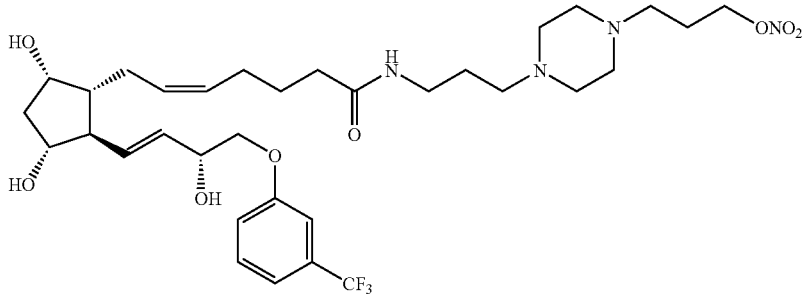
(48)
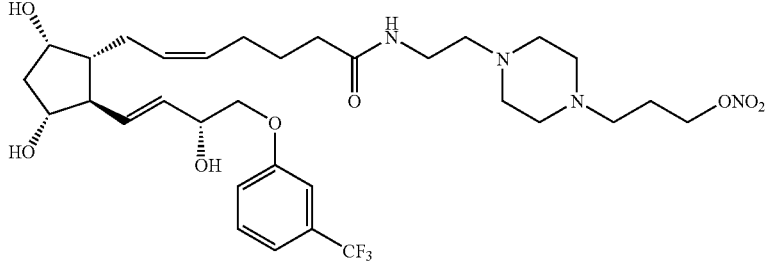
(49)
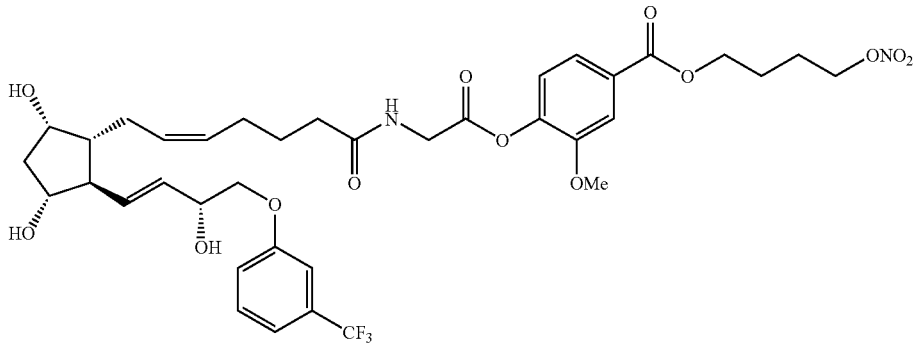
(50)
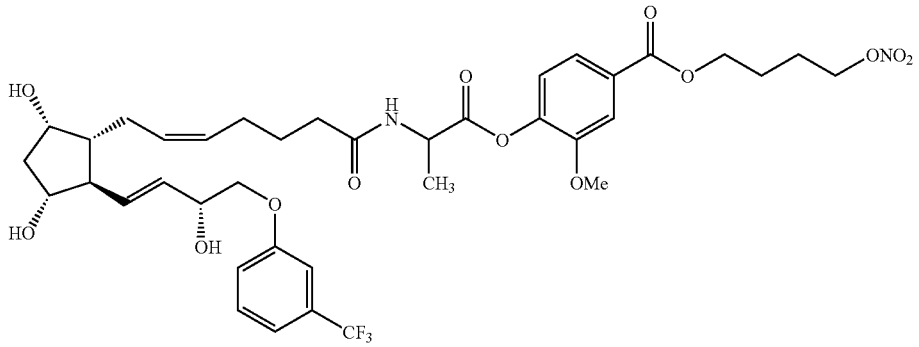
(51)
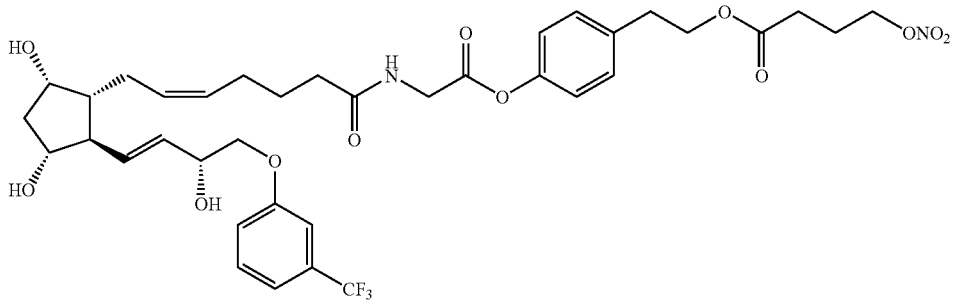
(52)

-continued
(53)
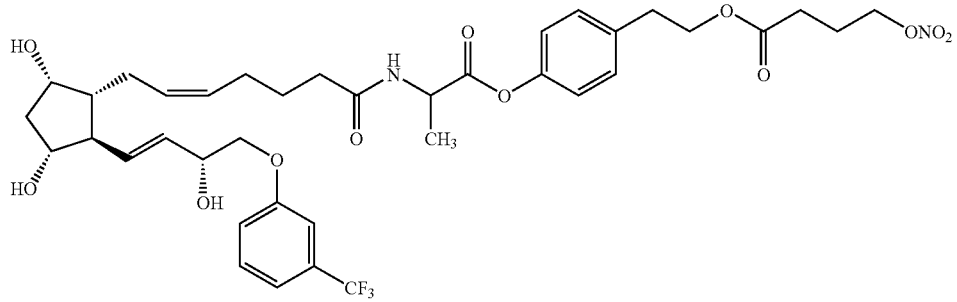
(54)
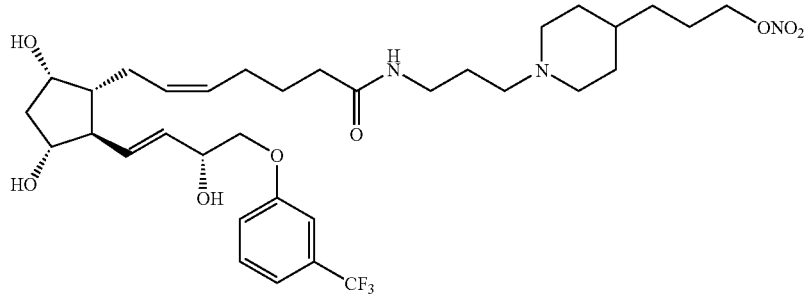
(55)
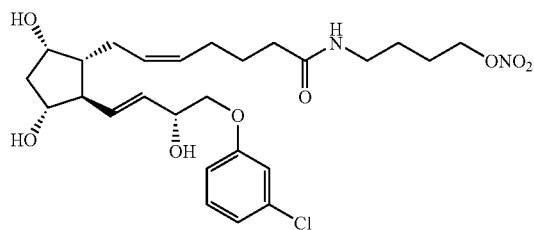
(56)
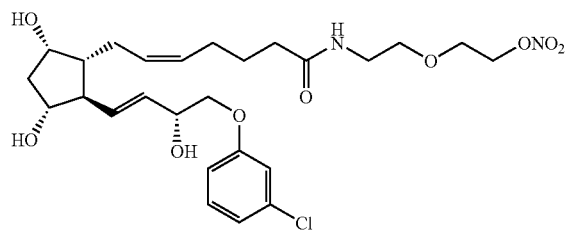
(57)
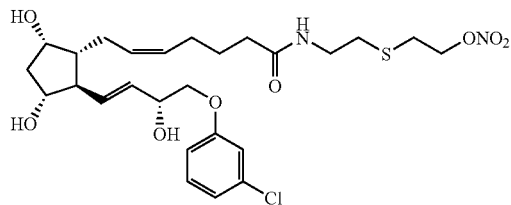
(58)
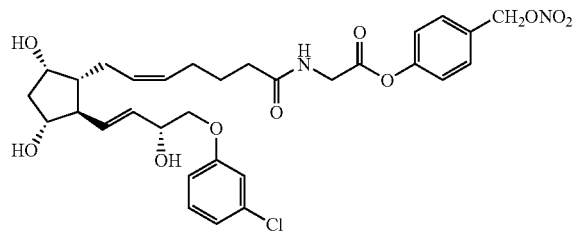
(59)
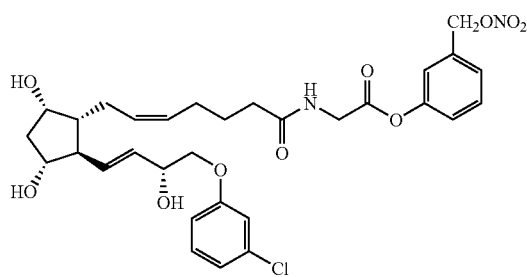
(60)
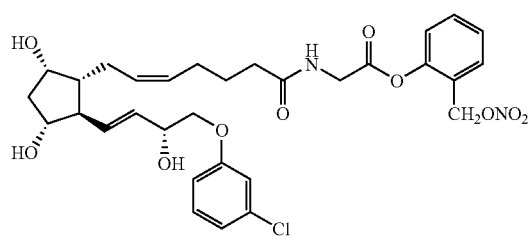

-continued
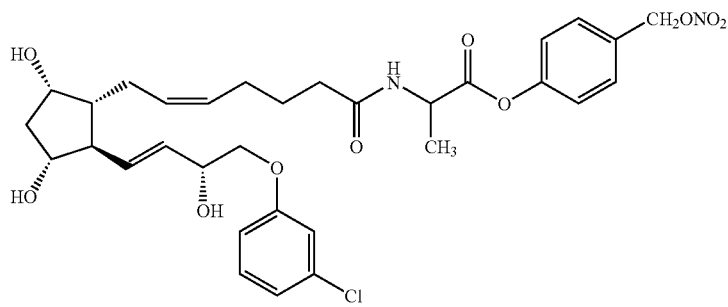
(61)
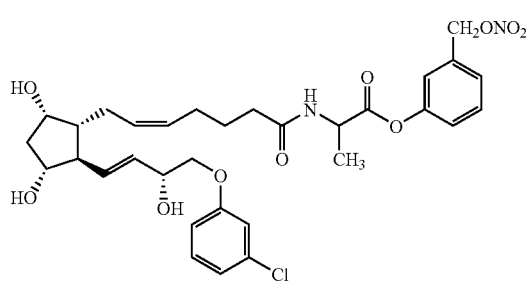
(62)
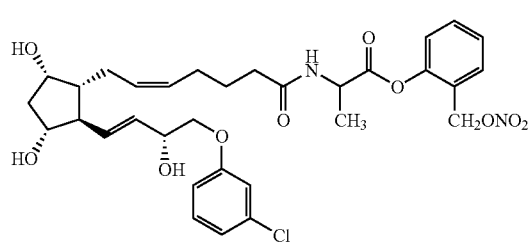
(63)
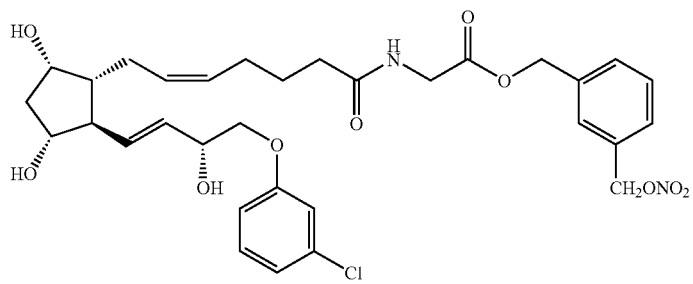
(64)
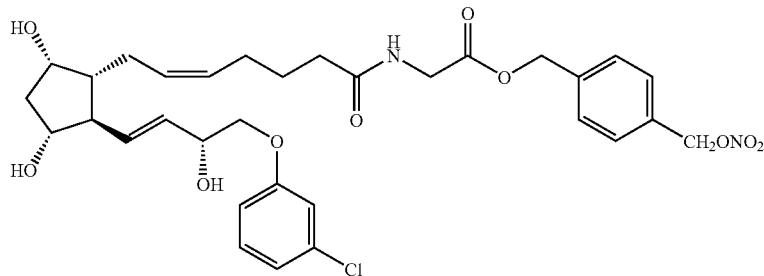
(65)
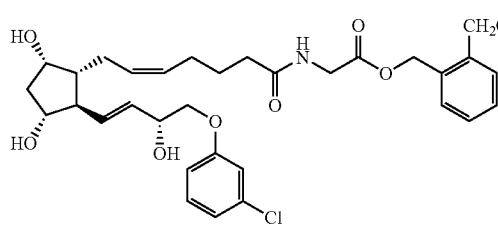
(66)
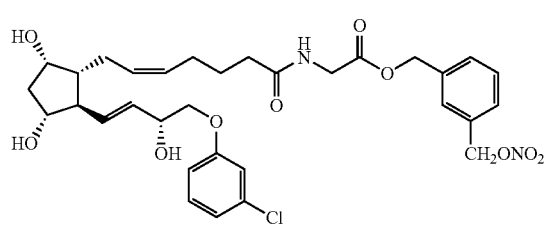
(67)

-continued
(68)
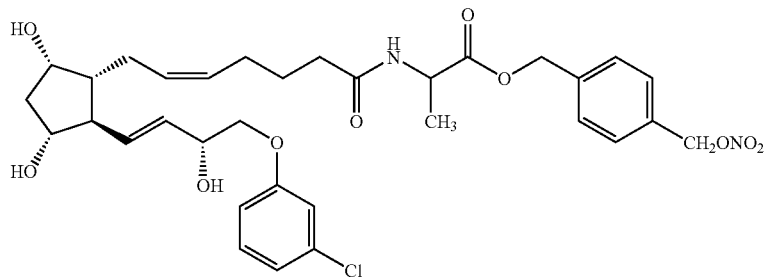
(69)
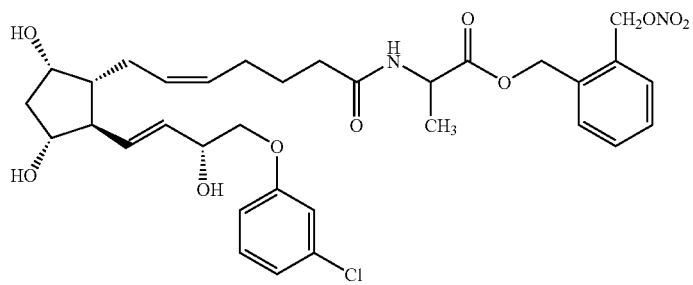
(70)
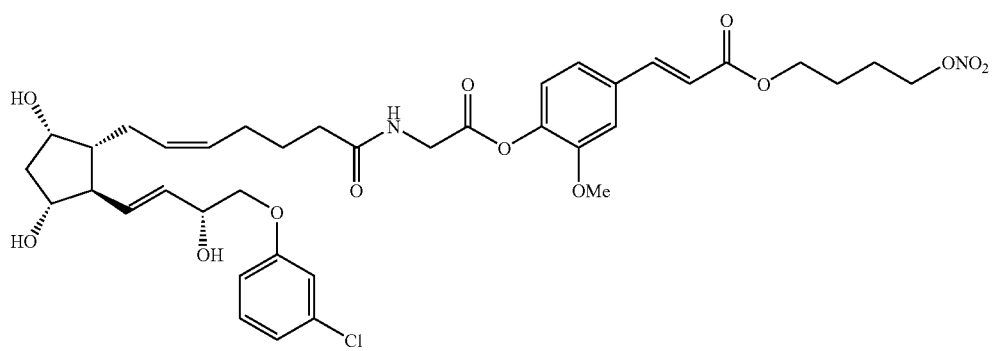
(71)
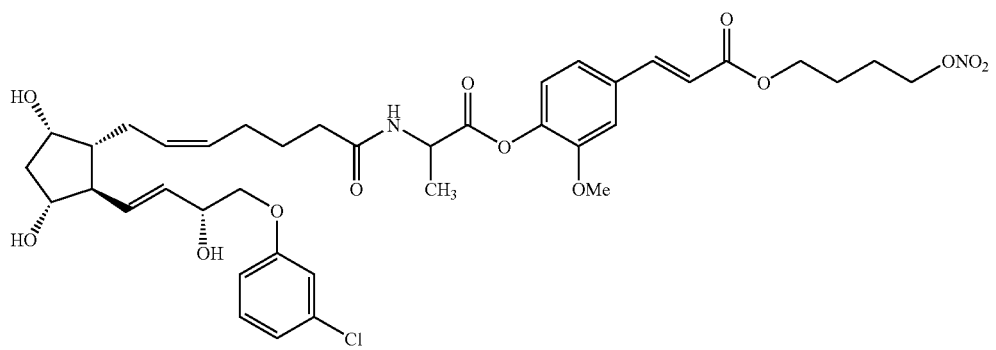
(72)
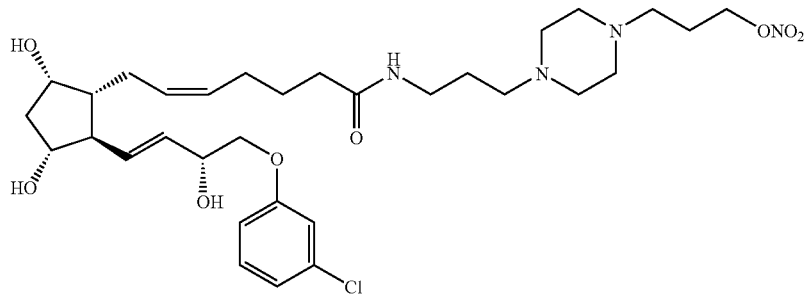

-continued
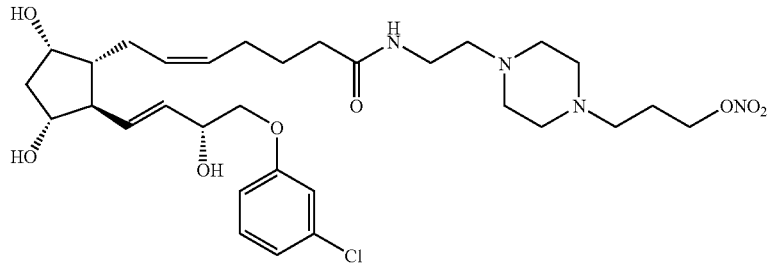
(73)
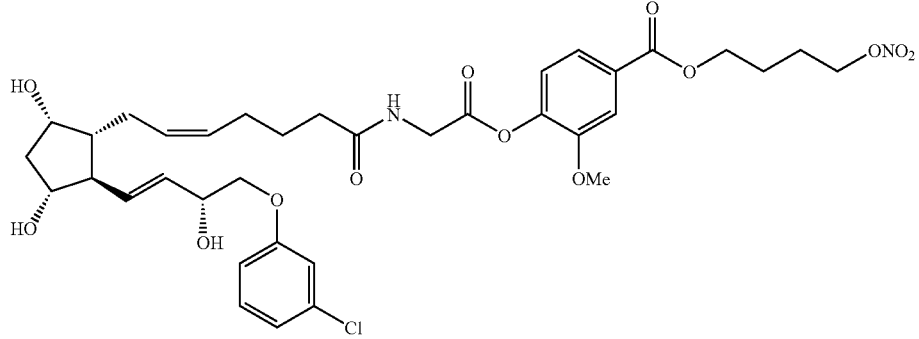
(74)
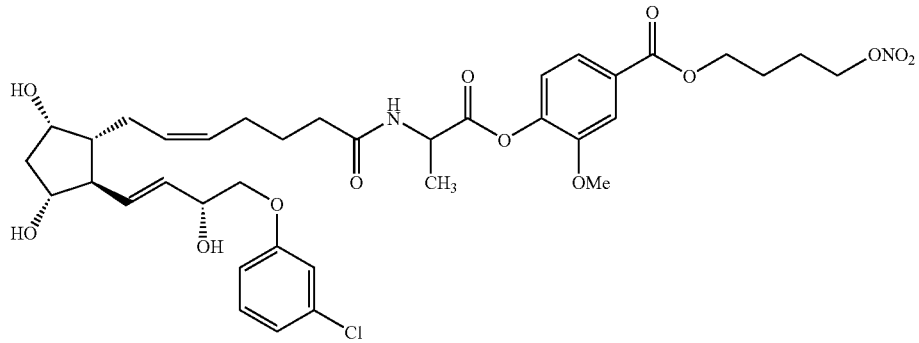
(75)
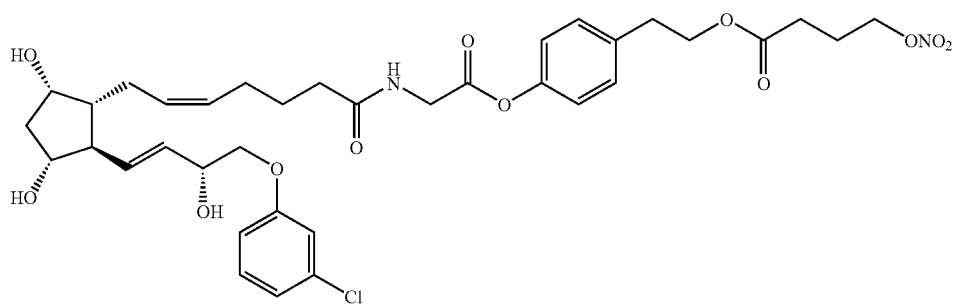
(76)
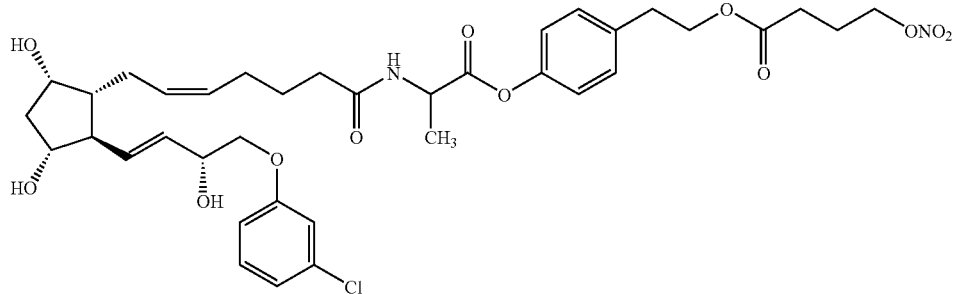
(77)

-continued
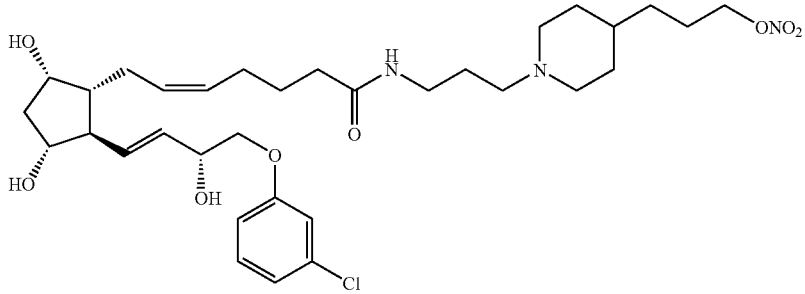
(78)
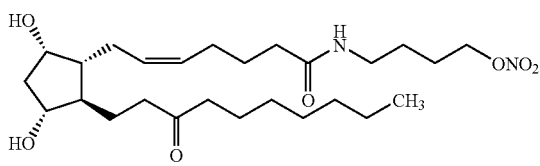
(79)
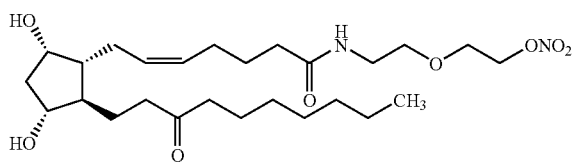
(80)
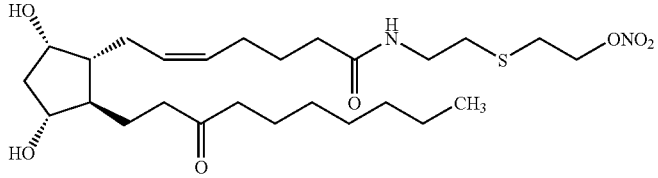
(81)
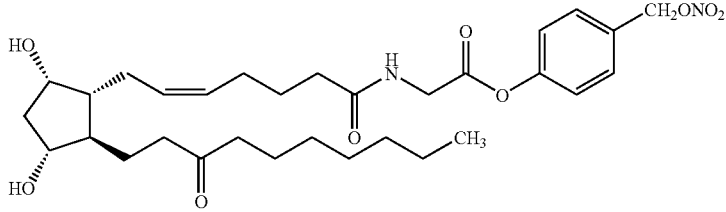
(82)
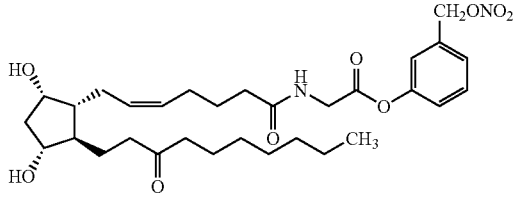
(83)
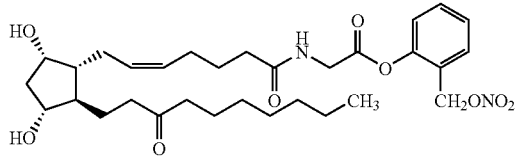
(84)
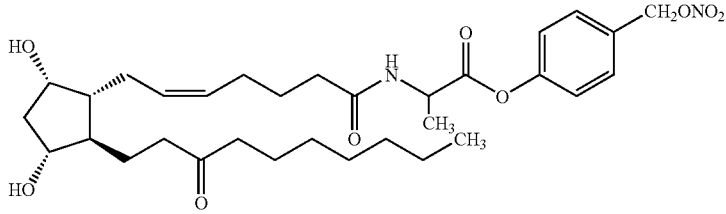
(85)
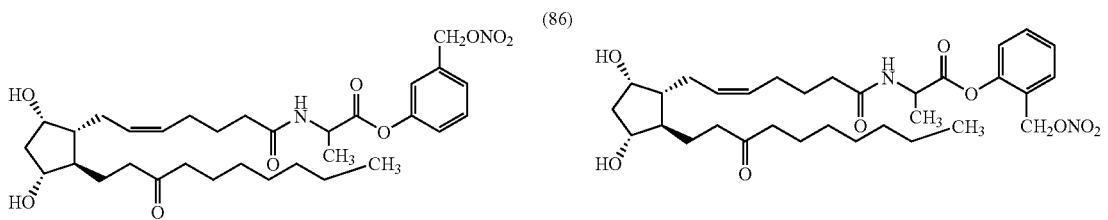
(86)                                                                 (87)

-continued
(88)
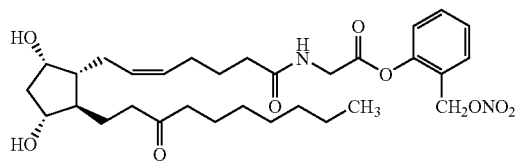
(89)
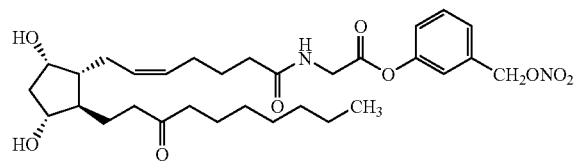
(90)
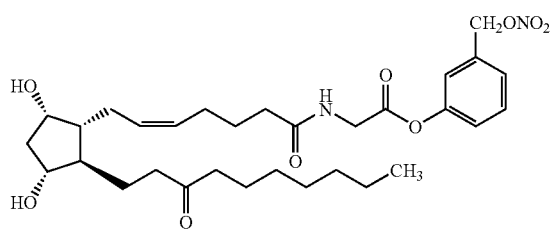
(91)
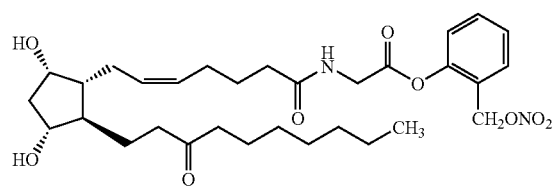
(92)
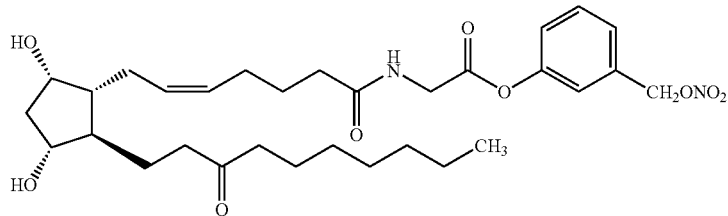
(93)
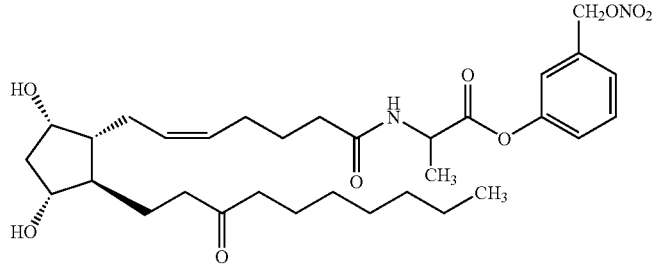
(95)
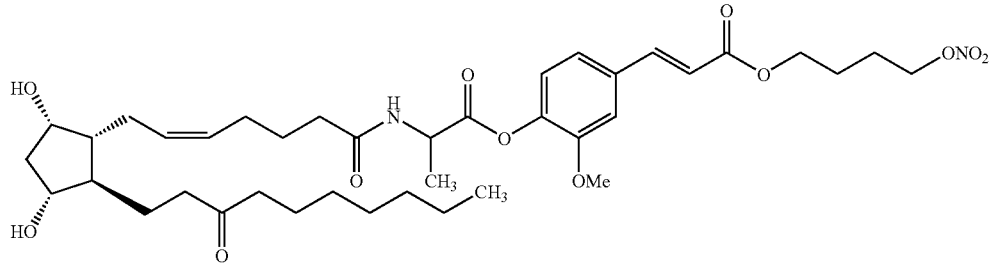
(96)
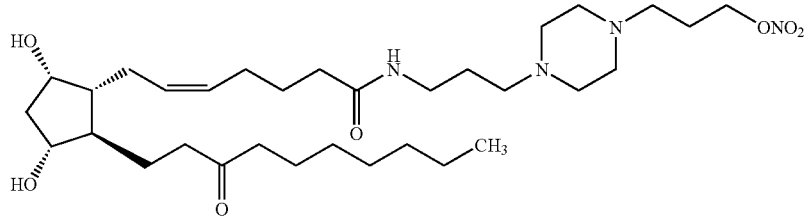

-continued
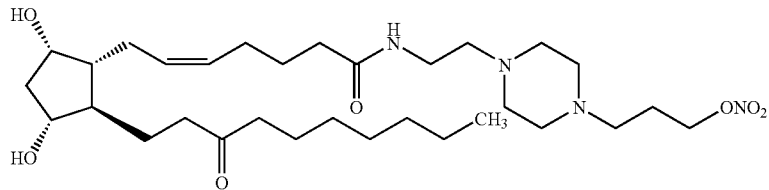
(97)
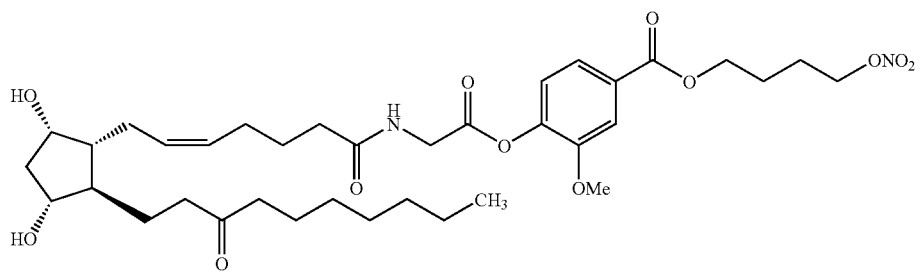
(98)
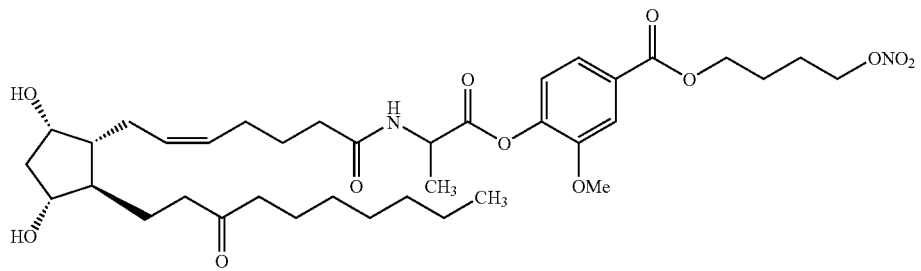
(99)
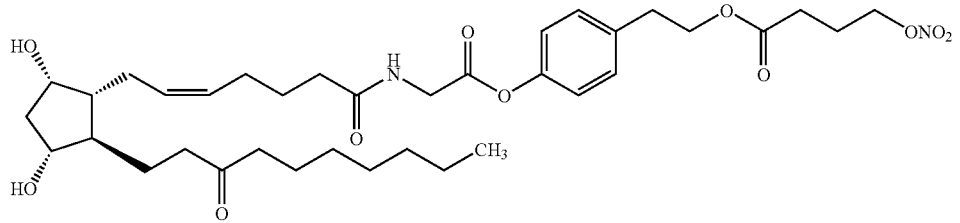
(100)
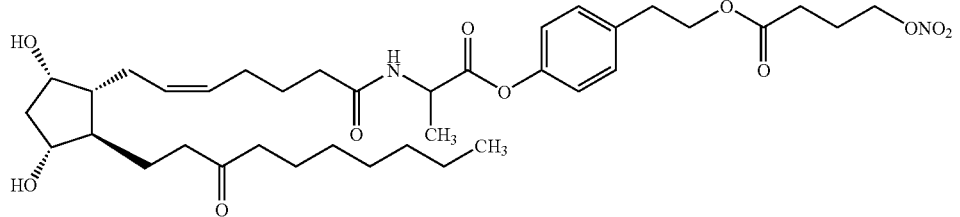
(101)
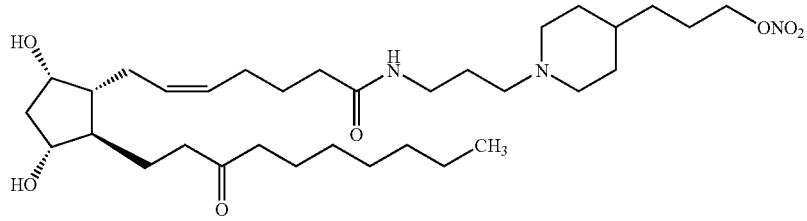
(102)

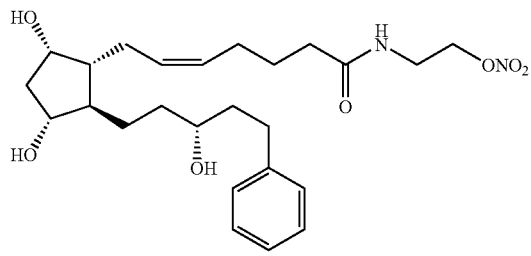
(103)
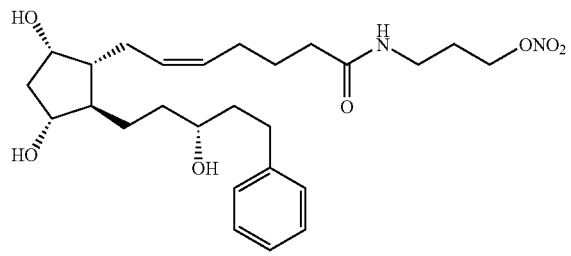
(104)
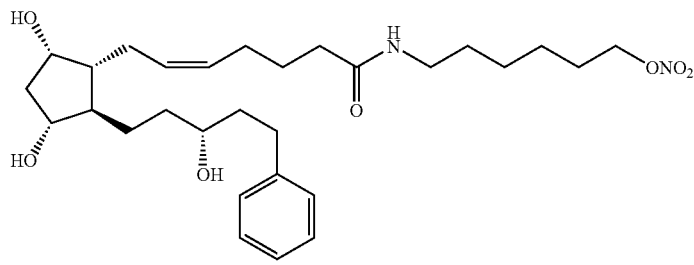
(105)
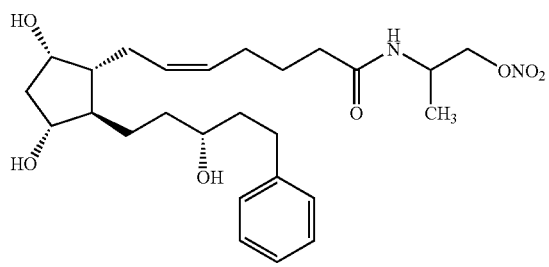
(106)
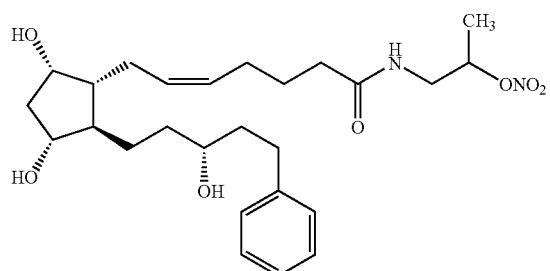
(107)
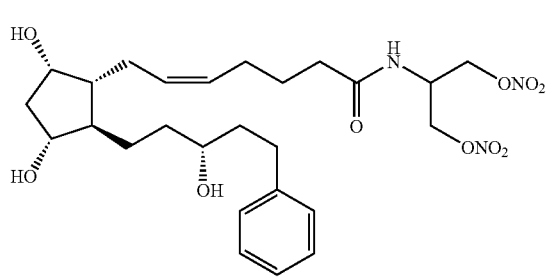
(108)
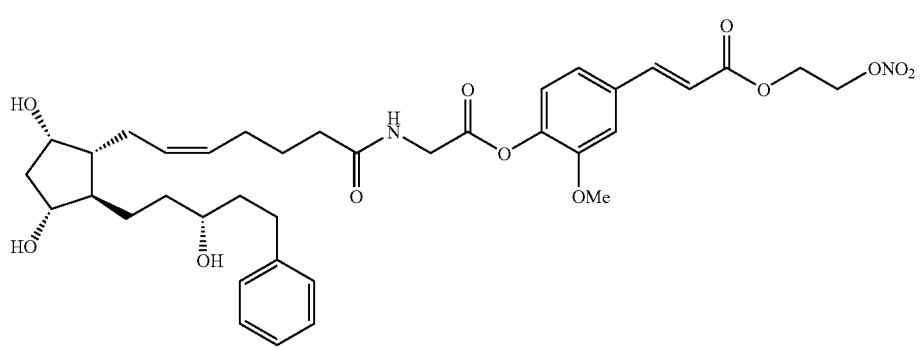
(109)

-continued
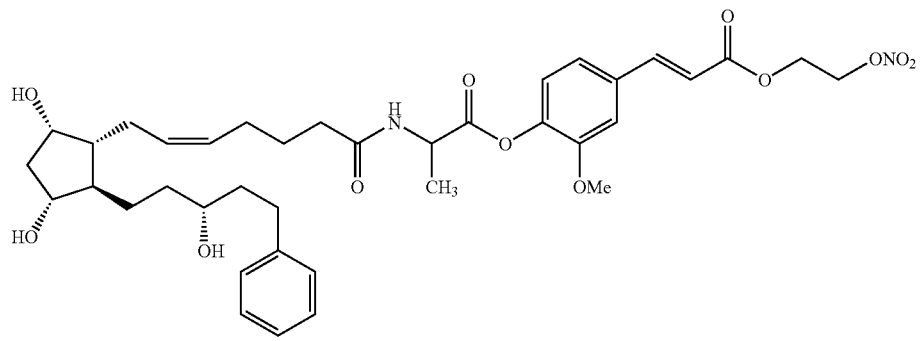
(110)
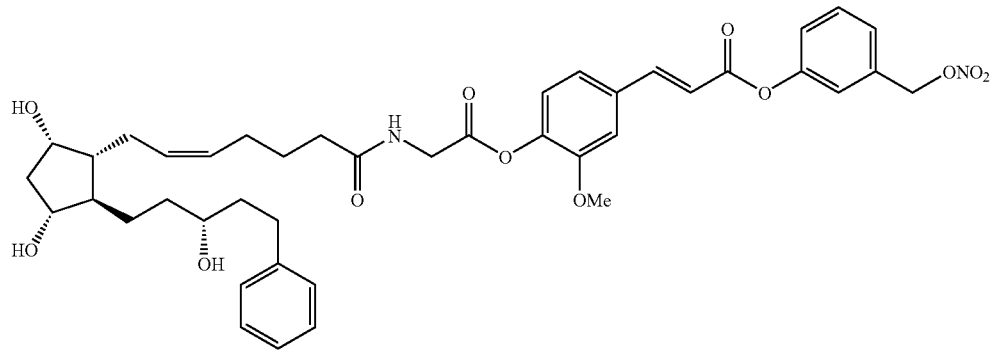
(111)
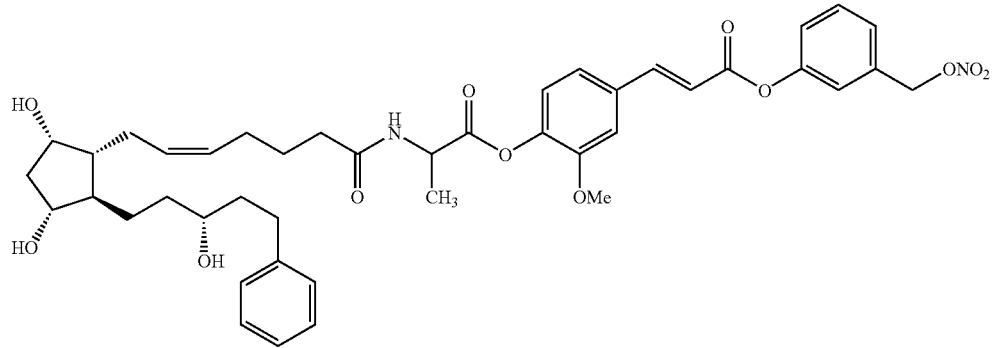
(112)
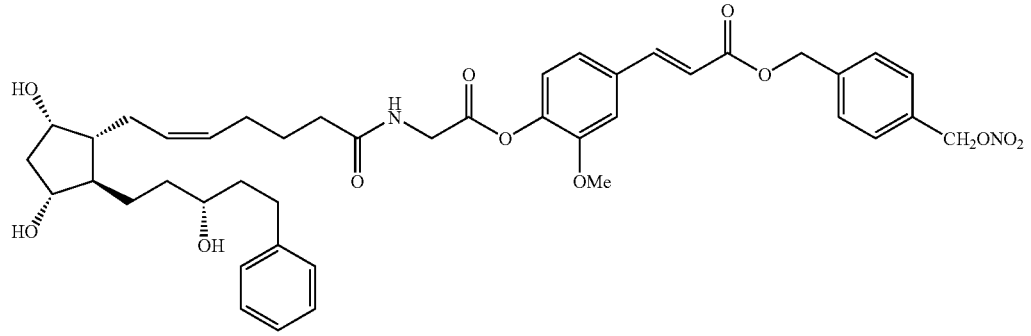
(113)

(114)
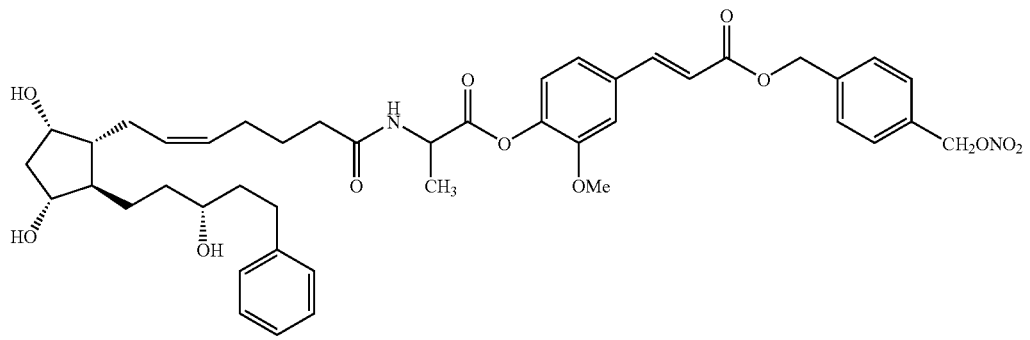
(115)
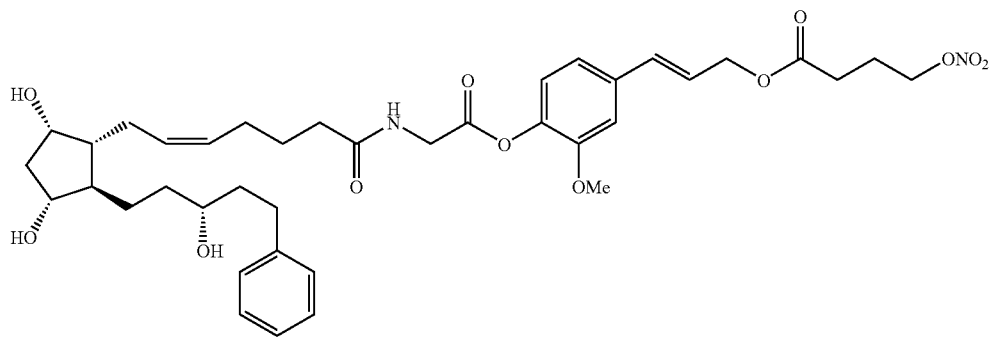
(116)
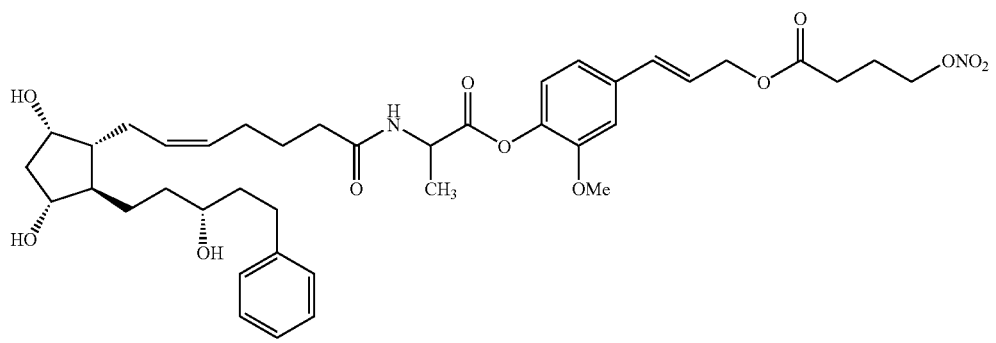
(117) (118)
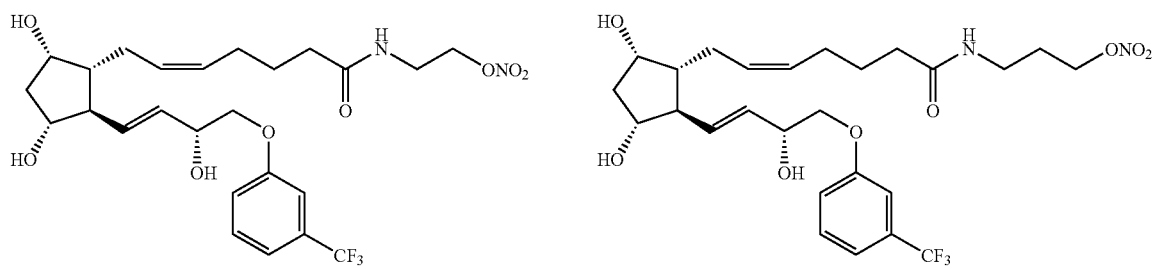
(119)
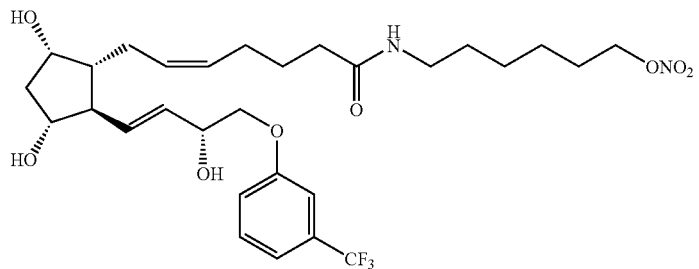

-continued
(120)
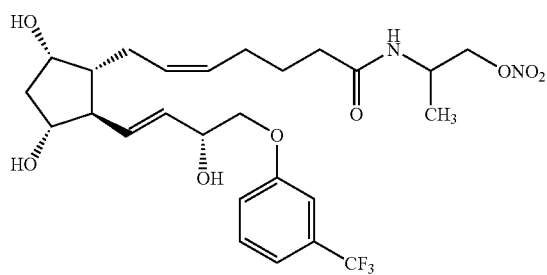
(121)
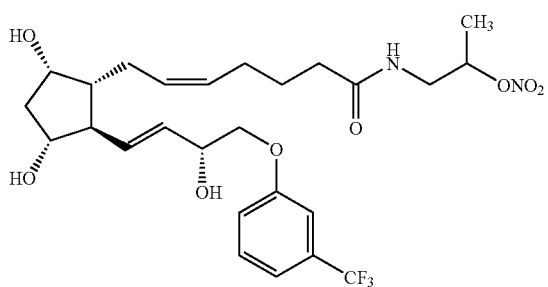
(122)
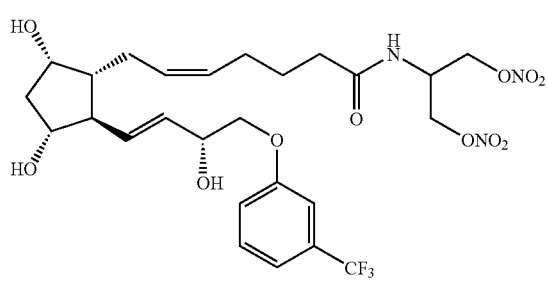
(123)
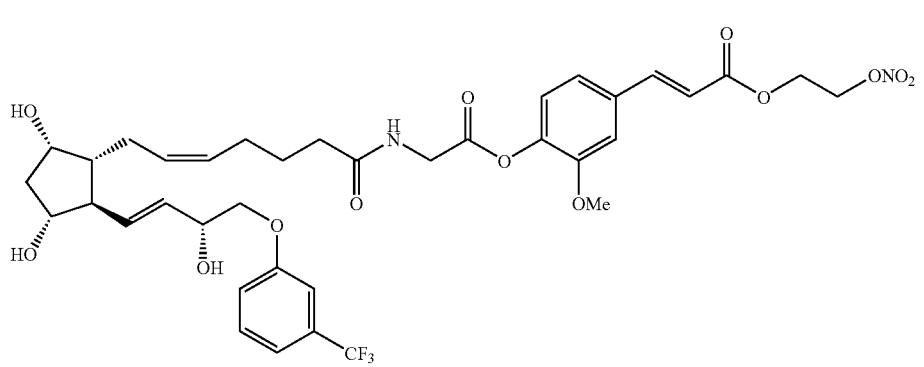
(124)
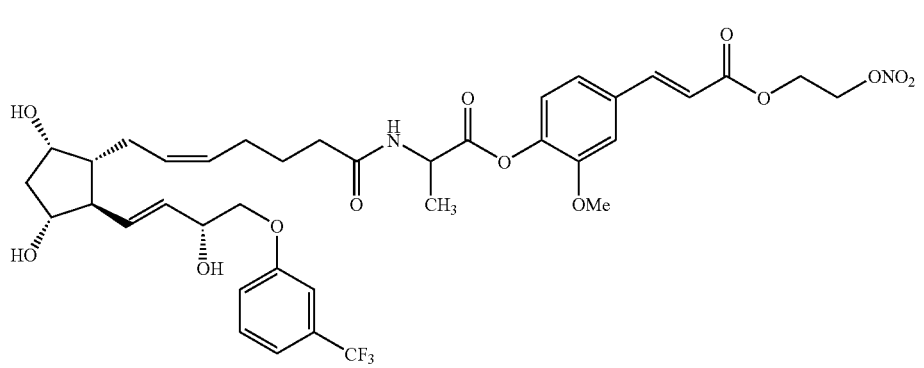

-continued
(125)
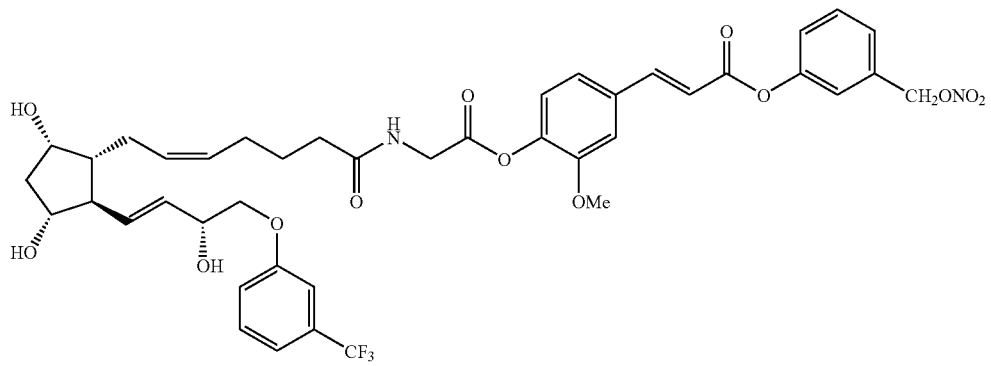
(126)
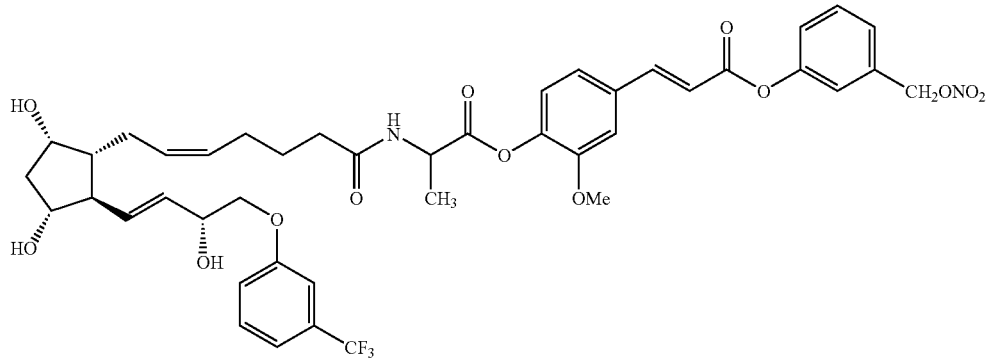
(127)
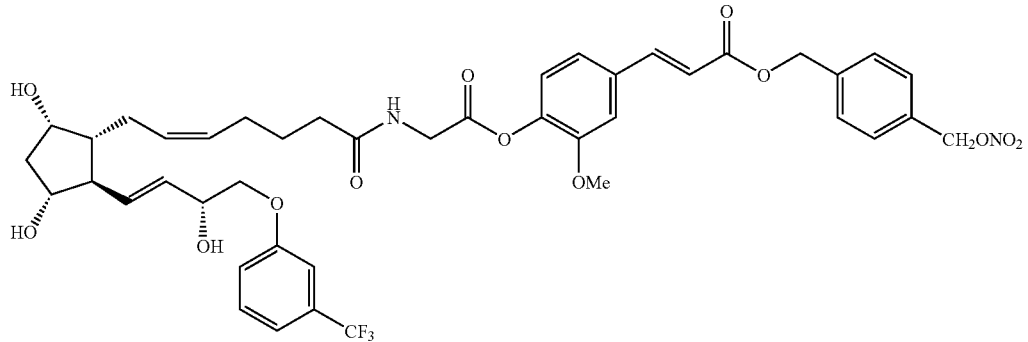
(128)
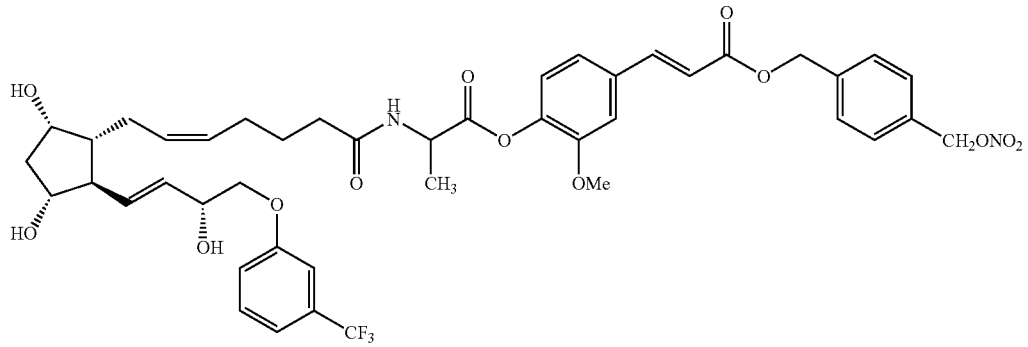

-continued
(129)
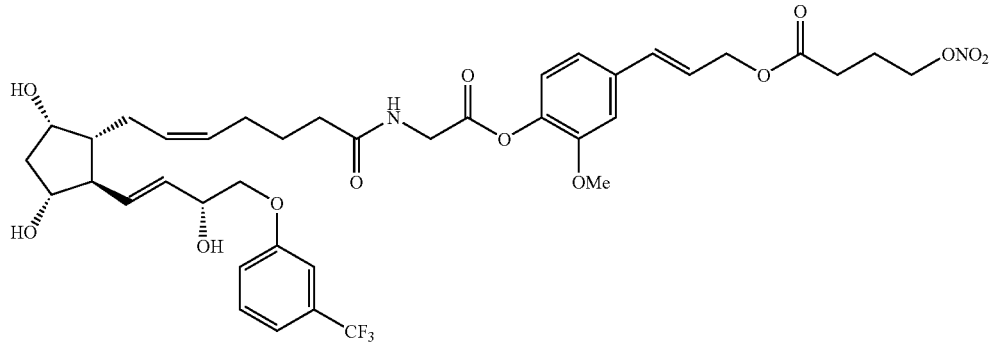
(130)
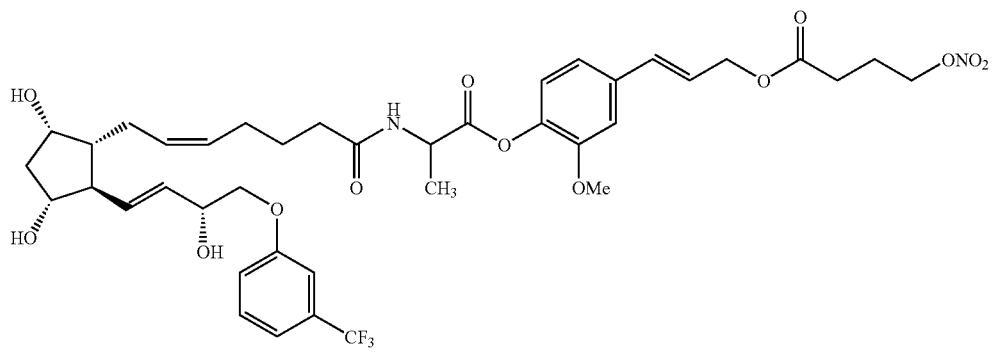
(131)
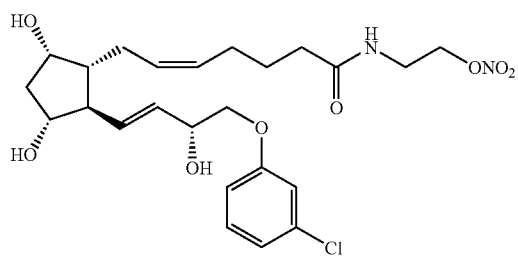
(132)
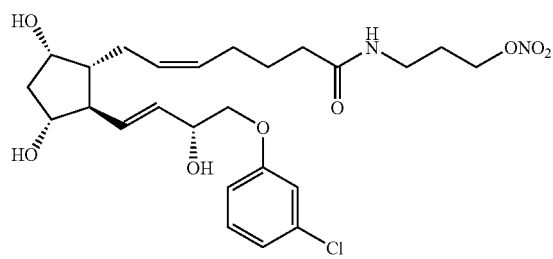
(133)
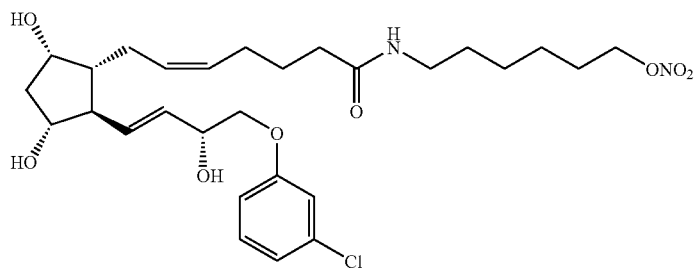
(134)
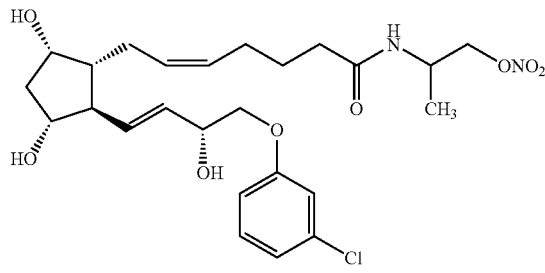
(135)
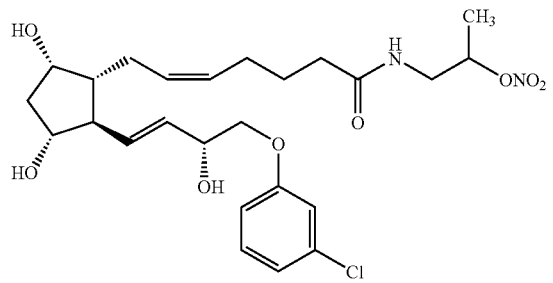

(136)
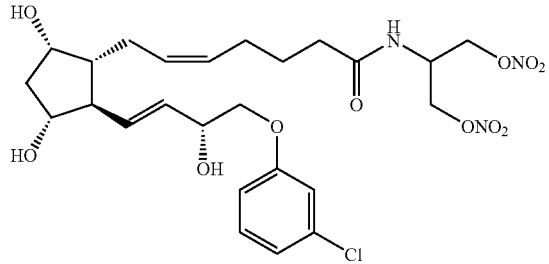
(137)
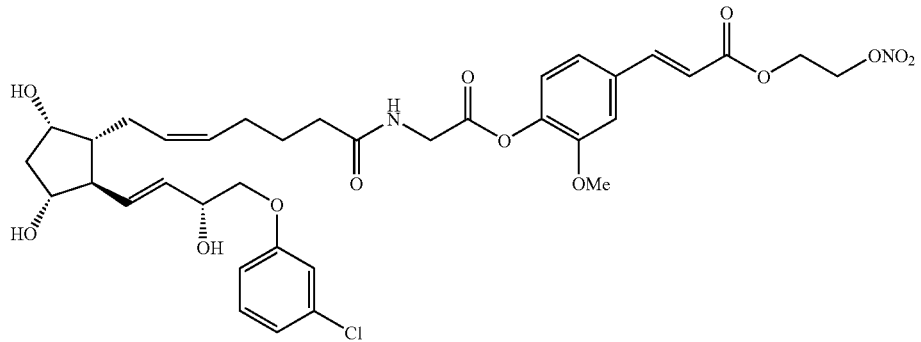
(138)
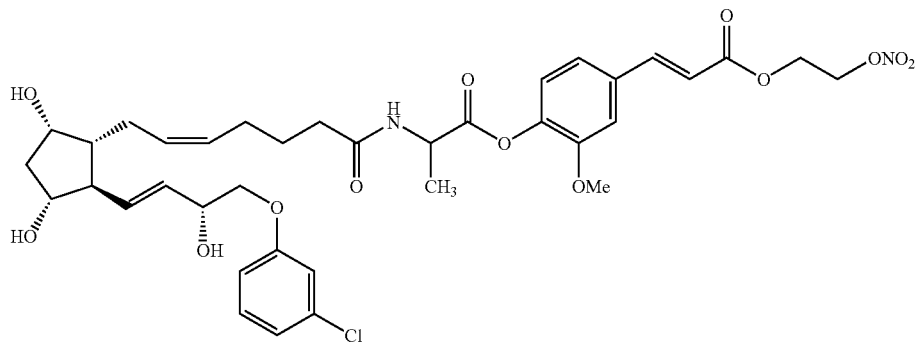
(139)
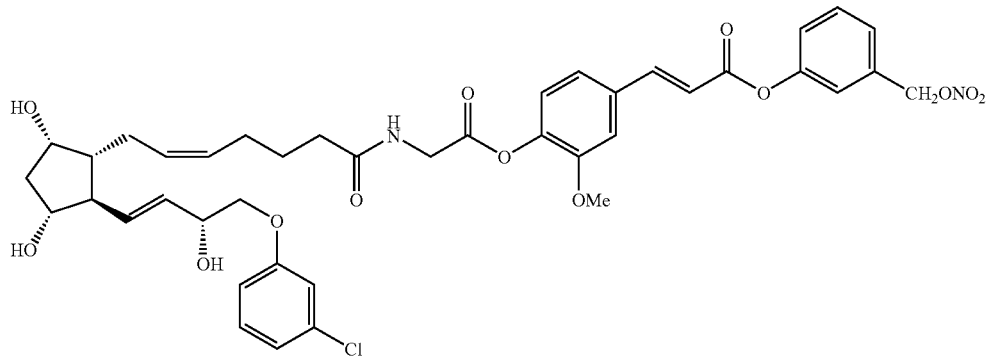

(140)
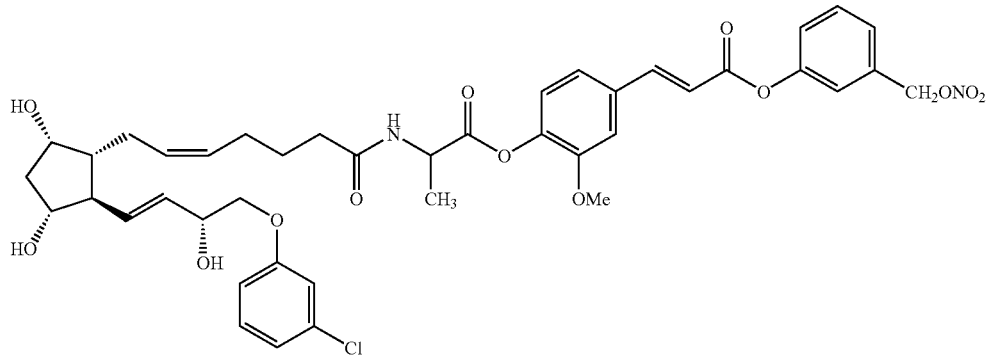
(141)
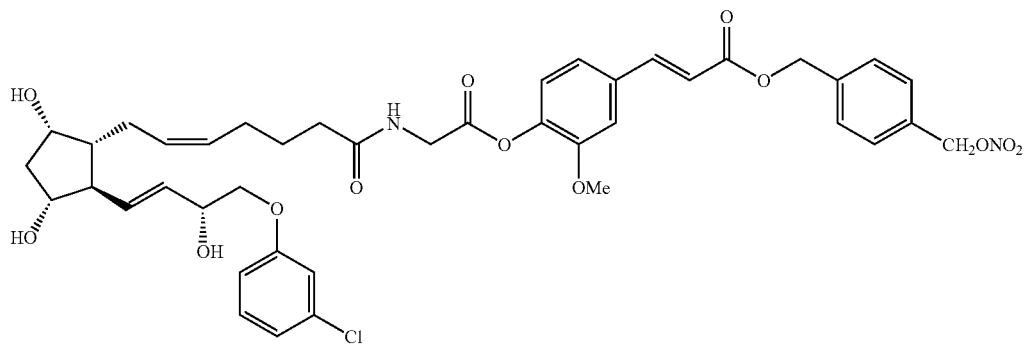
(142)
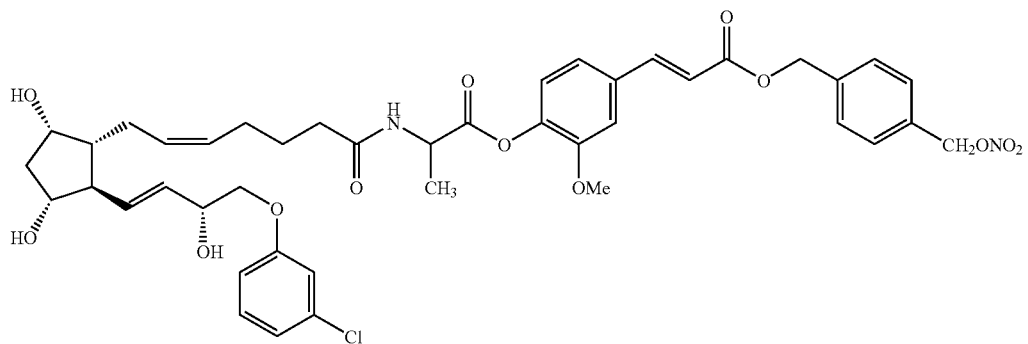
(143)
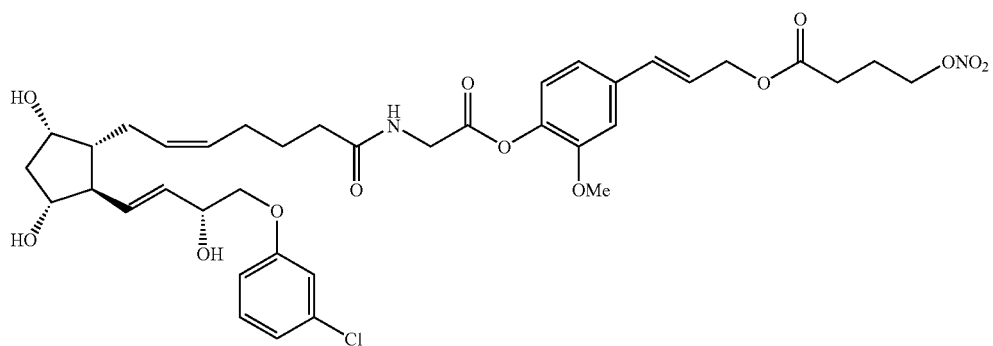

(144)
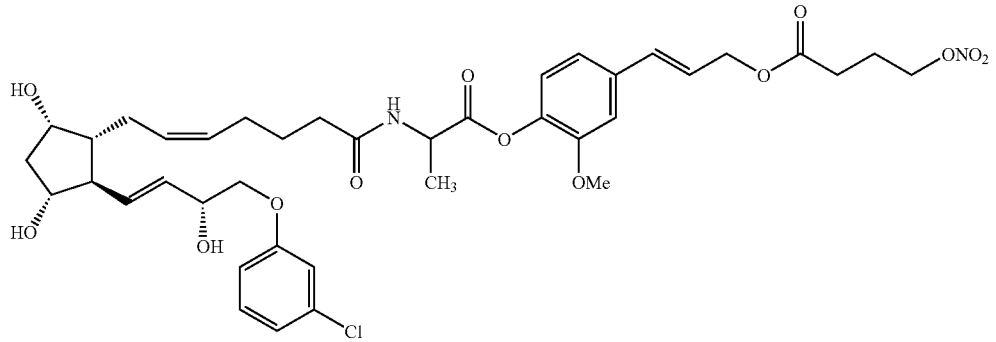
(145)
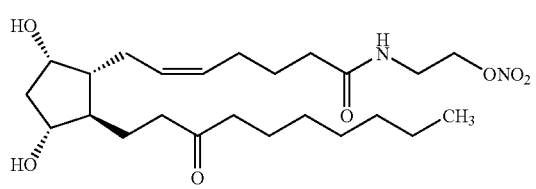
(146)
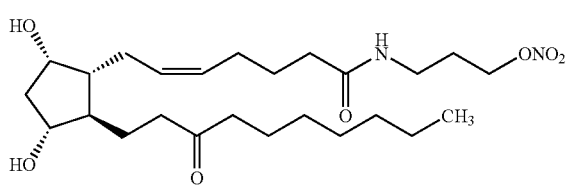
(147)
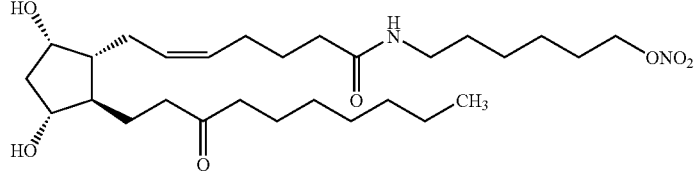
(148)
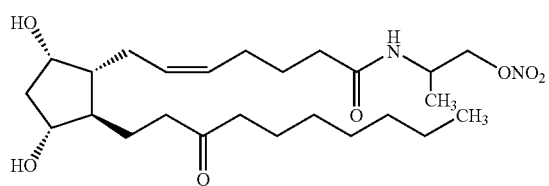
(149)
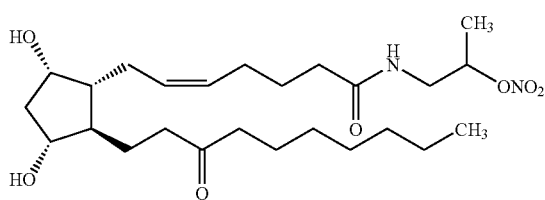
(150)
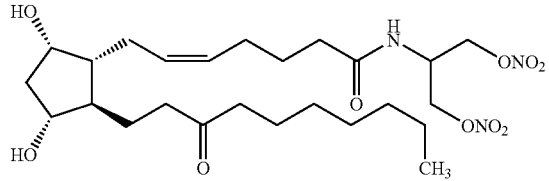
(151)
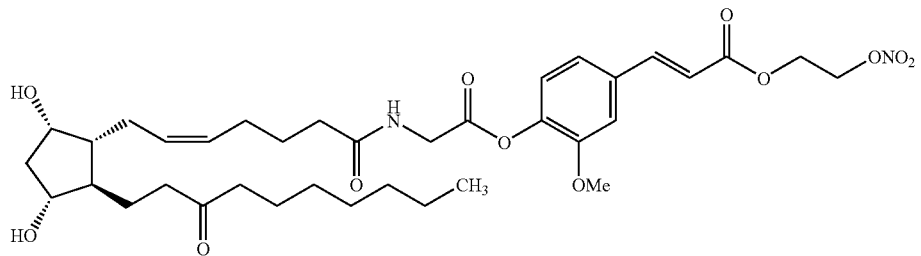

-continued
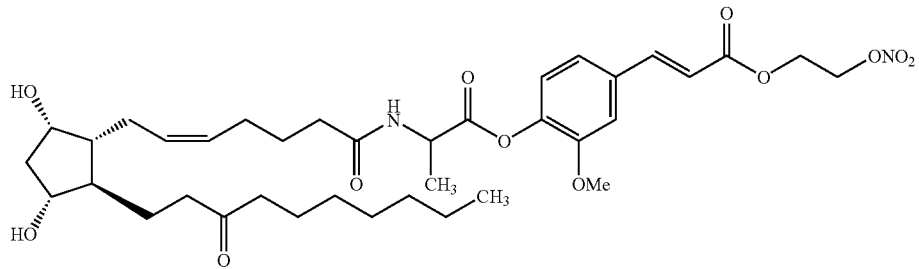
(152)
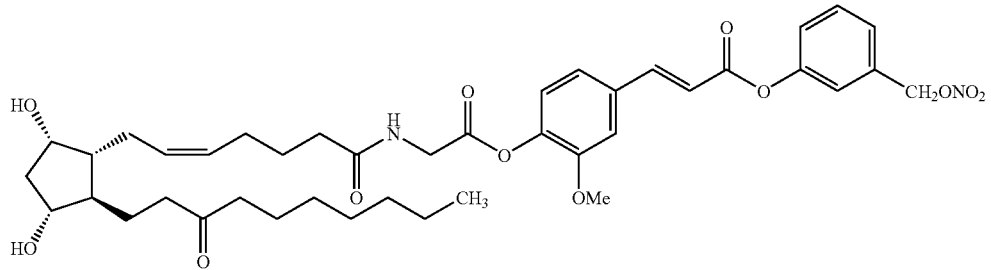
(153)
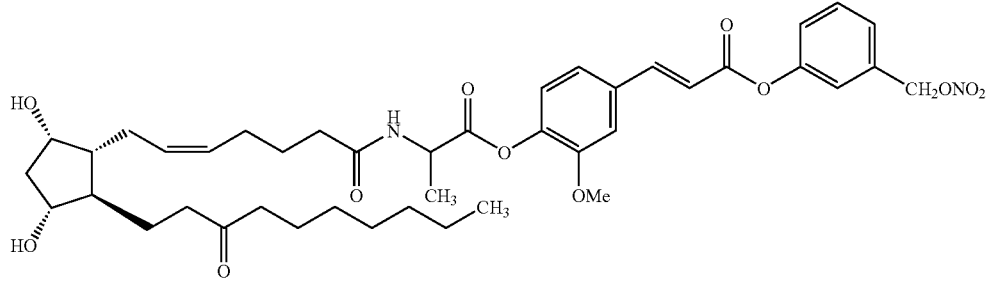
(154)
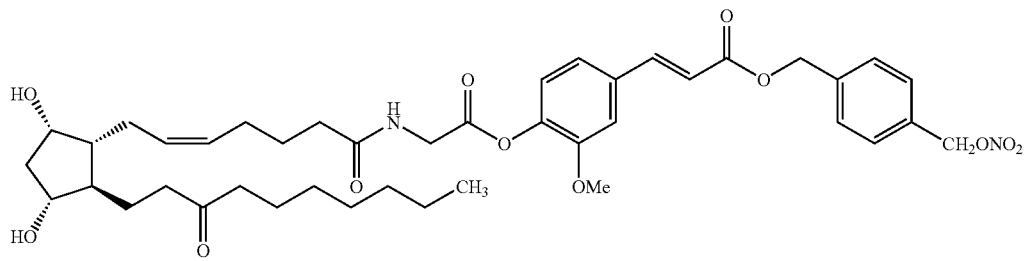
(155)
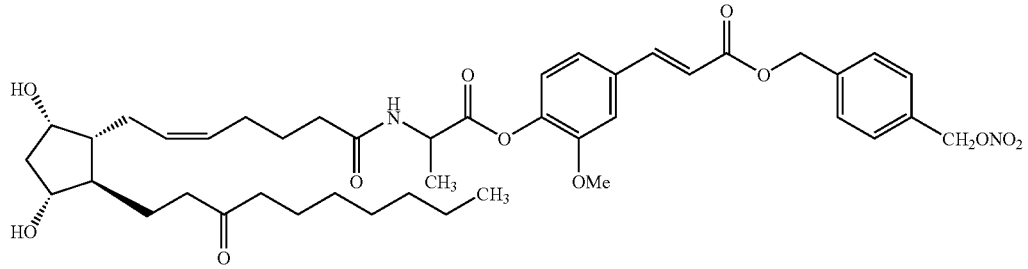
(156)

-continued
(157)
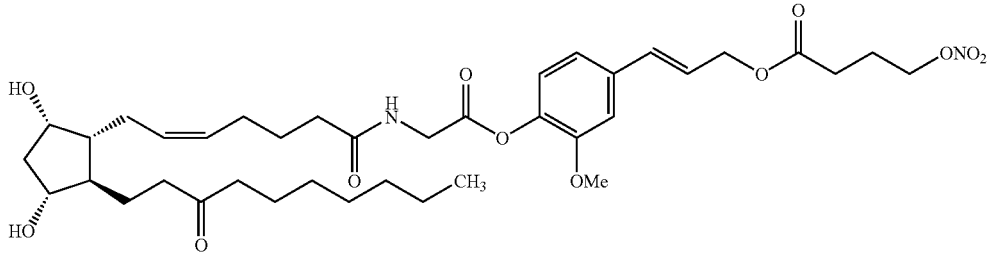
(158)
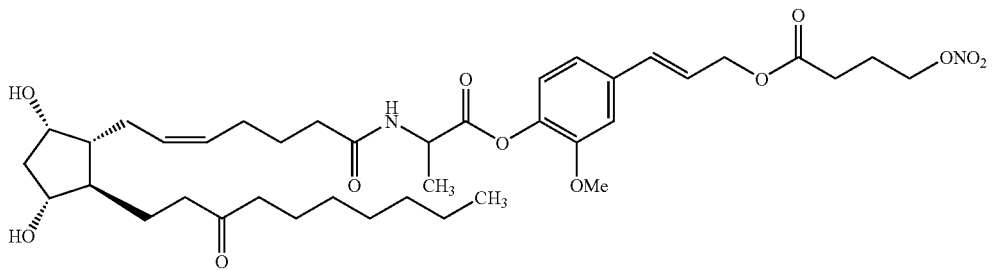
(159)
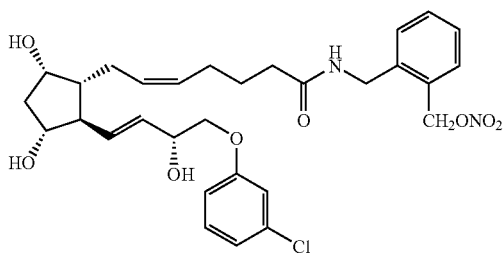
(160)
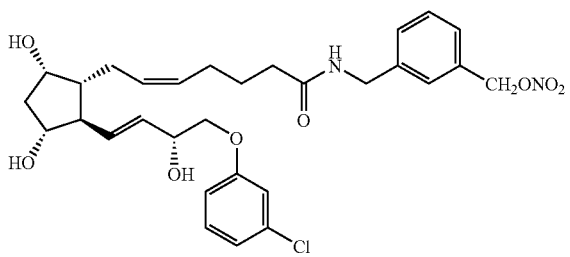
(161)
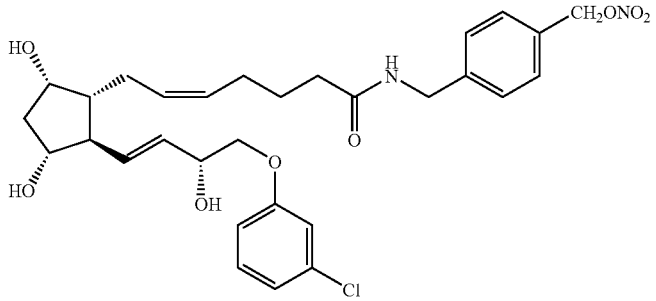
(162)
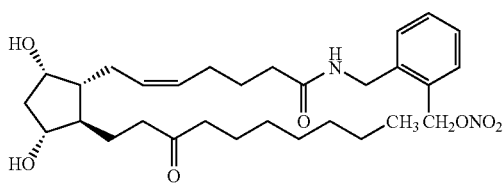
(163)
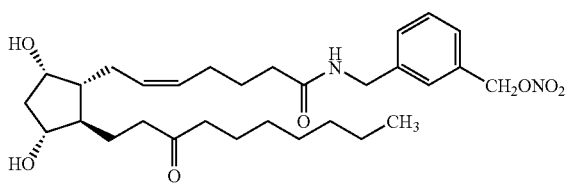
(164)
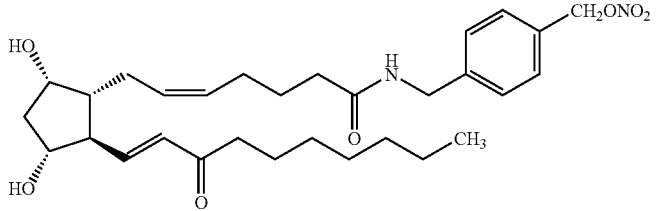

-continued
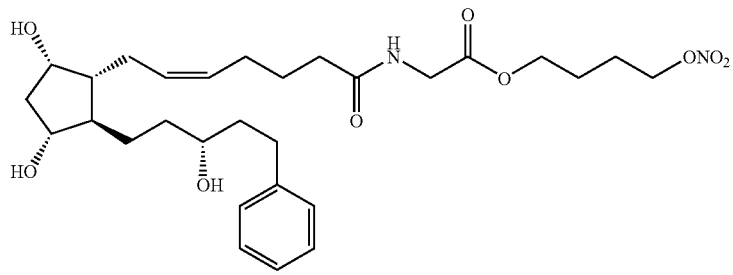
(165)
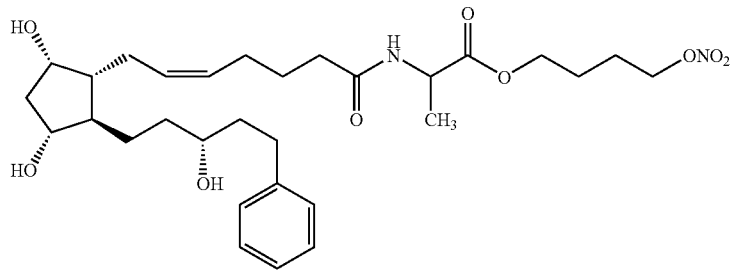
(166)
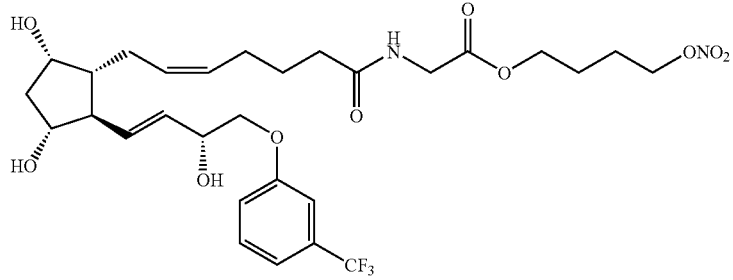
(167)
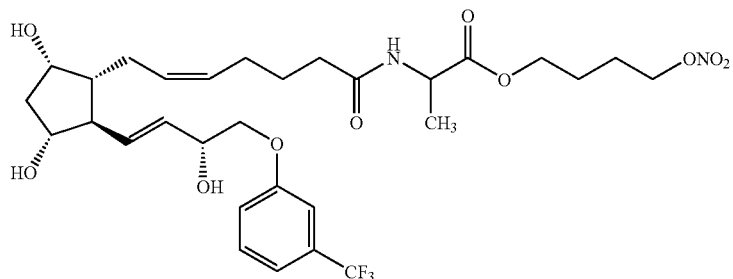
(168)
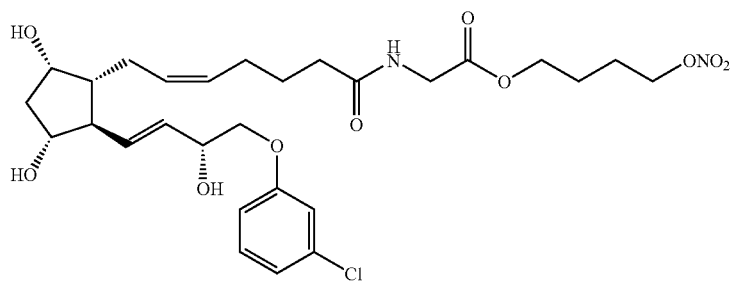
(169)

-continued
(170)
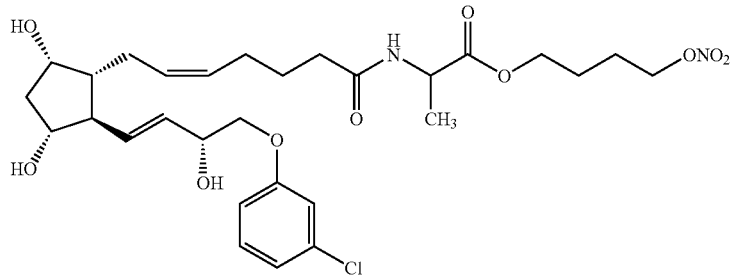
(171)
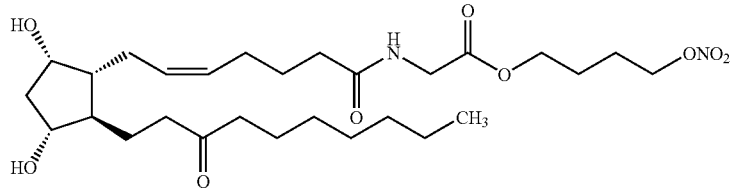
(172)
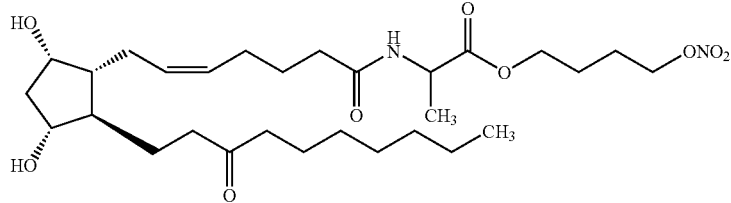
(173)
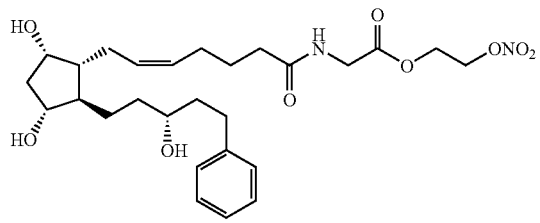
(174)
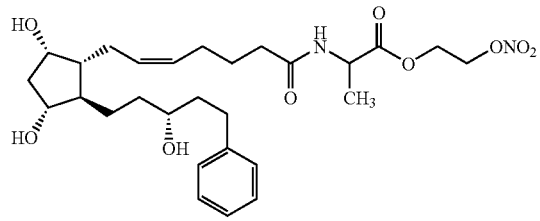
(175)
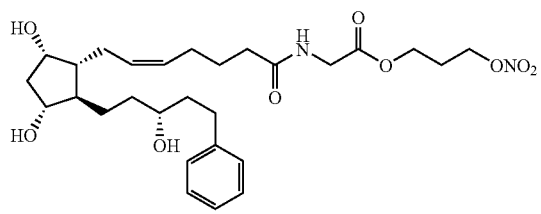
(176)
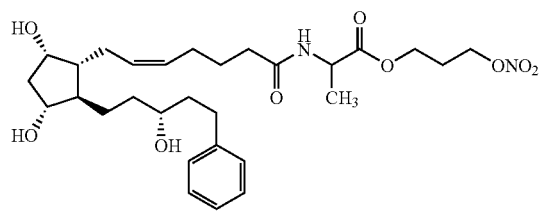
(177)
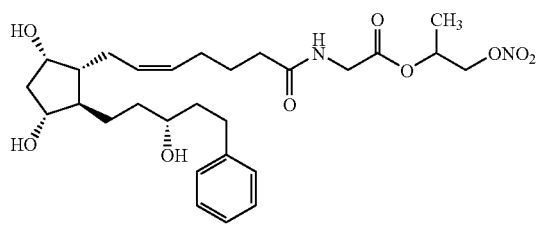
(178)
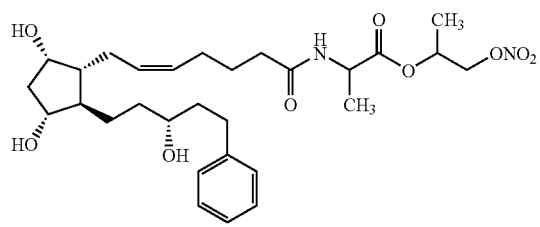

-continued
(179)
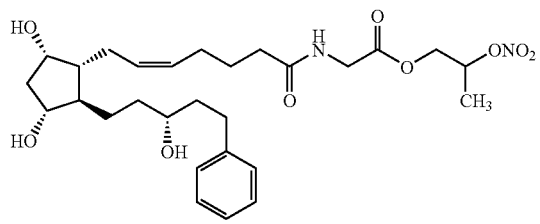
(180)
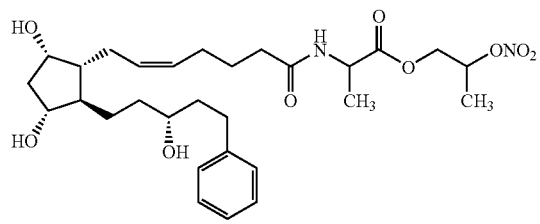
(181)
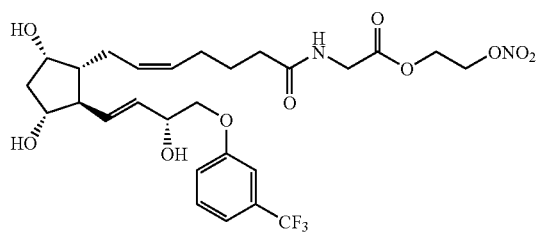
(182)
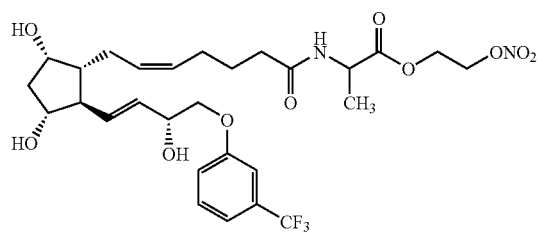
(183)
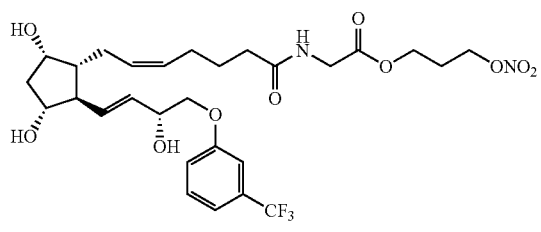
(184)
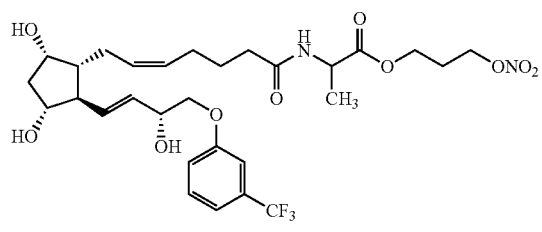
(185)
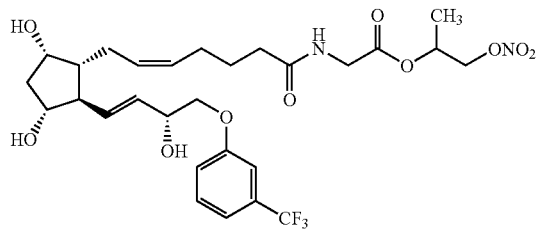
(186)
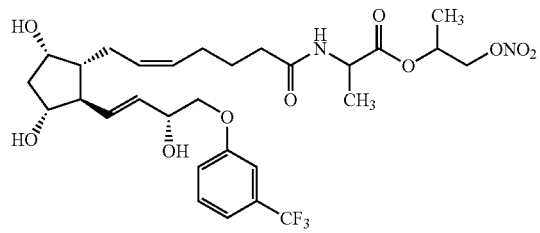
(187)
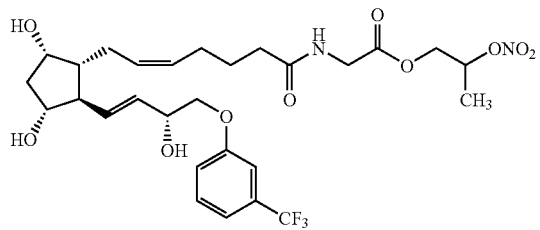
(188)
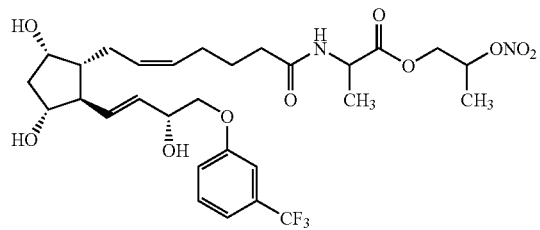
(189)
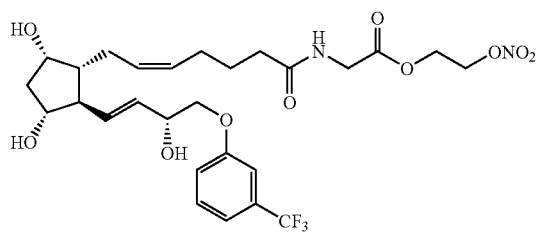

-continued
(191)
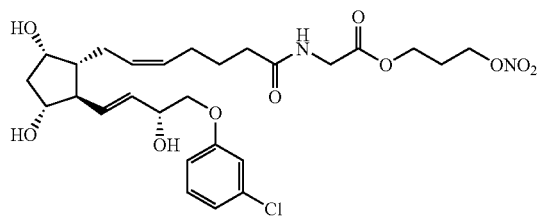
(192)
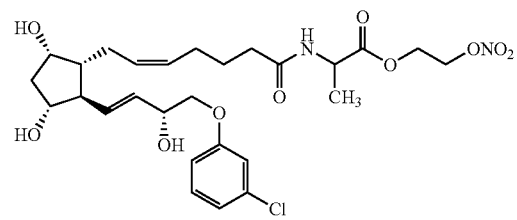
(193)
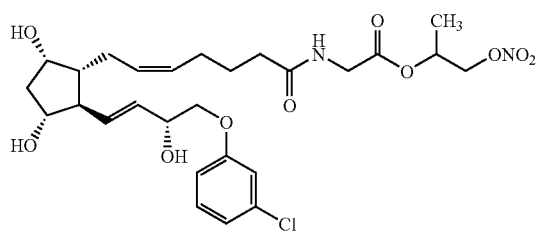
(194)
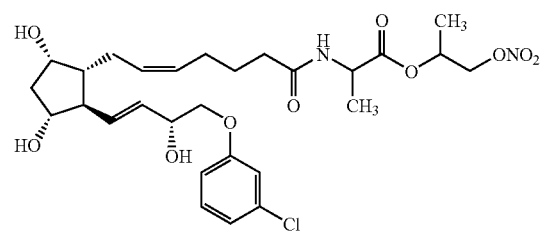
(195)
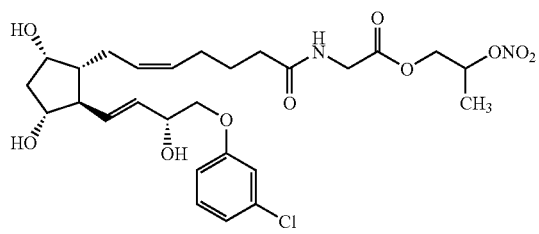
(196)
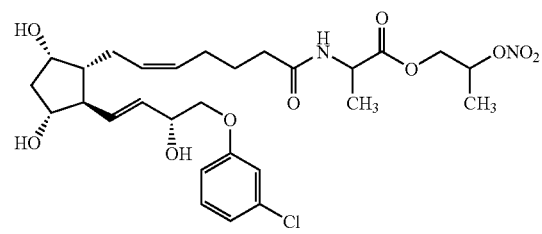
(197)
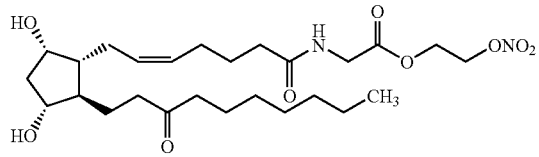
(198)
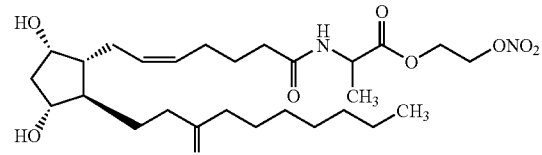
(199)
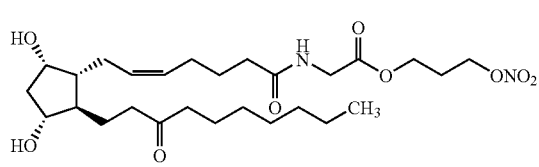
(200)
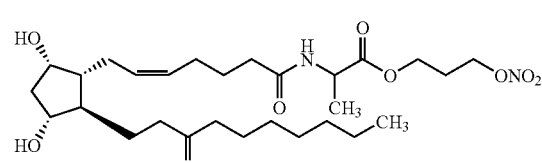
(201)
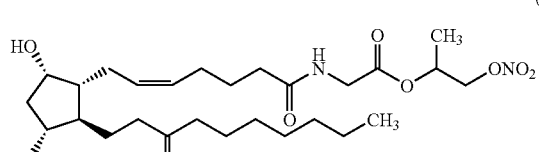
(202)
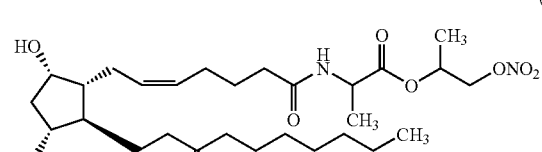
(203)
(204)

-continued
(205)
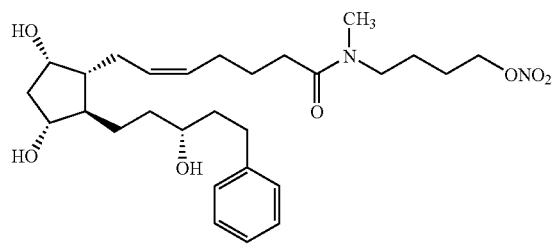
(206)
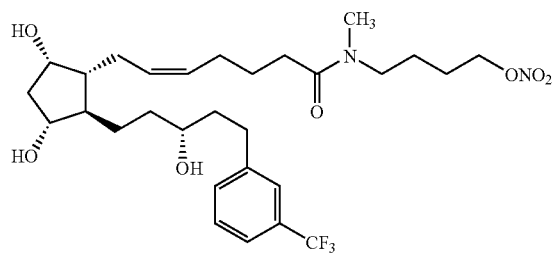
(207)
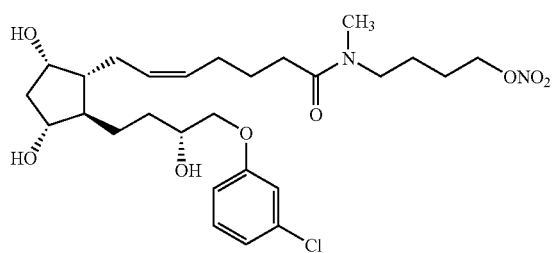
(208)
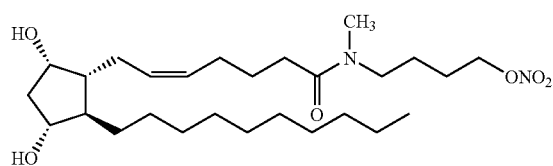
(209)
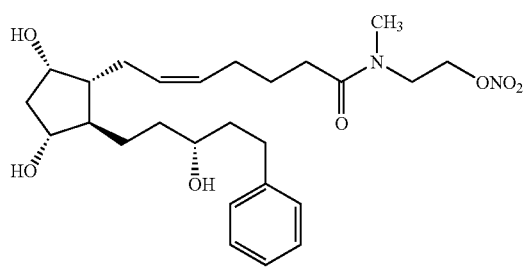
(210)
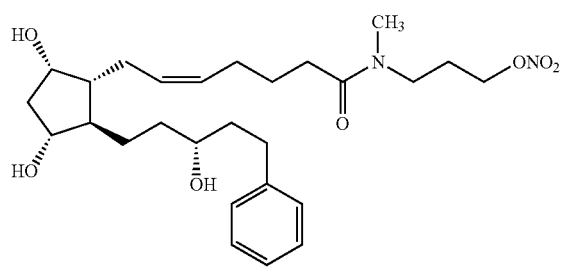
(211)
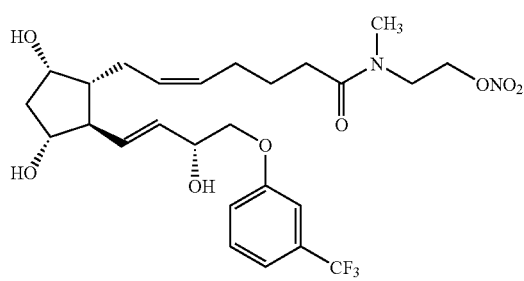
(212)
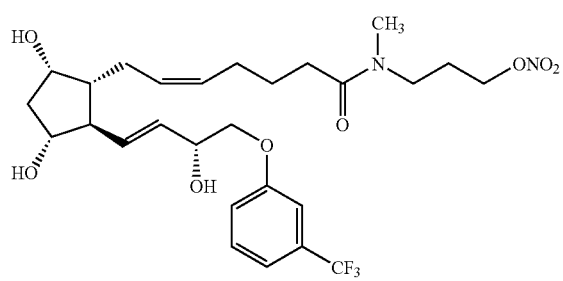
(213)
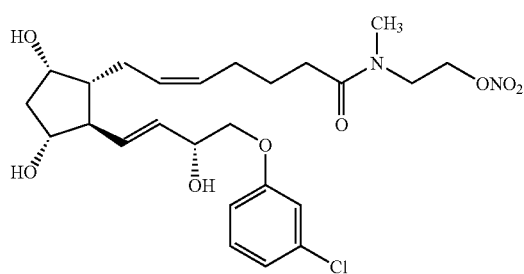
(214)
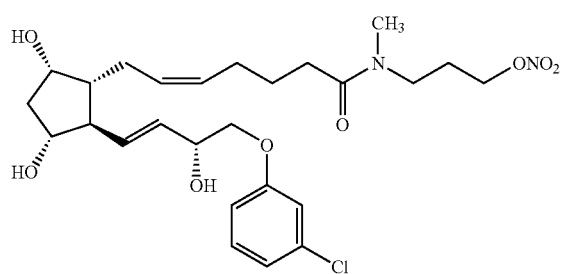

-continued

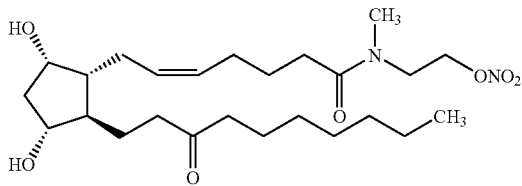 (215)

and

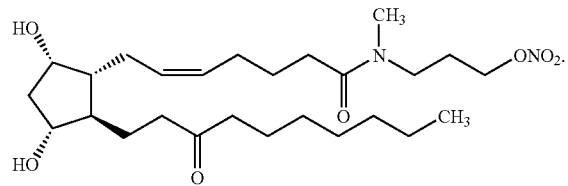 (216)

9. A process for preparing a compound of general formula (I) as defined in claim 1, which process comprises:

a) reacting a compound of formula (III)

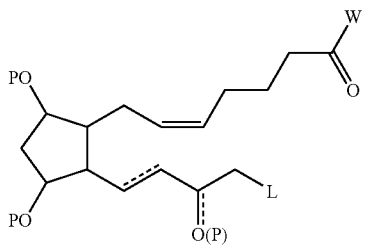

wherein

L is as above defined; P is H or a hydroxylic protecting group, W is —OH, Cl, or —OC(O)R$_1$ wherein R$_1$ is a linear or branched C$_1$-C$_5$ alkyl;

with a compound of formula (IV)

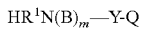 (IV)

wherein R$^1$, Y, B and m are as above defined,

Q is —ONO$_2$ or Z$_1$ wherein

Z$_1$ is selected from the group consisting of chlorine, bromine, iodine, mesyl, tosyl; and b) when Q is Z$_1$, converting the compound obtained in the step a) into the corresponding nitro derivative by reaction with a nitrate source; and c) optionally deprotecting the compound obtained in step a) or b).

10. A compound of general formula (I) according to claim 1 for use as a medicament.

11. A pharmaceutical composition comprising a pharmaceutically acceptable carrier and a pharmaceutically effective amount of a compound of general formula (I) and/or a salt or stereoisomer thereof as defined in claim 1.

12. A pharmaceutical composition according to claim 11 in a suitable form for the topical administration.

13. A pharmaceutical composition according to claim 11 for the treatment of glaucoma and ocular hypertension.

14. A pharmaceutical composition according to claim 11, wherein the compound of general formula (I) is administered as a solution, suspension or emulsion in an ophthalmically acceptable vehicle.

15. A method for treating glaucoma or ocular hypertension, said method comprising contacting an effective intraocular pressure reducing amount of a pharmaceutical composition according to claim 11, with the eye in order to reduce eye pressure and to maintain said pressure on a reduced level.

16. A pharmaceutical composition comprising a mixture of a compound of formula (I) as defined in claim 1 and (i) a beta-blocker or (ii) a carbonic anhydrase inhibitor or (iii) an adrenergic agonist.

17. A pharmaceutical composition comprising a mixture of a compound of formula (I) as defined in claim 1 and timolol.

\* \* \* \* \*